United States Patent
Tanaka et al.

(10) Patent No.: US 7,875,745 B2
(45) Date of Patent: Jan. 25, 2011

(54) COMPOUNDS HAVING LYSOPHOSPHATIDIC ACID RECEPTOR ANTAGONISM AND USES THEREOF

(75) Inventors: Motoyuki Tanaka, Mishima-gun (JP); Shinji Nakade, Tsukuba (JP); Yoshikazu Takaoka, Mishima-gun (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 266 days.

(21) Appl. No.: 10/583,469

(22) PCT Filed: Dec. 17, 2004

(86) PCT No.: PCT/JP2004/019456
§ 371 (c)(1),
(2), (4) Date: Jun. 19, 2006

(87) PCT Pub. No.: WO2005/058790
PCT Pub. Date: Jun. 30, 2005

(65) Prior Publication Data
US 2007/0149595 A1    Jun. 28, 2007

(30) Foreign Application Priority Data
Dec. 19, 2003   (JP) .................. P. 2003-422431
Mar. 30, 2004   (JP) .................. P. 2004-101378

(51) Int. Cl.
C07C 53/134   (2006.01)
A61K 31/19    (2006.01)
(52) U.S. Cl. ..................... 562/496; 514/570
(58) Field of Classification Search ............... 562/496; 514/570
See application file for complete search history.

(56) References Cited

U.S. PATENT DOCUMENTS

2006/0148830 A1* 7/2006 Terakado et al. ......... 514/264.1
2007/0149595 A1  6/2007 Tanaka et al.

FOREIGN PATENT DOCUMENTS

| JP | 62-164661 A | 7/1987 |
| JP | 1-299283 A | 12/1989 |
| JP | 10-287651 A | 10/1998 |
| JP | 2001-226362 A | 8/2001 |
| JP | 2002-293764 A | 10/2002 |
| WO | WO 02/062389 A1 | 8/2002 |
| WO | WO 2004/002530 A1 | 1/2004 |
| WO | WO 2004/031118 A1 | 4/2004 |

OTHER PUBLICATIONS

Contos et al., (Mol Pharmacol 58:1188-1196, 2000).*
Kubinyi (3D QSAR in Drug Design: Ligand-Protein Interactions and Molecular Similarity, vol. 2-3, Springer, 1998, 800 pages).*
Bryn et al., Pharm. Res., v. 12, n. 7, p. 945-54, 1995.*
Heasley et al. (Bioorganic & Medicinal Chemistry Letters 14 (2004) 2735-2740).*
International Search Report for PCT/JP04/019456 dated Apr. 12, 2005.
Dorwald F. Zaragoza, "Side Reactions in Organic Synthesis", 2005, p. IX of Preface, Wiley: VCH, Weinheim.

* cited by examiner

Primary Examiner—Robert Havlin
(74) Attorney, Agent, or Firm—Sughrue Mion, PLLC

(57) ABSTRACT

The present invention relates to a compound represented by formula (I):

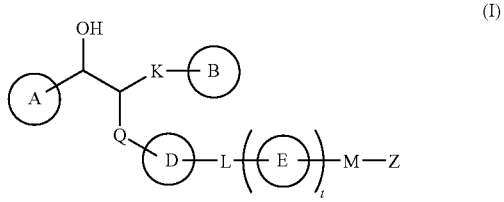

(wherein the symbols in formula were described in the description), a salt thereof, a solvate thereof or a prodrug thereof. Since the compound of the present invention binds to and is antagonistic to an LPA receptor (particularly, EDG-2), it is useful for prevention and/or treatment of urinary system disease (prostatic hypertrophy or neurogenic bladder dysfunction disease, spinal cord neoplasm, nucleous hernia, spinal canal stenosis, diseases caused by diabetes, occlusion disease of lower urinary tract, inflammatory disease of lower urinary tract, and polyuria), carcinoma-associated disease, proliferative disease, inflammation system disease, immune system disease, disease by secretory dysfunction, brain-related disease and/or chronic disease.

12 Claims, No Drawings

COMPOUNDS HAVING LYSOPHOSPHATIDIC ACID RECEPTOR ANTAGONISM AND USES THEREOF

TECHNICAL FIELD

The present invention relates to a compound having antagonistic activity against lysophosphatidic acid receptor (especially EDG-2) which is useful as medicament, a process for producing the same and the use thereof.

BACKGROUND ART

It is known that various lipid mediators such as eicosanoid and platelet activating factor (PAF) are produced by the activity of phospholipase from cell membranes.

Lysophosphatidic acid (hereinafter abbreviated as LPA) of formula (A):

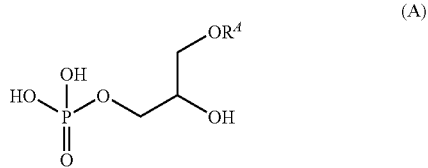

(A)

(wherein $R^A$ is acyl, alkenyl or alkyl)

is a lipid which is produced from cell membranes or phospholipid which is present in the blood, acts as a mediator for signal transduction and delivers various signals into cells. LPA that exists naturally is L-α-LPA.

Recently, the existence of three subtypes of LPA receptor has been disclosed and it is gradually proved that their physiological activities are via LPA receptor. Three subtypes of LPA receptor are called EDG (Endothelial differentiation gene)-2, 4 and 7, respectively, and form part of EDG receptor family as well as EDG-1, 3, 5, 6 and 8 that are sphingosine-1-phosphate receptor. EDG-2 is also called LPA1 or VZG (Ventricular zone gene)-1 (*Mol. Pharmacol.,* 2000, December; 58(6): 1188-96). LPA receptor to which LPA binds delivers signals into cells via G-protein coupled to the receptor. Gs, Gi, Gq, etc. are known as G-proteins that can bind to LPA receptor, and the receptors are said to relate to the response to the action of increase or, adversely, decrease of cell growth. Furthermore, since MAP-kinase systems operate in the downstreams of G-proteins, it has been known that LPA receptors deliver various signals.

Since localization of LPA receptors is different between their subtypes although they exist widely in living body, it is considered that the role of each receptor is different by the organ.

The increase of blood pressure in rats, and the contraction of colon in rats and ileum in guinea pigs have been known as the pharmacological activity induced by LPA (*J. Pharm. Pharmacol.,* 43, 774 (1991), *J. Pharm. Pharmacol.,* 34, 514 (1982)). In addition, it is known that LPA is related to urethral contraction via EDG-2 (see WO02/062389), LPA suppresses secretion of pancreatic juice (see WO03/007991), and LPA is related to chronic disease (see WO 04/002530).

In addition, concerning to the relationship between LPA and carcinoma, until now it is known that LPA enhances the proliferation of the epithelial cancer cells originated from prostate gland (*J. Cellular Physiol,* 174, 261 (1998)) and ovarian cancer cells (*J. Urol,* 163, 1027 (2000)).

In addition, it is known that LPA is related to the function of growth of various cells such as airway smooth muscle cells (*Am. J. Physiol. Lung Cell Mol. Physiol.,* , 282(1): L91 (2002)), fibroblast (*Mol. Cell. Biol.,* 18(12): 7119 (1998)), mesangial cells (*Clin. Science,* 96, 431 (1999)), hepatocyte, liver stellate cells (*Biochem. Biophys. Res. Commun.,* 248, 436 (1998)), vasucular smooth muscle cells (*Am. J. Physiol.,* 267 (*Cell Physiol*.36): C204 (1994)), vascular endothelial cells (*Am. J. Physiol. Cell Physiol.,* 278(3): C612 (2000)), glia cells/Schwann cells (*Proc. Natl. Acad. Sci. USA,* 96, 5233 (1999)), adipocytes (*J. Clin. Invest.,* 101, 1431 (1998)) as well as cancer cells. Especially, since it is known that LPA is related to glioblastoma, it is considered that an EDG-2 antagonist is used as an agent for preventing and/or treating diseases relating to glioblastoma (e.g., brain tumor, etc.). Particularly, in addition, it is known that LPA is related to the function of chemotaxis of inflammatory cells as well as cancer cells besides cell growth (*Biochem. Biophys. Res. Commun.,* 15; 193(2), 497 (1993)). Moreover it is known that LPA is related to proliferation of immune cells and has an activity of controlled secretion of cytokine (*J. Imunnol,* 162 2049 (1999)), platelet aggregation activity (*Biochem. Biophys. Res. Commun.,* 99, 391 (1981)). Besides, from analysis of knockout mouse of EDG-2 which is one of the LPA receptor, EDG-2 is concerned to be related to the brain function and pain (*Proc. Natl. Acad. Sci. USA,* 97, 13384 (2000), *Nat. Med, July;* 10(7): 712 (2004)).

From these evidences, it is thought that a drug antagonizing to LPA receptor is useful for prevention and/or treatment of diseases such as various kinds of disease namely urinary system disease, carcinoma-associated disease, proliferative disease, inflammation/immune system disease, disease by secretory dysfunction, brain-related disease or chronic disease.

For example, for urinary system disease, prostatic hypertrophy or neurogenic bladder dysfunction disease, and dysuria (micturation initiation delay, extension between on urination, urinary stream very small, intermission micturation, two steps of micturation, etc.), pollakiuria, night urination, urodynia, etc. are known as symptoms with a urinary system disease. Similar urologic symptoms are symptoms caused by cerebrovascular disorder, Parkinson disease, brain tumor, a multiple sclerosis, Shy-Drager symptom, spinal cord neoplasm, nucleous hernia, spinal canal stenosis, diabetes, etc. (such as dysuria (micturation initiation delay, extension between on urination, urinary stream very small, intermission micturation, two steps of miction), pollakiuria, night urination, urodynia). For other example, for urinary system disease, lower urinary tract symptom (for example, occlusion disease of lower urinary tract), inflammatory disease of lower urinary tract (such as infection), interstitial cystitis and polyuria are thought about. And, these diseases are controlled by LPA receptor antagonists.

For example, for carcinoma-associated disease, solid tumor, solid tumor metastasis, angiofibroma, myeloma, multiple myeloma, Kaposi's sarcoma, leucemia are given. In solid tumor, mammary cancer, lung cancer, gastric cancer, carcinoma oesophagi, colon rectal cancer, large intestinal tumor, liver cancer, ovarian cancer, theca cell tumor, androblastoma, cervix cancer, endometrial carcinoma, prostate cancer, kidney cancer, carcinoma cutaneum, osteosarcoma, pancreas cancer, urinary tract carcinoma, thyroid cancer, or brain tumor, etc. are given. In addition, it is thought that carcinomatous infiltration transition is suppressed by LPA receptor antagonist.

For example, for proliferative disease, the disease with aberrant angiogenesis are given (for example, re-arctation, diabetic retinopathy, angiogenesis-related glaucoma, crystalline lens fiber multiplication symptom, thyroid gland hyperplasia (including Basedow's disease), lung inflammation, nephrotic syndrome or osteoporosis), and also artery obstruction, or pulmonary fibrosis, etc. are given.

For example, for inflammation/immune system disease, psoriasis, nephropathy (for example, IgA nephropathy, etc.), nephritis by other inflammation /immunopathy, hepatitis, or pneumonitis symptom, etc. are given.

For example, for secretory dysfunction, secretory dysfunction by autonomic nervous system dysfunction is given, for example, for secretory dysfunction by autonomic nervous system dysfunction, Sjogren syndrome, etc. is given.

For example, for brain-/nerve-related disease, brain infarction, cerebral apoplexy, brain or peripheral neuropathy, etc. are given. Also, for nervous disease relating to pain, cancer pain, chronic pelvic pain syndrome, algesia, allodynia, etc. are given.

For example, for chronic disease, chronic asthma, glomerulonephritis, obesity, prostate hyperplasia, chronic prostatitis, diseases caused by arteriosclerosis process, rheumatism or atopic dermatitis, cirrhosis, fatty liver, chronic diarrhea, chronic constipation, etc. are given.

The compound of formula (B)

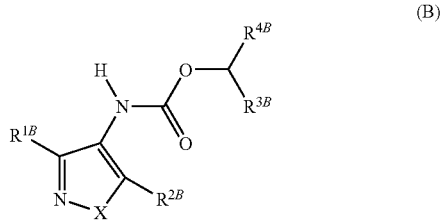

(B)

[wherein $R^{1B}$ represents optionally substituted alkyl, aryl, heterocyclic radical, alkyloxy, aryloxy, alkylthio, arylthio or halogen atom, $R^{2B}$ represents optionally substituted alkyl, aryl, heterocyclic radical, alkyloxy, aryloxy or halogen atom, $R^{3B}$ represents hydrogen atom, lower alkyl or alkyl substituted with halogen atom, $R^{4B}$ represents a radical selected from (a) optionally substituted phenyl, aryl or heterocyclic radical, (b) substituted or non-substituted alkyl or (c) substituted or non-substituted alkenyl, $X^B$ represents oxygen atom or sulfur atom. With the proviso that $R^{3B}$ and $R^{4B}$ may form a five- to ten-membered cyclic structure together with a carbon atom to which they bind, and when $R^{3B}$ is a hydrogen atom, $R^{4B}$ represents a group other than methyl.]

or a salt thereof is known as a compound having an antagonistic activity against the LPA receptor (see WO01/60819).

The compound of formula (C)

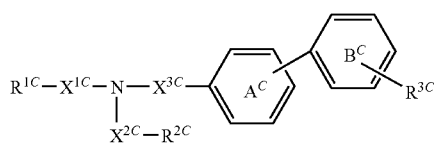

(C)

[wherein $R^{1C}$ is an aliphatic hydrocarbon group which is unsubstituted or substituted halogen or hydroxy; $X^{1C}$ is CO, $SO_2$ or —O—C(=O)—, in which the carbon atom in the carbonyl group is bound to a nitrogen atom represented by formula (C); $X^{2C}$ is a divalent aliphatic hydrocarbon group which is unsubstituted or substituted with hydroxy, carboxy, amino, guanidino or a cyclic or aromatic group, or a divalent alicyclic hydrocarbon group, in which the carbon atom in the aliphatic hydrocarbon group may be further crosslinked with a divalent aliphatic hydrocarbon group; $R^2c$ is carboxy which is optionally esterified or amidated, substituted or unsubstituted amino, formyl which is optionally acetalated, 1H-tetrazol-5-yl, pyridyl, hydroxy which is optionally etherified, $S(O)_{mC}$—$R^C$ (wherein mC is 0, 1 or 2, and $R^C$ is hydrogen or an aliphatic hydrocarbon group), alkanoyl, unsubstituted or N-substituted sulfamoyl, or $PO_{nC}H_2$ (wherein nC is 2 or 3); $X^{3C}$ is a divalent aliphatic hydrocarbon; $R^{3C}$ is carboxy, 5-tetrazolyl, $SO_3H$, $PO_2H_2$, $PO_3H_2$ or haloalkylsulfamoyl, and ring $A^C$ and ring $B^C$ are each independently substituted or unsubstituted]

or a salt thereof is known as a compound having an antagonistic activity against the angiotensin II (see EP443983).

Also, the compound of formula (D)

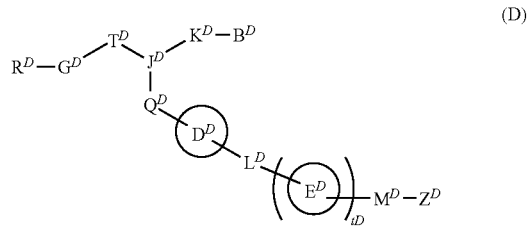

(D)

[wherein $R^D$ is an aliphatic hydrocarbon group which may be substituted or a cyclic group which may have a substituent(s); $G^D$ is a bond or a spacer having from 1 to 8 atoms in its principle chain; $T^D$ is —$CH_2$— or a spacer containing a hydrogen bond receptor which may have a substituent(s) and having one atom in its principle chain; $J^D$ is a nitrogen atom or a carbon atom; $B^D$ is an aliphatic hydrocarbon group which may be substituted or a cyclic group which may have a substituent(s); $K^D$ is (1) a bond or (2) a spacer having from 1 to 8 atoms which may form a ring together with a substituent on the cyclic ring of $R^D$, ring $D^D$ or a substituent on ring $D^D$; $Q^D$ is (1) a bond or (2) a spacer having from 1 to 8 atoms in its principle chain which may form a ring together with the cyclic group of $R^D$, a substituent on the cyclic ring of $R^D$, or $K^D$; ring $D^D$ is a cyclic group which may have a further substituent(s); $L^D$ is a bond or a spacer having from 1 to 3 atoms in its principle chain; ring $E^D$ is a cyclic group which may have a further substituent(s); $M^D$ is a bond or a spacer having from 1 to 8 atoms in its principle chain; $Z^D$ is an acidic group; and $t^D$ is 0 or 1]

or a salt thereof is known as a compound having an antagonistic activity against the EDG-2 (see WO04/31118).

DISCLOSURE OF THE INVENTION

An agent of prevention and/or treatment of urinary system disease, carcinoma-associated disease, proliferative disease, inflammation/immune system disease, disease caused by secretory dysfunction, brain-related disease and/or chronic disease, etc. is useful for drug. It is eagerly desired to development of an LPA receptor (especially EDG-2) antagonist which is excel at oral absorption, and safety.

The inventors of the present invention have carried out intensive studies for finding compounds which specifically binds to LPA receptors (especially EDG-2) and exerts antagonistic activity, and as a result, they have found that a compound of formula (I) achieves the problem to accomplish the present invention.

The present invention can provide the novel compound which becomes a medicine for treatment of various kinds of diseases by showing antagonistic activity to LPA receptor. For example, the compound of formula (I) of the present invention may be an agent of prevention and/or treatment such as the urinary system disease that does not influence blood pressure is provided.

The compound of formula (I) of the present invention is a novel compound which is not known till now. Also, the compound of formula of the present invention has excellent pharmacokinetic properties (e.g., high BA (bioavailability), prolonged action for a long time, etc.).

The present invention relates to the followings:

[1] A compound of formula (I)

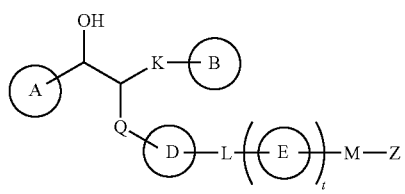

(I)

wherein ring A and ring B each independently represents a cyclic group which may have a substituent(s);

K, Q and M each independently represents a bond or a spacer having from 1 to 8 atoms in its principle chain;

ring D and ring E each independently represents a cyclic group which may have a substituent(s);

L represents a bond, or a spacer having from 1 to 3 atoms in its principle chain;

Z represents an acidic group; and t represents 0 or 1, or a salt thereof, a solvate thereof or a prodrug thereof

[2] The compound according to the above [1], wherein the compound of formula (I) is an optically active compound of formula (I-A):

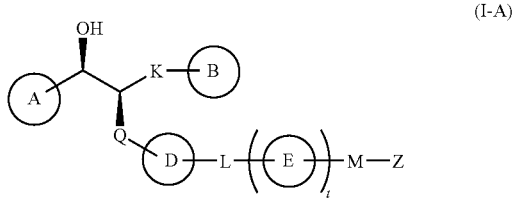

(I-A)

wherein ⟋ represents β-configuration; and other symbols have the same meanings as described in the above [1].

[3] The compound according to the above [1], wherein ring A is a benzene ring which may have a substituent(s).

[4] The compound according to the above [1], wherein K is C1-4 alkylene which may be substituted.

[5] The compound according to the above [1], wherein ring B is an indane ring which may have a substituent(s).

[6] The compound according to the above [1], wherein Q is methylene which may be substituted or ethylene which may be substituted.

[7] The compound according to the above [1], wherein ring D is a benzene ring which may have a substituent(s), a pyrazole ring which may have a substituent(s) or a pyrrole ring which may have a substituent(s).

[8] The compound according to the above [1], wherein Z is —COOH; —CONHSO$_2$R$^1$, in which R$^1$ represents an aliphatic hydrocarbon group which may be substituted or a cyclic group which may have a substituent(s); or tetrazolyl.

[9] The compound according to the above [1], wherein

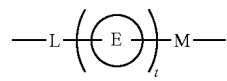

is methylene which may be substituted, ethylene which may be substituted, propylene which may be substituted, or ethenylene which may be substituted.

[10] The compound according to the above [1], wherein ring A is a benzene ring which may have a substituent(s);

ring B is an indane ring which may have a substituent(s);

ring D is a benzene ring which may have a substituent(s), a pyrazole ring which may have a substituent(s) or a pyrrole ring which may have a substituent(s);

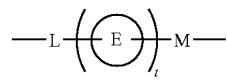

is methylene which may be substituted, ethylene which may be substituted, propylene which may be substituted, or ethenylene which may be substituted; and Z is —COOH; —CONHSO$_2$R$^1$, in which R$^1$ has the same meaning as described in the above [8]; or tetrazolyl.

[11] The compound according to the above [1], which is selected from the group consisting of:

(1) {1-[(2S,3S)-2-(2,3-dihydro-1H-inden-2-ylmethyl)-3-(3,5-dimethoxy-4-methylphenyl)-3-hydroxylpropyl]-1H-pyrrol-3-yl}acetic acid, (2) (1-{(2S)-2-[(S)-(3,5-dimethoxy-4-methylphenyl)(hydroxy)methyl]-5-thien-3-ylpentyl}-1H-pyrrol-3-yl)acetic acid, (3) {1-[(2S,3S)-2-(1,3-benzodioxol-2-ylmethyl)-3-(3,5-dimethoxy-4-methylphenyl)-3-hydroxylpropyl]-1H-pyrrol-3-yl}acetic acid, (4) {1-[(2S,3S)-2-(2,3-dihydro-1H-inden-2-ylmethyl)-3-hydroxy-3-(3,4,5-trimethoxyphenyl)propyl]-1H-pyrrol-3-yl}acetic acid, (5) {1-[(2S,3S)-3-(4-acetyl-3,5-dimethoxyphenyl)-2-(2,3-dihydro-1H-inden-2-ylmethyl)-3-hydroxylpropyl]-1H-pyrrol-3-yl}acetic acid, (6) {1-[(2S,3S)-2-(2,3-dihydro-1H-inden-2-ylmethyl)-3-(4-ethyl-3,5-dimethoxyphenyl)-3-hydroxylpropyl]-1H-pyrrol-3-yl}acetic acid, (7) 3-{1-[(2S,3S)-2-(2,3-dihydro-1H-inden-2-ylmethyl)-3-(3,5-dimethoxy-4-methylphenyl)-3-hydroxylpropyl]-1H-pyrrol-3-yl}propanoic acid, (8) 3-{1-[(2S,3S)-2-(2,3-dihydro-1H-inden-2-ylmethyl)-3-hydroxy-3-(3,4,5-trimethoxyphenyl)propyl]-1H-pyrrol-3-yl}propanoic acid, (9) 3-{1-[(2S,3S)-3-(4-acetyl-3,5-dimethoxyphenyl)-2-(2,3-dihydro-1H-inden-2-ylmethyl)-3-hydroxylpropyl]-1H-pyrrol-3-yl}propanoic acid,

(10) 3-{1-[(2S,3S)-2-(2,3-dihydro-1H-inden-2-ylmethyl)-3-(4-ethyl-3,5-dimethoxyphenyl)-3-hydroxylpropyl]-1H-pyrrol-3-yl}propanoic acid,

(11) 2-{1-[(2S,3S)-2-(2,3-dihydro-1H-inden-2-ylmethyl)-3-(3,5-dimethoxy-4-methylphenyl)-3-hydroxylpropyl]-1H-pyrrol-3-yl}-N-(methylsulfonyl)acetamide, (12)[1-[(2S,3S)-2-(2,3-dihydro-1H-inden-2-ylmethyl)-3-(3,5-dimethoxy-4-methylphenyl)-3-hydroxylpropyl]-4-(methoxylcarbonyl)-1H-pyrrol-3-yl]acetic acid,

(13) N-(3-{1-[(2S,3S)-2-(2,3-dihydro-1H-inden-2-ylmethyl)-3-(3,5-dimethoxy-4-methylphenyl)-3-hydroxylpropyl]-1H-pyrrol-3-yl}propanoyl)-2-methylbenzenesulfonamide,

(14) (2E)-3-{1-[(2S,3S)-2-(2,3-dihydro-1H-inden-2-ylmethyl)-3-(3,5-dimethoxy-4-methylphenyl)-3-hydroxylpropyl]-1H-pyrrol-3-yl}acrylic acid,

(15) 2-{1-[(2S,3S)-2-(2,3-dihydro-1H-inden-2-ylmethyl)-3-(3,5-dimethoxy-4-methylphenyl)-3-hydroxylpropyl]-1H-pyrol-3-yl}-2-methylpropanoic acid, and

(16) (2E)-3-{1-[(2S,3S)-2-(2,3-dihydro-1H-inden-2-ylmethyl)-3-(3,5-dimethoxy-4-methylphenyl)-3-hydroxylpropyl]-1H-pyrrol-3-yl}-2-methylacrylic acid.

[12] A pharmaceutical composition comprising the compound of formula (I) according to the above [1], a salt thereof, a solvate thereof or a prodrug thereof

[13] The pharmaceutical composition according to the above [12], which is an LPA receptor antagonist.

[14] The pharmaceutical composition according to the above [13], wherein the LPA receptor is EDG-2.

[15] The pharmaceutical composition according to the above [12], which is an agent for prevention and/or treatment for urinary system disease, carcinoma-associated disease, proliferative disease, inflammation/immune system disease, disease caused by secretory dysfunction, brain-related disease or chronic disease.

[16] A method for prevention and/or treatment of EDG-2 related diseases, which comprises administering to a mammal an effective amount of the compound of formula (I) according to the above [1], a salt thereof, a solvate thereof or a prodrug thereof

[17] Use of the compound of formula (I) according to the above [1], a salt thereof, a solvate thereof or a prodrug thereof for the manufacture of an agent for prevention and/or treatment of EDG-2 related diseases.

[18] A pharmaceutical composition comprising a combination of the compound of formula (I) according to the above [1], a salt thereof, a solvate thereof or a prodrug thereof with at least one agent selected from an LPA receptor antagonist, an α1 blocking agent, an anticholinergic agent, a 5α-reductase inhibitor and an anti-androgenic agent.

Examples of the "cyclic group" in the "cyclic group which may have a substituent(s)" represented by ring A or ring B and the "cyclic group" in the "cyclic group which may have a further substituent(s)" represented by ring D or ring E in formula (I) include a carbocyclic group or a heterocyclic group. The carbocyclic group includes, for example, a C3-15 monocyclic or polycyclic carbocyclic group, a polycyclic carbocyclic group having a spiro bond or a polycyclic bridged carbocyclic group. The C3-15 monocyclic or polycyclic carbocyclic group include a C3-15 monocyclic or polycyclic unsaturated carbocyclic group, and a partially saturated or fully saturated carbocyclic group, for example, cyclopropane, cyclobutane, cyclopentane, cyclohexane, cycloheptane, cyclooctane, cyclononane, cyclodecane, cycloundecane, cyclododecane, cyclotridodecane, cyclotetradecane, cyclopentadecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indan, naphthalene, dihydronaphthalene, teterahydronaphthalene, perhydronaphthalene, heptalene, perhydroheptalene, biphenylene, as-indacene, s-indacene, acenaphthylene, acenaphthene, fluorene, phenalene, phenanthrene, anthracene, spiro[4.4]nonane, spiro[4.5]decane, spiro[5.5]undecane, bicyclo[2.2.1]heptane, bicyclo[2.2.1]hept-2-ene, bicyclo[3.1.1]heptane, bicyclo[3.1.1]hept-2-ene, bicyclo[3.2.1]octane, bicyclo[2.2.2]octane, bicyclo[2.2.2]oct-2-ene, adamantane and noradamantane. Among these, the C3-15 monocyclic or polycyclic aromatic carbocyclic group includes, for example, benzene, azulene, indene, naphthalene, phenanthrene, anthracene ring. The heterocyclic group includes, for example, 3- to 15-membered monocyclic or polycyclic heterocyclic groups, polycyclic heterocyclic group having a spiro bond or polycyclic bridged heterocyclic group containing from 1 to 5 hetero atoms selected from an oxygen atom(s), a nitrogen atom(s) and a sulfur atom(s). 3- to 15-membered monocyclic or polycyclic heterocyclic groups containing from 1 to 5 hetero atoms selected from an oxygen atom(s), a nitrogen atom(s) and a sulfur atom(s) include the 3- to 15-membered monocyclic or polycyclic unsaturated heterocyclic group, and partially saturated or fully saturated heterocyclic groups containing from 1 to 5 hetero atoms selected from an oxygen atom(s), a nitrogen atom(s) and a sulfur atom(s), for example, pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzoxepine, benzoxazepine, benzoxadiazepine, benzothiepine, benzothiazepine, benzothiadiazepine, benzazepine, benzodiazepine, benzofurazan, benzothiadiazole, benzotriazole, carbazole, β-carboline, acridine, phenazine, dibenzofuran, xanthene, dibenzothiophene, phenothiazine, phenoxazine, phenoxathiin, thianthrene, phenanthridine, phenanthroline, perimidine, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzoxazepine, dihydrocarbazole, tetrahydrocarbazole, perhydrocarbazole, dihydroacridine, tetrahydroacridine, perhydroacridine, dihydrodibenzofuran, dihydrodibenzothiophene, tetrahydrodibenzofuran, tetrahydrodibenzothiophene, perhydrodibenzofuran, perhydrodibenzothiophene, dioxolane, dioxane, dithiolane, dithiane, dioxaindan, benzodioxane, chroman, benzodithiolane and benzodithiane ring. The polycyclic heterocyclic group having a spiro bond includes, for example, azaspiro[4.4]nonane, azaspiro[4.5]decane, azaspiro[5.5]undecane ring, etc. The polycyclic bridged heterocyclic group includes, for example, azabicyclo[2.2.1]heptane, azabicyclo[3.1.1]heptane, azabicyclo[3.2.1]octane, azabicyclo[2.2.2]octane ring, etc. Among these, the 3- to 15-membered monocyclic or polycyclic aromatic heterocyclic group containing from 1 to 5 hetero atoms selected from an oxygen atom(s), a nitrogen atom(s) and a sulfur atom(s) includes, for example, pyrrole, imidazole, triazole, tetrazole, pyrazole, pyridine, pyrazine, pyrimidine, pyridazine, furan, thiophene, oxazole, isoxazole, thiazole, isothiazole, furazan, oxadiazole, thiadiazole, indole, isoindole, benzofuran, isobenzofuran, benzothiophene, isobenzothiophene, indazole, quinoline, isoquinoline, purine, phthalazine, pteridine, naphthyridine, quinoxaline, quinazoline, cinnoline, benzoxazole, benzothiazole, benzimidazole, benzofurazan, benzothiadiazole, benzotriazole, carbazole, β-carboline, acridine, phenazine, dibenzofuran, dibenzothiophene, phenanthridine, phenanthroline, and perimidine ring. Examples of the "substituent" in the "aliphatic hydrocarbon group which may be substituted" represented by ring A or ring B or "cyclic group which may have a substituent(s)" represented by ring D or ring E include (a) alkyl which may be substituted, (b) alkenyl which may be substituted, (c) alkynyl which may be substituted, (d) a carbocyclic group which may have a substituent(s), (e) a heterocyclic group which may have a substituent(s), (f) hydroxyl which may be substituted, (g) mercapto which may be substituted, (h) amino which may be substituted, (i) carbamoyl which may be substituted, (j) sulfamoyl which may be substituted, (k) carboxyl, (l) alkoxycarbonyl (e.g., C1-6 alkoxycarbonyl, such as methoxycarbonyl, ethoxycarbonyl or tert-butoxycarbonyl, etc.), (m) sulfo, (n) sulfino, (o) phosphono, (p) nitro, (q) oxo, (r) thioxo, (s) cyano, (t) amidino, (u) imino, (v) dihydroxyboryl, (w) a halogen atom (fluorine, chlorine, bromine or iodine), (x) alkylsulfinyl (e.g., C1-6 alkylsulfinyl, such as methylsulfinyl or ethylsulfinyl, etc.), (y) arylsulfinyl (e.g., C6-10 arylsulfinyl, such as phenylsulfinyl, etc.), (z) alkylsulfonyl (e.g., C1-6 alkylsulfonyl, such as methylsulfonyl or ethylsulfonyl, etc.), (aa) arylsulfonyl (e.g., C6-10 arylsulfonyl, such as phenylsulfonyl, etc.), (bb) acyl (e.g., C1-6 alkanoyl, such as formyl, acetyl, propanoyl or pivaloyl, e.g., C6-10 arylcarbonyl, such as benzoyl, etc.) and the like, and 1 to 5 of these optional substituents may be substituted at replaceable positions. Examples of the "alkyl" in the "alkyl which may be substituted" as the substituent include straight chain or branched C1-10 alkyl and the like, such as methyl, ethyl, propyl, isopropyl, butyl, isobutyl, sec-butyl, tert-butyl, pentyl, isopentyl, neopentyl, hexyl, heptyl, octyl, nonyl and decyl. In this case, examples of the substituent of alkyl include hydroxyl, amino, carboxyl, nitro, mono- or di-C1-6 alkylamino (e.g., methylamino, ethylamino, propylamine, dimethylamino, diethylamino, etc.), C1-6 alkoxy (e.g., methoxy, ethoxy, propoxy, hexyloxy, etc.), C1-6 alkylcarbonyloxy (e.g., acetoxy, ethylcarbonyloxy, etc.), carbocyclic group which has the same meaning as the carboocyclic group in the "cyclic group" of the above-described "cyclic group which may have a substituent(s)", heterocyclic group which has the same meaning as the heterocyclic group in the "cyclic group" of the above-described "cyclic group which may have a substituent(s)", halogen atom (fluorine, chlorine, bromine or iodine) and the like, and 1 to 4 of these optional substituents may be substituted at replaceable positions. Examples of the "alkenyl" in the "alkenyl which may be substituted" as the substituent include straight chain or branched C2-10 alkenyl and the like, such as ethenyl, propenyl, butenyl, butadienyl, pentenyl, pentadienyl, hexenyl, hexadienyl, heptenyl, heptadienyl, octenyl, octadienyl, nonenyl, nonadienyl, decenyl and decadienyl. In this case, the substituent of alkenyl has the same meaning as the substituent in the above-described "alkyl which may be substituted". Examples of the "alkynyl" in the "alkynyl which may be substituted" as the substituent include straight chain or branched C2-10 alkynyl and the like, such as ethynyl, propynyl, butynyl, butadiynyl, pentynyl, pentadiynyl, hexynyl, hexadiynyl, heptynyl, heptadiynyl, octynyl, octadiynyl, nonynyl, nonadiynyl, decynyl and decadiynyl. In this case, the substituent of alkynyl has the same meaning as the substituent in the above-described "alkyl which may be substituted". The carbocyclic group in the "carbocyclic group which may have a substituent(s)" as the substituent has the same meaning as the carbocyclic group in the "cyclic group" of the above-described "cyclic group which may have a substituent(s)". In this case, examples of the substituent of the carbocyclic group include straight chain or branched C1-10 alkyl (the same meaning as the alkyl in the above-described "alkyl which may be substituted"), straight chain or branched C2-10 alkenyl (the same meaning as the alkenyl in the above-described "alkenyl which may be substituted"), straight chain or branched C2-10 alkynyl (the same meaning as the alkynyl in the above-described "alkynyl which may be substituted"), hydroxyl, C1-6 alkoxy (e.g., methoxy, ethoxy, propoxy, isopropoxy, butoxy, isobutyloxy, tert-butoxy, pentyloxy, hexyloxy, etc.), mercapto, C1-6 alkylthio (e.g., methylthio, ethylthio, propylthio, isopropylthio, butylthio, isobutylthio, tert-butylthio, pentylthio, hexylthio, etc.), amino, mono- or di-C1-6 alkylamino (e.g., methylamino, ethylamino, propylamino, isopropylamino, butylamino, isobutylamino, tert-butylamino, pentylamino, hexylamino, dimethylamino, diethylamino, dipropylamine, N-methyl-N-ethylamino, etc.), halogen atom (the same meaning as described above), cyano, nitro, trifluoromethyl, trifluoromethoxy and the like, and 1 to 5 of these optional substituents may be substituted at replaceable positions. The heterocyclic group in the "heterocyclic group which may have a substituent(s)" as the substituent has the same meaning as the heterocyclic group in the "cyclic group" of the above-described "cyclic group which may have a substituent(s)". In this case, the substituent of the heterocyclic group has the same meaning as the substituent of the above-described "carbocyclic group which may have a substituent(s)". Examples of the "substituent" of the "hydroxyl which may be substituted", "mercapto which may be substituted" and "amino which may be substituted" as the substituent include (i) alkyl which may be substituted (the same meaning as described above), (ii) alkenyl which may be substituted (the same meaning as described above), (iii) alkynyl which may be substituted (the same meaning as described above), (iv) a carbocyclic group which may have a substituent(s) (the same meaning as described above), (v) a heterocyclic group which may have a substituent(s) (the same meaning as described above), (vi) acyl (e.g., C1-6 alkanoyl, such as formyl, acetyl, propanoyl, pivaloyl, butanoyl, pentanoyl or hexanoyl, an isomer group thereof, etc., e.g., C6-10 aromatic carbocyclic carbonyl, such as benzoyl, etc.), (vii) carbamoyl which may be substituted (the same meaning as described below), (viii) alkylsulfonyl (e.g., C1-6 alkylsulfonyl, such as methylsulfonyl or ethylsulfonyl, etc.), (ix) arylsulfonyl (e.g., C6-10 arylsulfonyl, such as phenylsulfonyl, etc.) and the like. Examples of the "carbamoyl which may be substituted" as the substituent include unsubstituted carbamoyl, N-mono-C1-6 alkylcarbamoyl (e.g., N-methylcarbamoyl, N-ethylcarbamoyl, N-propylcarbamoyl, N-isopropylcarbamoyl, N-butylcarbamoyl, N-isobutylcarbamoyl, N-(tert-butyl)carbamoyl, N-pentylcarbamoyl, N-hexylcarbamoyl, etc.), N-mono-C6-10 arylcarbamoyl such as N-phenylcarbamoyl, N,N-di-C1-6 alkylcarbamoyl (e.g., N,N-dimethylcarbamoyl, N,N-diethylcarbamoyl, N,N-dipropylcarbamoyl, N,N-dibutylcarbamoyl, N,N-dipentylcarbamoyl, N,N-dihexylcarbamoyl, N-methyl-N-ethylcarbamoyl, etc.), N-di-C6-10 arylcarbamoyl such as N,N-diphenylcarbamoyl, N—C6-10 aryl-N—C1-6 alkylcarbamoyl (e.g., N-phenyl-N-methylcarbamoyl, N-phenyl-N-ethylcarbamoyl, N-phenyl-N-propylcarbamoyl, N-phenyl-N-butylcarbamoyl, N-phenyl-N-pentylcarbamoyl, N-phenyl-N-hexylcarbamoyl, etc.) and the like. Examples of the "sulfamoyl which may be substituted" as the substituent include unsubstituted sulfamoyl, N-mono-C1-6 alkylsulfamoyl (e.g., N-methylsulfamoyl, N-ethylsulfamoyl, N-propylsulfamoyl, N-isopropylsulfamoyl, N-butylsulfamoyl, N-isobutylsulfamoyl, N-(tert-butyl)sulfamoyl, N-pentylsulfamoyl, N-hexylsulfamoyl, etc.), N-mono-C6-10 arylsulfamoyl such as N-phenylsulfamoyl, N,N-di-C1-6 alkylsulfamoyl (e.g., N,N-dimethylsulfamoyl, N,N-diethylsulfamoyl, N,N-dipropylsulfamoyl, N,N-dibutylsulfamoyl, N,N-dipentylsulfamoyl, N,N-dihexylsulfamoyl, N-methyl-N-ethylsulfamoyl, etc.), N-di-C6-10 arylsulfamoyl such as N,N-diphenylsulfamoyl, N—C6-10 aryl-N—C1-6 alkylsulfamoyl (e.g., N-phenyl-N-methylsulfamoyl, N-phenyl-N-ethylsulfamoyl, N-phenyl-N-propylsulfamoyl, N-phenyl-N-butylsulfamoyl, N-phenyl-N-pentylsulfamoyl, N-phenyl-N-hexylsulfamoyl, etc.) and the like.

The "spacer having from 1 to 8 atoms in its principle chain" represented by K, Q or M means a space formed by 1 to 8 continued atoms. In this case, the "number of atoms of the principal atoms" should be counted such that atoms of the principal chain becomes minimum. Examples of the "spacer having from 1 to 8 atoms in its principle chain" include C1-8 alkylene which may have a substituent(s) (e.g., methylene, ethylene, trimethylene, tetramethylene, pentamethylene, hexamethylene, heptamethylene, octamethylene, etc.), C2-8 alkenylene which may have a substituent(s) (e.g., ethenylene, propenylene, butenylene, butadienylene, pentenylene, pentadienylene, hexenylene, hexadienylene, heptenylene, heptadienylene, octenylene, octadienylene, etc.), C2-8 alkynylene which may have a substituent(s) (e.g., ethynylene, propynylene, butynylene, butadiynylene, pentynylene, pentadiynylene, hexynylene, hexadiynylene, heptynylene, heptadiynylene, octynylene, octadiynylene, etc.) and the like. In this case, the carbon atom of the C1-8 alkylene, C2-8 alkenylene and C2-8 alkynylene may be replaced with an oxygen atom, a sulfur atom which may be oxidized (S, SO, $SO_2$,) or a nitrogen atom which may be substituted [examples of the substituent include (i) alkyl which may be substituted (the same meaning as described above), (ii) a carbocyclic group which may have a substituent(s) (the same meaning as described above), (iii) a heterocyclic group which may have a substituent(s) (the same meaning as described above), (iv) acyl (the same meaning as described above) and the like]. In this case, examples of the "substituent" as the "C1-8 alkylene which may have a substituent(s)", "C2-8 alkenylene which may have a substituent(s)" and "C2-8 alkynylene which may have a substituent(s)" include alkyl which may be substituted (the same meaning as described above), halogen atom (fluorine, chlorine, bromine or iodine), hydroxyl which may be substituted (the same meaning as described above), amino which may be substituted (the same meaning as described above), oxo, imino which may be substituted (e.g., C1-6 alkylimino, hydroxyimino, C1-6 alkoxyimino, cyanoimino, etc.) and the like, and 1 to 3 of these optional substituents may be substituted at replaceable positions.

The "spacer having from 1 to 3 atoms in its principle chain" represented by L means a space formed by 1 to 3 continued atoms. In this case, the "number of atoms of the principal atoms" should be counted such that atoms of the principal chain becomes minimum. Examples of the "spacer having from 1 to 3 atoms in its principle chain" include C1-3 alkylene which may have a substituent(s) e.g., —$CH_2$—, —$(CH_2)_2$—, —$(CH_2)_3$—, etc.), —O—, —S—, —SO—, —$SO_2$—, —$NR^2$—, —$CONR^2$—, —$NR^2CO$—, —$SO_2NR^2$—, —$NR^2SO_2$—, —$NR^2CONR^3$— [In the formulae, $R^2$ and $R^3$ each independently represents hydrogen, an aliphatic hydrocarbon group which may be substituted, or a cyclic group which may have a substituent(s) (the same meaning as described above). The "aliphatic hydrcarbon group" in the "aliphatic hydrocarbon group which may be substituted" includes a "straight or branched aliphatic hydrocarbon group", and the "straight or branched aliphatic hydrocarbon group" includes "straight or branched alkyl, alkenyl or alkynyl". The "straight or branched alkyl" includes, for example, straight or branched C1-10 alkyl such as methyl, ethyl, propyl, isopropyl, butyl, isobutyl, sec-butyl, tert-butyl, pentyl, isopentyl, neopentyl, hexyl, heptyl, octyl, nonyl and decyl, and the like. The "straight or branched alkenyl" includes, for example, straight or branched C2-10 alkenyl such as ethenyl, propenyl, butenyl, butadienyl, pentenyl, pentadienyl, hexenyl, hexedienyl, heptenyl, heptadienyl, octenyl, octadienyl, nonenyl, nonadienyl, decenyl and decadienyl, and the like. The "straight or branched alkynyl" includes, for example, straight or branched C2-10 alkynyl, such as ethynyl, propynyl, butynyl, butadiynyl, pentynyl, pentadiynyl, hexynyl, hexadiynyl, heptynyl, heptadiynyl, octynyl, octadiynyl, nonynyl, nonadiynyl, decynyl and decadiynyl, and the like. The "substituent" in the "aliphatic hydrocarbon group which may be substituted" has the same meaning as the above-described "substituent" in the "cyclic group which may have a substituent(s)".] and the like. Herein, the substituent in the C1-3 alkylene includes, for example, halogen atom (fluorine, chlorine, bromine, iodine), hydroxy, amino, oxo and the like, and 1 to 3 of these optional substituents may be substituted at replaceable positions.

Examples of the "acidic group which may be protected" represented by Z include —COOR$^T$, —SO$_2$OR$^T$, —SO$_2$R$^T$, —NR$^T$SO$_2$OR$^1$, —PO(OH)$_2$, —PO(OR$^T$)(OR$^1$), —CONR$^T$R$^4$, —CONR$^T$SO$_2$OR$^1$, —CONR$^T$SO$_2$R$^1$, —CONR$^T$SO$_2$NR$^4$R$^5$, —CONR$^T$OR$^1$, —CONNR$^T$R$^4$, —CONR$^T$SO$_2$R$^1$ or —CONR$^T$SO$_2$NR$^4$R$^5$ (wherein R$^T$ represents a hydrogen atom, an apliphatic hydrocarbon group which may be substituted, or a cyclic group which may have a substituent(s) (the same meaning as described above); R$^1$ represents an aliphatic hydrocarbon group which may be substituted or a cyclic group which may have a substituent(s); and R$^4$ and R$^5$ each independently represents a hydrogen atom, an aliphatic hydrocarbon group which may be substituted, or a cyclic group which may have a substituent(s) (the same meaning as described above)), —CONR$^{11}$CR$^{12}$R$^{13}$COOR$^{1T}$ (wherein —NR$^{11}$CR$^{12}$R$^{13}$CO— represents an amino acid residue, such as glycine, alanine, valine, leucine, isoleucine, glutamic acid, glutamine, aspartic acid, asparagine, lysine, arginine, histidine, tyrosine, serine, methionine, cysteine, proline, threonine, tryptophane, or phenylalanine residue), phenol (—C$_6$H$_4$OH) which may have a substituent(s) or various types of Brønsted acid such as a nitrogen-containing ring residue which may have a substituent(s) and has hydrogen from which can be removed as a proton.

Examples of the "acidic group" in the "acidic group which may be protected" represented by Z include —COOH, —SO$_2$OH, —SO$_2$H, —NHSO$_2$OR$^1$, —PO(OH)$_2$, —PO(OH)(OR$^1$), —CONHR$^4$, —CONHSO$_2$OR$^1$, —CONHSO$_2$R$^1$, —CONHSO$_2$NR$^4$R$^5$, —CONHOR$^1$, —CONNHR$^4$, —CONHSO$_2$R$^1$, —CONHSO$_2$NR$^4$R$^5$ (the same meaning as described above), phenol (—C$_6$H$_4$OH) which may have a substituent(s) or various types of Brønsted acid such as a nitrogen-containing ring residue having hydrogen from which can be removed as a proton.

The "Brønsted acid" means a substance which gives hydrogen ion to other substance. Examples of the "nitrogen-containing ring residue having hydrogen from which can be removed as a proton" include:

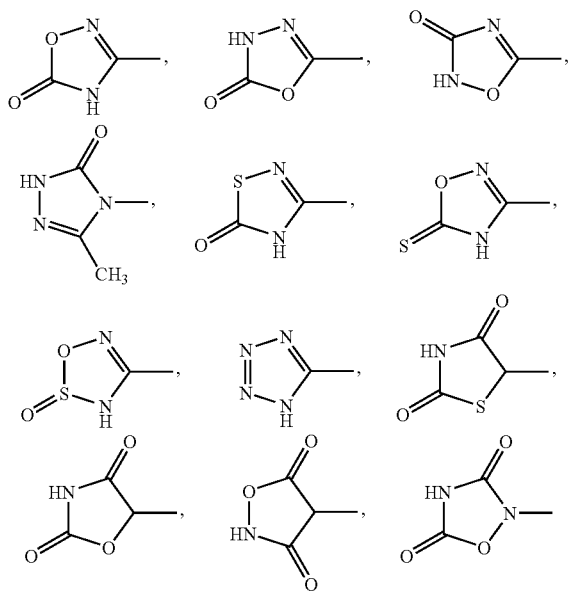

and the like.

Unless otherwise specifically mentioned, all isomers are included in the present invention. For example, alkyl, alkenyl, alkynyl, alkoxy, alkylthio, alkylene, alkenylene and alkynylene include straight chain and branched ones. Moreover, all of isomers due to double bond, ring and fused ring (E-, Z-, cis- and trans-forms), isomers due to the presence of asymmetric carbon(s), etc. (R- and S-forms, α- and β-configuration, enantiomer and diastereomer), optically active substances having optical rotation (D-, L-, d- and l-forms), polar compound by chromatographic separation (more polar compound and less polar compound), equilibrium compounds, rotational isomers, a mixture thereof in any proportion and a racemic mixture are included in the present invention.

In the present invention, as is apparent to one skilled in the art, unless otherwise indicated, the symbol ⋰ shows that the bond is on the other side of paper (α-configuration), the symbol ⁄ shows that the bond is in front of paper (β-configuration), and the symbol ⁄ shows that the bond is a mixture of α-configuration and β- configuration.

The salt of the compound of formula (I) includes all of salts which are pharmaceutically acceptable. With regard to the pharmaceutically acceptable salts, those which are low-toxic and soluble in water are preferred. Examples of appropriate salts are salt with alkaline metal (such as potassium, sodium and lithium), salt with alkaline earth metal (such as calcium and magnesium), ammonium salt (such as tetramethylammonium salt and tetrabutylammonium salt), salt with organic amine (such as triethylamine, methylamine, dimethylamine, cyclopentylamine, benzylamine, phenethylamine, piperidine, monoethanolamine, diethanolamine, tris(hydroxymethyl)methylamine, lysine, arginine and N-methyl-D-glucamine) and acid addition salt [such as inorganic acid salt (e.g., hydrochloride, hydrobromide, hydroiodide, sulfate, phosphate and nitrate) and organic acid salt (e.g., acetate, trifluoroacetate, lactate, tartrate, oxalate, fumarate, maleate, benzoate, citrate, methanesulfonate, ethanesulfonate, benzenesulfonate, toluenesulfonate, isethionate, glucuronate and gluconate), etc.]. The salt of the compound of the present invention also includes solvates and also solvates with the above-mentioned alkaline (earth) metal salt, ammonium salt, organic amine salt and acid addition salt. The solvate is preferably non-toxic and water-soluble. Examples of an appropriate solvate are solvates with water and with alcoholic solvent (such as ethanol). The compounds of the present invention are converted to pharmaceutically acceptable salts by known methods.

Additionally, the salt includes a quaternary ammonium salt thereof. A quaternary ammonium salt means a salt of a compound of formula (I) which nitrogen is quaternarized by R$^0$.

R$^0$ represents C1-8 alkyl, or C1-8 alkyl substituted with phenyl.

The compounds of the present invention can be converted to N-oxide by arbitrary methods. N-oxide means a compound of formula (I) of which nitrogen is oxidized.

A prodrug of the compound of formula (I) means a compound which is converted to the compound of formula (I) by reaction with an enzyme, gastric acid or the like in the living body. For example, with regard to a prodrug of the compound of formula (I), when the compound of formula (I) has an amino group, compounds in which the amino group is, for example, acylated, alkylated or phosphorylated (e.g., compounds in which the amino group of the compound of formula (I) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, acetoxymethylated, tert-butylated, etc.); when the compound of formula (I) has a hydroxyl group, compounds where the hydroxyl group is, for example, acylated, alkylated, phosphorylated or borated (e.g., compounds in which the hydroxyl group of the compound of formula (I) is acetylated, palmitoylated, propanoylated, pivaloylated, succinylated, fumarylated, alanylated or dimethylaminomethylcarbonylated); and that the carboxyl group of the compound of formula (I) is, for example, esterified or amidated (e.g., compounds in which the carboxyl group of the compound of formula (I) is made into ethyl ester, phenyl ester, phenylethyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester, cyclohexyloxycarbonylethyl ester or methylamide). Those compounds may be produced by a known method per se. The prodrug of the compound of formula (I) may be either a hydrate or a non-hydrate. A prodrug of the compound of formula (I) may also be a compound which is converted to the compound of formula (I) under physiologic condition as described in "*Iyakuhin no kaihatsu*, Vol. 7 (Bunshi-sekkei), pp. 163-198 (Hirokawa-Shoten), 1990". And the compound of formula (I) may also be labeled by a radio isotope (such as $^3$H, $^{14}$C, $^{35}$S, $^{125}$I, etc,).

In formula (I), ring A is preferably, for example, a C3-15 monocyclic or polycyclic carbocyclic ring which may have a substituent(s), a 3- to 15-membered monocyclic or polycyclic heterocyclic ring containing from 1 to 5 hetero atom(s) selected from an oxygen atom(s), a nitrogen atom(s) and a sulfur atom(s), which may have a substituent(s), or the like; more preferably, for example, a C3-15 monocyclic or polycyclic aromatic carbocyclic ring which may have a substituent(s), a 3- to 15-membered monocyclic or polycyclic aromatic heterocyclic ring containing from 1 to 5 hetero atom(s) selected from an oxygen atom(s), a nitrogen atom(s) and a sulfur atom(s), which may have a substituent(s), or the like; still more preferably a C5-6 monocyclic aromatic carbocyclic ring which may have a substituent(s), a 5- or 6-membered monocyclic aromatic heterocyclic ring containing from 1 to 5 hetero atom(s) selected from an oxygen atom(s), a nitrogen atom(s) and a sulfur atom(s), which may have a substituent(s), or the like; and most preferably, for example, a benzene ring which may have a substituent(s), a pyridine ring which may have a substituent(s), a thiophene ring which may have a substituent(s), or the like. The substituent on ring A is preferably, for example, alkyl which may be substituted, a carbocyclic group which may have a substituent(s), a heterocyclic group which may have a substituent(s), hydroxy which may be substituted, mercapto which may be substituted, amino which may be substituted, sulfamoyl which may be substituted, carboxy, nitro, a halogen atom, alkylsulfonyl, acyl, or the like; more preferably, for example, alkyl which may be substituted, hydroxy which may be substituted, a halogen atom, acyl, or the like; and most preferably methyl, ethyl, a fluorine atom, a chlorine atom, methoxy, ethoxy, difluoromethoxy, hydroxy, acetyl, trifluoromethoxy, methylsulfonyl, acetylamino, methylsulfonylamino, 1-hydroxy-1-methylethyl, 1-propenyl, cyano, or the like. 1 to 5 of these optional substituents may be substituted at replaceable positions. Unsubstituted one and one having from 1 to 3 substituent(s) are preferred.

K is preferably a spacer having from 1 to 8 atoms in its principle chain (e.g., C1-8 alkylene which may have a substituent(s), C2-8 alkenylene which may have a substituent(s), etc.); more preferably, for example, a bond, a spacer having from 1 to 4 atoms in its principle chain (e.g., C1-4 alkylene which may have a substituent(s), C2-4 alkenylene which may have a substituent(s), etc.); and more preferably, for example, methylene, ethylene, propylene, butylene, ethenylene, propenylene, or the like, and the carbon atom herein may be replaced with an oxygen atom a sulfur atom which may be oxidized (S, SO, SO$_2$) or a nitrogen atom which may be substituted, and is preferably, for example, an oxygen atom, a sulfur atom which may be oxidized (S, SO, SO$_2$), or the like; and more preferably, for example, an oxygen atom, a sulfur atom, or the like. The substituent in K is preferably, for example, alkyl which may be substituted, a halogen atom, hydroxy which may be substituted, oxo, or the like; and more preferably, for example, methyl, a fluorine atom, hydroxy, oxo, or the like. 1 to 3 of these optional substituents may be substituted at replaceable positions. Unsubstituted one and one having 1 or 2 substituent(s) are preferred. K is most preferably, for example, unsubstituted methylene, ethylene, propylene, butylene, —(CH$_2$)$_2$—O—, or the like.

Ring B is preferably, for example, a C3-15 monocyclic or polycyclic aromatic carbocyclic ring which may be partially saturated and may have a substituent(s), a 3- to 15-membered monocyclic or polycyclic aromatic heterocyclic ring containing from 1 to 5 hetero atom(s) selected from an oxygen atom(s), a nitrogen atom(s) and a sulfur atom(s), which may be partially saturated and may have a substituent(s), or the like, such as a benzene ring which may have a substituent(s), a thiophene ring which may have a substituent(s), an indan ring which may have a substituent(s), a 1,3-benzodioxole ring which may have a substituent(s), a cyclopentane ring which may have a substituent(s), a cyclohexane ring which may have a substituent(s), a cycloheptane ring which may have a substituent(s), a bicyclo[4.3]nonane ring which may have a substituent(s), a dihydroindole ring which may have a substituent(s), or the like. The substituent on ring B is preferably alkyl which may be substituted, a carbocyclic ring which may have a substituent(s), hydroxy which may be substituted, nitro, a halogen atom, oxo or the like; is more preferably, for example, alkyl which may be substituted, a halogen atom, or the like; and most preferably, methyl, ethyl, propyl, a fluorine atom, a chlorine atom, methoxy, ethoxy, or the like. 1 to 3 of these optional substituents may be substituted at replaceable positions. Unsubstituted one and one having 1 or 2 substituent(s) are preferred.

Q is preferably a spacer having from 1 to 8 atoms in its principle chain (e.g., C1-8 alkylene which may have a substituent(s), C1-8 alkenylene which may have a substituent(s), etc.); more preferably a spacer having from 1 to 4 atoms in its principle chain (e.g., C1-4 alkylene which may have a substituent(s), C2-4 alkenylene which may have a substituent(s), etc.); and most preferably a spacer having 1 or 2 carbons in its principle chain (e.g., C1-2 alkylene which may have a substituent(s), etc.). Examples include methylene which may be substituted, ethylene which may be substituted, and the like. The carbon atom herein may be replaced with an oxygen atom, a sulfur atom which may be oxidized (S, SO, SO$_2$) or a nitrogen atom which may be substituted. Q is most preferably, for example, methylene, ethylene, —O—, —CH$_2$—O— or the like.

Ring D is preferably, for example, C3-15 monocyclic or polycyclic carbocyclic ring which may have a substituent(s), a 3- to 15-membered monocyclic or polycyclic heterocyclic ring containing from 1 to 5 hetero atom(s) selected from an oxygen atom(s), a nitrogen atom(s) and a sulfur atom(s), which may have a substituent(s), or the like; more preferably a C3-15 monocyclic or polycyclic aromatic ring which may have a substituent(s), a 3- to 15-membered monocyclic or polycyclic aromatic ring containing from 1 to 5 hetero atom(s) selected from an oxygen atom(s), a nitrogen atom(s) and a sulfur atom(s), which may have a substituent(s), or the like; and still more preferably, for example, a benzene ring which may have a substituent(s), a pyrrole ring which may have a substituent(s), an imidazole ring which may have a substituent(s), a pyrazole ring which may have a substituent(s), an oxazole ring which may have a substituent(s), a thiazole ring which may have a substituent(s), a thiophene ring which may have a substituent(s), an indole ring which may have a substituent(s), a triazole ring which may have a substituent(s), a tetrazole ring which may have a substituent(s), a piperidine ring which may have a substituent(s), a pyrrolidine ring which may have a substituent(s), or the like. Most preferred is a benzene, pyrrole, or pyrazole ring which may have a substituent(s). The substituent on ring D is preferably alkyl which may be substituted, hydroxy which may be substituted, carboxy, alkoxycarbonyl, a halogen atom, oxo, aminocarbonyl, N,N-dialkylaminocarbonyl, N-alkylaminocarbonyl, acyl, or the like; more preferably, for example, alkyl which may be substituted, a halogen atom, or the like; and most preferably methyl, a fluorine atom, a chlorine atom, methoxylcarbonyl, ethoxycarbonyl, aminocarbonyl, N-methylaminocarbonyl, N,N-dimethylaminocarbonyl, acetyl, or the like. 1 to 5 of these optional substituents may be substituted at replaceable positions. Unsubstituted one and one having 1 substituent are preferred.

L is preferably, for example, a bond, —$CH_2$—, —O—, —S—, —SO—, —$SO_2$— or —NH—; and more preferably a bond, —O— or —S—.

Ring E is preferably, for example, a C3-15 monocyclic or polycyclic carbocyclic ring which may have a substituent(s), a 3- to 15-membered monocyclic or polycyclic heterocyclic ring containing from 1 to 5 hetero atom(s) selected from an oxygen atom(s), a nitrogen atom(s) and/or a sulfur atom(s), which may have a substituent(s), or the like; more preferably a C3-15 monocyclic or polycyclic aromatic carbocyclic ring which may have a substituent, a 3- to 15-membered monocyclic or polycyclic aromatic heterocyclic ring containing from 1 to 5 hetero atom(s) selected from an oxygen atom(s), a nitrogen atom(s) and/or a sulfur atom(s), which may have a substituent(s), or the like; still more preferably, for example, a C5-6 monocyclic aromatic carbocyclic ring which may have a substituent(s), a 5- or 6-membered monocyclic aromatic heterocyclic ring containing from 1 to 5 hetero atom(s) selected from an oxygen atom(s), a nitrogen atom(s) and/or a sulfur atom(s), which may have a substituent(s), or the like; and most preferably, for example, a benzene ring which may have a substituent(s), or the like. The substituent on ring E is preferably alkyl which may be substituted, hydroxy which may be substituted, a halogen atom, or the like; and more preferably, for example, methyl, a chlorine atom, a fluorine atom, methoxy, ethoxy, or the like. 1 to 5 of these optional substituents may be substituted at replaceable positions. Unsubstituted one and one having 1 substituent are preferred.

t is preferably 0 or 1.

M is preferably, for example, a bond, C1-8 alkylene which may have a substituent(s), C2-8 alkenylene which may have a substituent(s), or the like; more preferably, for example, a bond, a spacer having from 1 to 4 atoms in its principle chain (e.g., C1-4 alkylene which may have a substituent(s), C2-4 alkenylene which may have a substituent(s), etc.); and still more preferably, for example, a bond, methylene, ethylene, propylene, ethenylene, or the like, and the substituent on M is preferably, for example, alkyl which may be substituted; and more preferably, for example, methyl. 1 to 3 of these optional substituents may be substituted at replaceable positions. Unsubstituted one and one having 1 or 2 substituent(s) are preferred. M is most preferably, for example, a bond, methylene, ethylene, ethenylene, dimethylmethylene, or the like.

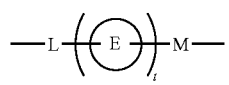

is preferably methylene which may be substituted, ethylene which may be substituted, propylene which may be substituted or ethenylene which may be substituted.

Z is preferably, for example, —COOH, —$CONHSO_2R^1$, tetrazolyl, or the like. $R^1$ in —$CONHSO_2R^1$ is preferably, for example, C1-8 alkyl which may be substituted, a carbocyclic ring group which may have a substituent(s), a heterocyclic ring group which may have a substituent(s), or the like.

Among the compounds of formula (I), a preferred compound is an optically active compound of formula (I-A):

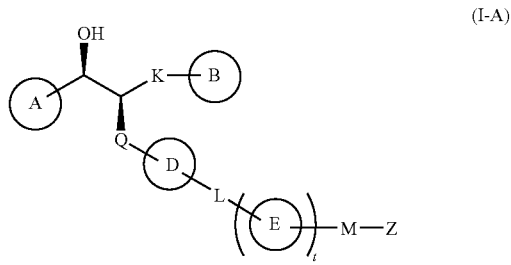

[wherein all symbols have the same meanings as described above] or formula (I-B):

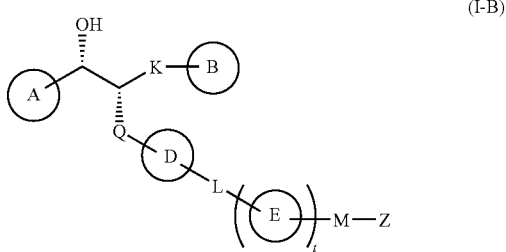

[wherein all symbols have the same meanings as described above] and particularly preferred is a compound of formula (I-A).

The purity optically active compound of formula (I-A) of the present invention may be 100%, and alternatively, it may be 50% or more, so long as the compound of formula (I-A) is included. Also, the purity optically active compound of formula (I-B) of the present invention may be 100%, and alternatively, it may be 50% or more, so long as the compound of formula (I-B) is included.

Among the compounds of formula (I), the compound is preferably, for example, a compound of formula (I-A-1):

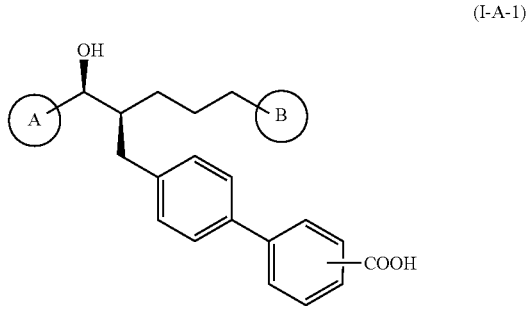

[wherein all symbols have the same meanings as described above]

a compound of formula (I-A-2):

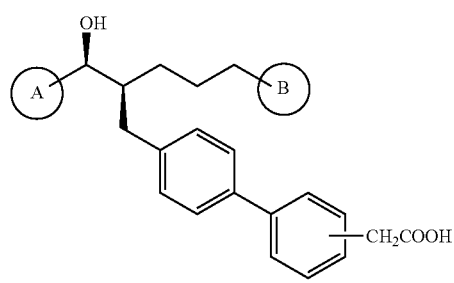

(I-A-2)

[wherein all symbols have the same meanings as described above]

a compound of formula (I-A-3):

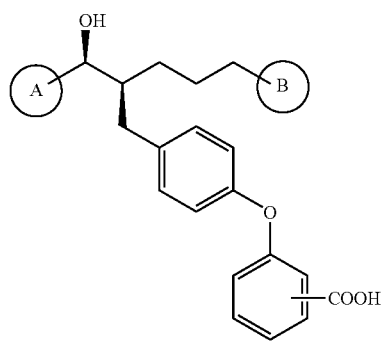

(I-A-3)

[wherein all symbols have the same meanings as described above]

a compound of formula (I-A-4):

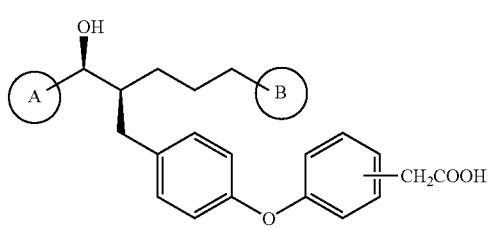

(I-A-4)

[wherein all symbols have the same meanings as described above]

a compound of formula (I-A-5):

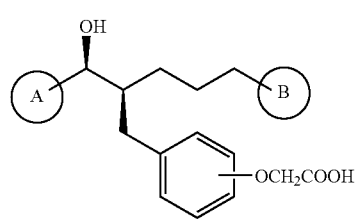

(I-A-5)

[wherein all symbols have the same meanings as described above]

a compound of formula (I-A-6):

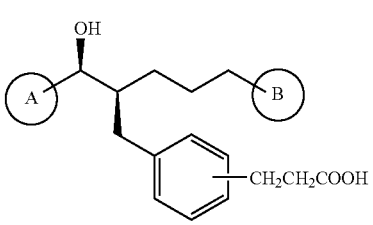

(I-A-6)

[wherein all symbols have the same meanings as described above]

a compound of formula (I-A-7):

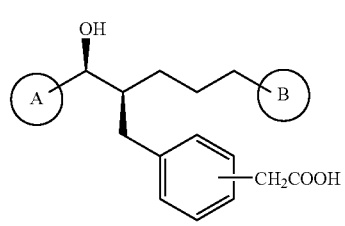

(I-A-7)

[wherein all symbols have the same meanings as described above]

a compound of formula (I-A-8):

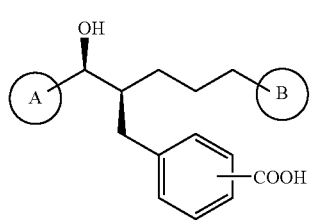

(I-A-8)

[wherein all symbols have the same meanings as described above]

a compound of formula (I-A-9):

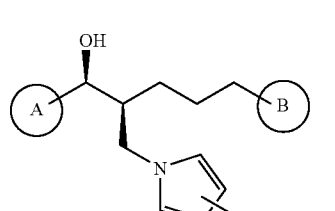

(I-A-9)

[wherein all symbols have the same meanings as described above]

a compound of formula (I-A-10):

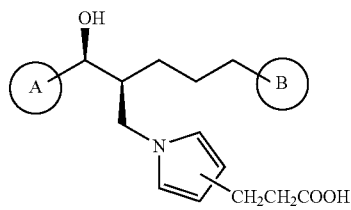
(I-A-10)

[wherein all symbols have the same meanings as described above]

a compound of formula (I-A-10-1):

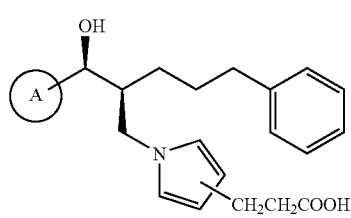
(I-A-10-1)

[wherein all symbols have the same meanings as described above]

a compound of formula (I-A-10-2):

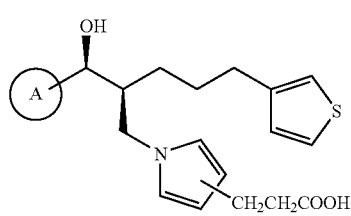
(I-A-10-2)

[wherein all symbols have the same meanings as described above]

a compound of formula (I-A-11):

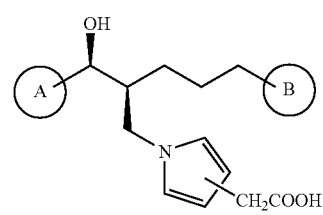
(I-A-11)

[wherein all symbols have the same meanings as described above]

a compound of formula (I-A-11-1):

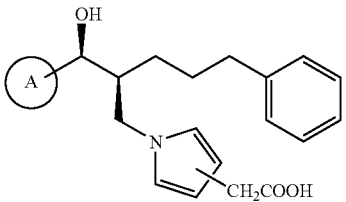
(I-A-11-1)

[wherein all symbols have the same meanings as described above]

a compound of formula (I-A-11-2):

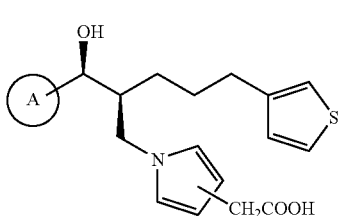
(I-A-11-2)

[wherein all symbols have the same meanings as described above]

a compound of formula (I-A-12):

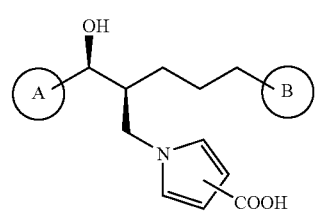
(I-A-12)

[wherein all symbols have the same meanings as described above]

a compound of formula (I-A-1 3-1):

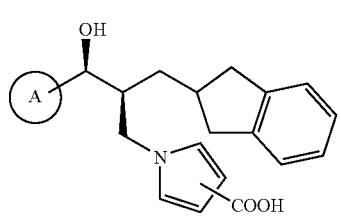
(I-A-13-1)

[wherein all symbols have the same meanings as described above]

a compound of formula (I-A-13-2):

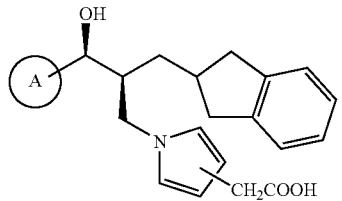
(I-A-13-2)

[wherein all symbols have the same meanings as described above]

a compound of formula (I-A-13-3):

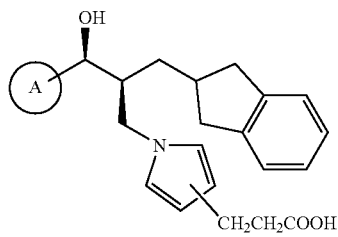
(I-A-13-3)

[wherein all symbols have the same meanings as described above]

a compound of formula (I-A-13-4):

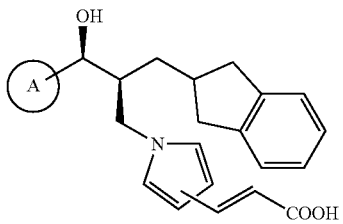
(I-A-13-4)

[wherein all symbols have the same meanings as described above]

a compound of formula (I-A-13-5):

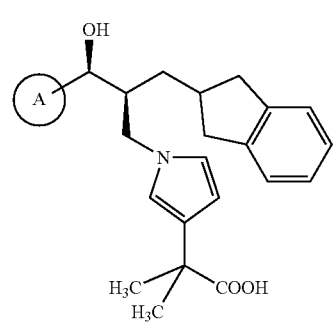
(I-A-13-5)

[wherein all symbols have the same meanings as described above]

a salt thereof, a solvate thereof, or a prodrug thereof.

Also, as other embodiments of the compounds of formula (I), the compound is preferably a compound of formula (I-A-14-1):

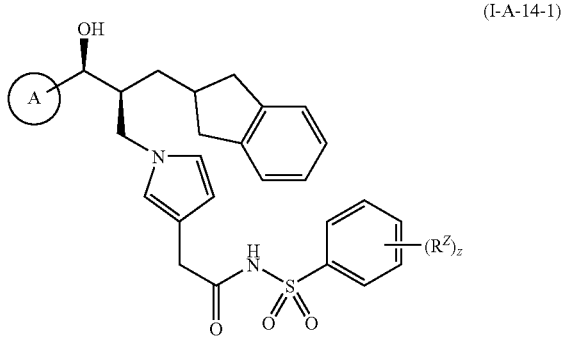
(I-A-14-1)

[wherein $R^Z$ represents a substituent on the cyclic group; z represents 0 or an integer of from 1 to 3; and other symbols have the same meanings as described above]

a compound of formula (I-A-14-2):

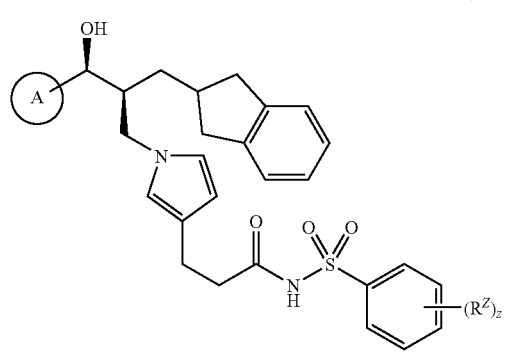
(I-A-14-2)

[wherein all symbols have the same meanings as described above]

a compound of formula (I-A-14-3):

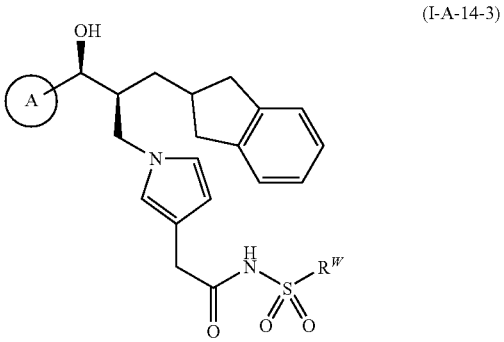
(I-A-14-3)

[wherein $R^W$ represents alkyl which may be substituted; and other symbols have the same meanings as described above]

a compound of formula (I-A-14-4):

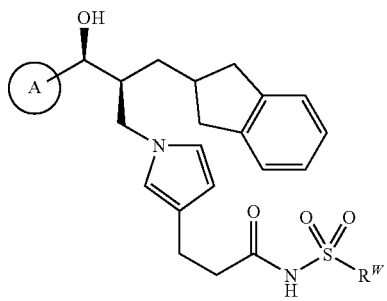

(I-A-14-4)

[wherein all symbols have the same meanings as described above]

a compound of formula (I-A-14-5):

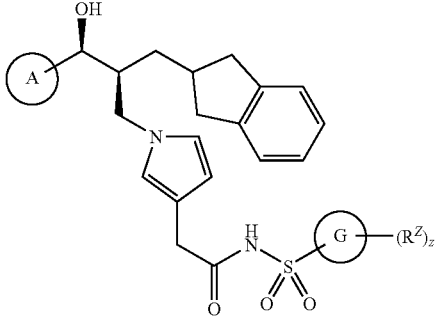

(I-A-14-5)

[wherein ring G represents a heterocyclic ring; and other symbols have the same meanings as described above]

a compound of formula (I-A-14-6)

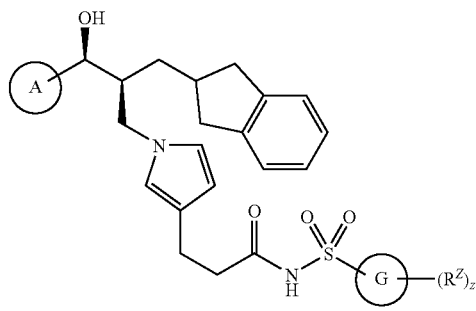

(I-A-14-6)

[wherein all symbols have the same meanings as described above]

a compound of formula (I-A-a)

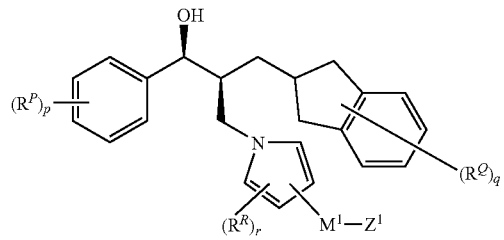

(I-A-a)

[wherein $R^P$, $R^Q$ and $R^R$ each independently represents a substituent; p, q and r each independently represents 0 or an integer of from 1 to 3; $M^1$ represents methylene which may be substituted, ethylene which may be substituted, propylene which may be substituted, or ethenylene which may be substituted; and $Z^1$ represents —COOH, —CONHSO$_2$R$^1$ (wherein $R^1$ has the same meaning as described above), or tetrazolyl. Also, plural $R^P$, $R^Q$ and $R^R$ are each independently the same or different]

a compound of formula (I-A-b)

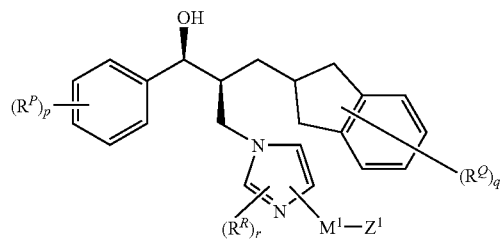

(I-A-b)

[wherein all symbols have the same meanings as described above]

a compound of formula (I-A-c)

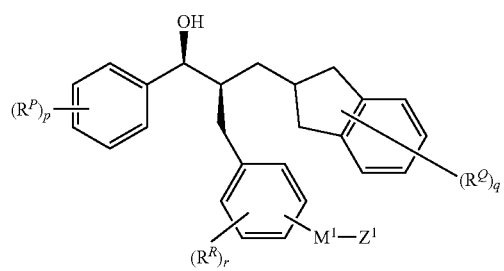

(I-A-c)

[wherein all symbols have the same meanings as described above]

a salt thereof, a solvate thereof, or a prodrug thereof.

Moreover, among the compounds of formula (I), compounds of the following (1) to (32), salts thereof, solvates thereof and prodrugs thereof are also preferred in addition to the compounds described in Examples.

(1) {4-[(2R)-2-[(S)-(3,5-dimethoxy-4-methylphenyl)(hydroxy)methyl]-4-(3-fluorophenoxy)butyl]phenyl}acetic acid, (2) (4-{(2R)-4-(3-chlorophenoxy)-2-[(S)-(3,5-dimethoxy-4-methylphenyl)(hydroxy)methyl]butyl}phenyl)acetic acid, (3) 4-(1-{(2S)-2-[(S)-(3,5-dimethoxy-4-methylphenyl)(hydroxy)methyl]-5-phenylpentyl}-1H-pyrazol-4-yl)butanoic acid, (4) (4-{(2S)-2-[(S)-(4-acetyl-3,5-dimethoxyphenyl)(hydroxy)methyl]-5-phenylpentyl}phenyl)acetic acid, (5) (3-{(2S)-2-[(S)-(3,5-dimethoxy-4-methylphenyl)(hydroxy)methyl]-5-phenylpentyl} isoxazol-5-yl)acetic acid, (6) 3-{1-[(2S)-2-[(S)-(3,5-dimethoxy-4-methylphenyl)(hydroxy)methyl]-5-(3-fluorophenyl)pentyl]-1H-pyrrol-3-yl}propanoic acid, (7) {4-[(2S)-2-[(S)-(3,5-dimethoxy-4-methylphenyl)(hydroxy)methyl]-5-(3-fluorophenyl)pentyl]phenyl}acetic acid, (8) {1-[(2S)-2-[(S)-(3,5-dimethoxy-4-methylphenyl)(hydroxy)methyl]-5-(3-fluorophenyl)pentyl]-1H-pyrrol-3-yl}acetic acid, (9) (1-{(2S)-5-(3-chlorophenyl)-2-[(S)-(3,5-dimethoxy-4-methylphenyl)(hydroxy)methyl]pentyl}-1H-pyrrol-3-yl)acetic acid,

(10) (4-{(2S)-5-(3-chlorophenyl)-2-[(S)-(3,5-dimethoxy-4-methylphenyl)(hydroxy)methyl]pentyl}phenyl)acetic acid,

(11) 4-(4-{(2S)-2-[(S)-hydroxy(3,4,5-trimethoxyphenyl)methyl]-5-phenylpentyl}phenyl)butanoic acid,

(12) (1-{(2S)-2-[(S)-hydroxy(3,4,5-trimethoxyphenyl)methyl]-5-phenylpentyl}-1H-pyrrol-3-yl)acetic acid,

(13) 3-(1-{(2S)-2-[(S)-(3,5-dimethoxy-4-methylphenyl)(hydroxy)methyl]-5-thien-3-ylpentyl}-1H-pyrrol-3-yl)propanoic acid,

(14) (1-{(2S)-2-[(S)-hydroxy(3,4,5-trimethoxyphenyl)methyl]-5-thien-3-ylpentyl}-1H-pyrrol-3-yl)acetic acid,

(15) (4-{(2S)-2-[(S)-hydroxy(3,4,5-trimethoxyphenyl)methyl]-5-thien-3-ylpentyl}phenyl)acetic acid,

(16) 3-(1-{(2S)-2-[(S)-hydroxy(3,4,5-trimethoxyphenyl)methyl]-5-phenylpentyl}-1H-pyrrol-3-yl)propanoic acid,

(17) 3-(1-{(2S)-2-[(S)-hydroxy(3,4,5-trimethoxyphenyl)methyl]-5-thien-3-ylpentyl}-1H-pyrrol-3-yl)propanoic acid,

(18) (4-{(2S)-2-[(S)-(4-bromo-3,5-dimethoxyphenyl)(hydroxy)methyl]-5-phenylpentyl}phenyl)acetic acid,

(19) (1-{(2S)-2-[(S)-(4-bromo-3,5-dimethoxyphenyl)(hydroxy)methyl]-5-phenylpentyl}-1H-pyrrol-3-yl)acetic acid,

(20) {1-[(2S)-2-[(S)-(4-chloro-3,5-dimethoxyphenyl)(hydroxy)methyl]-5-(3-fluorophenyl)pentyl]-1H-pyrrol-3-yl}acetic acid,

(21) (1-{(2S)-2-[(S)-(4-chloro-3,5-dimethoxyphenyl)(hydroxy)methyl]-5-phenylpentyl}-1H-pyrrol-3-yl)acetic acid,

(22) (1-{(2S)-2-[(S)-(4-chloro-3,5-dimethoxyphenyl)(hydroxy)methyl]-5-thien-3-ylpentyl}-1H-pyrrol-3-yl)acetic acid,

(23) 4-(1-{(2S)-2-[(S)-(3,5-dimethoxy-4-methylphenyl)(hydroxy)methyl]-5-phenylpentyl}-1H-pyrrol-3-yl)-4-oxobutanoic acid,

(24) (1S,2S)-1-(3,5-dimethoxy-4-methylphenyl)-5-phenyl-2-{[3-(1H-tetrazol-5-ylmethyl)-1H-pyrrol-1-yl]methyl}pentan-1-ol,

(25) 2-(1-{(2S)-2-[(S)-(3,5-dimethoxy-4-methylphenyl)(hydroxy)methyl]-5-phenylpentyl}-1H-pyrazol-4-yl)benzoic acid,

(26) (1S,2S)-1-(4-chloro-3,5-dimethoxyphenyl)-2-{[3-(1H-tetrazol-5-ylmethyl)-1H-pyrrol-1-yl]methyl}-5-thien-3-ylpentan-1-ol,

(27) (1S,2S)-1-(4-chloro-3,5-dimethoxyphenyl)-5-(3-fluorophenyl)-2-{[3-(1H-tetrazol-5-ylmethyl)-1H-pyrrol-1-yl]methyl}pentan-1-ol,

(28) (1-{(2S)-2-[(S)-(4-acetyl-3,5-dimethoxyphenyl)(hydroxy)methyl]-5-phenylpentyl}-1H-pyrrol-3-yl)acetic acid,

(29) [4-((2S)-2-{(S)-hydroxy[4-(hydroxymethyl)-3,5-dimethoxyphenyl]methyl}-5-phenylpentyl)phenyl]acetic acid,

(30) 3-(1-{(2S)-2-[(S)-(3,5-dimethoxy-4-methylphenyl)(hydroxy)methyl]-5-thien-2-ylpentyl}-1H-pyrrol-3-yl)propanoic acid,

(31) (1-{(2S)-2-[(S)-(3,5-dimethoxy-4-methylphenyl)(hydroxy)methyl]-5-thien-2-ylpentyl}-1H-pyrrol-3-yl)acetic acid, and

(32) 4-(1-{(2S)-2-[(S)-(3,5-dimethoxy-4-methylphenyl)(hydroxy)methyl]-5-thien-3-yipentyl}-1H-pyrrol-3-yl)-4-oxobutanoic acid.

Furthermore, among the compounds shown in Examples, particularly preferred are compound of the following (33) to (84), salts thereof, solvates thereof or prodrugs thereof.

(33) {1-[(2S,3S)-2-(2,3-dihydro-1H-inden-2-ylmethyl)-3-(3,5-dimethoxy-4-methylphenyl)-3-hydroxylpropyl]-1H-pyrazol-4-yl}acetic acid,

(34) 3-{1-[(2S,3S)-2-(2,3-dihydro-1H-inden-2-ylmethyl)-3-(3,5-dimethoxy-4-methylphenyl)-3-hydroxylpropyl]-1H-pyrazol-4-yl}propanoic acid,

(35) {1-[(2S,3S)-2-(2,3-dihydro-1H-inden-2-ylmethyl)-3-(3,5-dimethoxy-4-methylphenyl)-3-hydroxylpropyl]-1H-pyrrol-3-yl}acetic acid,

(36) (1-{(2S)-2-[(S)-(3,5-dimethoxy-4-methylphenyl)(hydroxy)methyl]-5-thien-3-ylpentyl}-1H-pyrrol-3-yl)acetic acid,

(37) {1-[(2S,3S)-2-(1,3-benzodioxol-2-ylmethyl)-3-(3,5-dimethoxy-4-methylphenyl)-3-hydroxylpropyl]-1H-pyrrol-3-yl}acetic acid,

(38) {1-[(2S,3S)-2-(2,3-dihydro-1H-inden-2-ylmethyl)-3-hydroxy-3-(3,4,5-trimethoxyphenyl)propyl]-1H-pyrrol-3-yl}acetic acid,

(39) {1-[(2S,3S)-3-(4-acetyl-3,5-dimethoxyphenyl)-2-(2,3-dihydro-1H-inden-2-ylmethyl)-3-hydroxylpropyl]-1H-pyrrol-3-yl}acetic acid,

(40) {1-[(2S,3S)-2-(2,3-dihydro-1H-inden-2-ylmethyl)-3-(4-ethyl-3,5-dimethoxyphenyl)-3-hydroxylpropyl]-1H-pyrrol-3-yl}acetic acid,

(41) 3-{1-[(2S,3S)-2-(2,3-dihydro-1H-inden-2-ylmethyl)-3-(3,5-dimethoxy-4-methylphenyl)-3-hydroxylpropyl]-1H-pyrrol-3-yl}propanoic acid,

(42) 3-{1-[(2S,3S)-2-(2,3-dihydro-1H-inden-2-ylmethyl)-3-hydroxy-3-(3,4,5-trimethoxyphenyl)propyl]-1H-pyrrol-3-yl}propanoic acid,

(43) {1-[(2S,3S)-2-(2,3-dihydro-1H-inden-2-ylmethyl)-3-(3,5-dimethoxyphenyl)-3-hydroxylpropyl]-1H-pyrrol-3-yl}acetic acid,

(44) 1-{(2S,3S)-2-(2,3-dihydro-1H-inden-2-ylmethyl)-3-hydroxy-3-[4-(1-hydroxy-1-methylethyl)-3,5-dimethoxyphenyl]propyl}-1H-pyrrol-3-yl)acetic acid,

(45) 3-{1-[(2S,3S)-3-(4-acetyl-3,5-dimethoxyphenyl)-2-(2,3-dihydro-1H-inden-2-ylmethyl)-3-hydroxylpropyl]-1H-pyrrol-3-yl}propanoic acid),

(46) (2E)-3-{1-[(2S,3S)-2-(2,3-dihydro-1H-inden-2-ylmethyl)-3-(4-ethyl-3,5-dimethoxyphenyl)-3-hydroxylpropyl]-1H-pyrrol-3-yl}acrylic acid,

(47) 3-{1-[(2S,3S)-2-(2,3-dihydro-1H-inden-2-ylmethyl)-3-(4-ethyl-3,5-dimethoxyphenyl)-3-hydroxylpropyl]-1H-pyrrol-3-yl}propanoic acid,

(48) 2-{1-[(2S,3S)-2(2,3-dihydro-1H-inden-2-ylmethyl)-3 (3,5-dimethoxy-4-methylphenyl)-3-hydroxylpropyl]-1H-pyrrol-3-yl}-N-(methylsulfonyl)acetamide,

(49) [1-[(2S,3S)-2-(2,3-dihydro-1H-inden-2-ylmethyl)-3-(3,5-dimethoxy-4-methylphenyl)-3-hydroxylpropyl]-4-(methoxylcarbonyl)-1H-pyrrol-3-yl]acetic acid,

(50) N-(3-{1-[(2S,3S)-2-(2,3-dihydro-1H-inden-2-ylmethyl)-3-(3,5-dimethoxy-4-methylphenyl)-3-hydroxylpropyl]-1H-pyrrol-3-yl}propanoyl)methanesulfonamide,

(51) N-(3-{1-[(2S,3S)-2-(2,3-dihydro-1H-inden-2-ylmethyl)-3-(3,5-dimethoxy-4-methylphenyl)-3-hydroxylpropyl]-1H-pyrrol-3-yl}propanoyl)benzenesulfonamide,

(52) N-({1-[(2S,3S)-2-(2,3-dihydro-1H-inden-2-ylmethyl)-3-(3,5-dimethoxy-4-methylphenyl)-3-hydroxylpropyl]-1H-pyrrol-3-yl}acetyl)-1,1,1-trifluoromethanesulfonamide,

(53) N-(3-{1-[(2S,3S)-2-(2,3-dihydro-1H-inden-2-ylmethyl)-3-(3,5-dimethoxy-4-methylphenyl)-3-hydroxylpropyl]-1H-pyrrol-3-yl}propanoyl)-4-fluorobenzenesulfonamide,

(54) 3-{1-[(2S,3S)-2-(2,3-dihydro-1H-inden-2-ylmethyl)-3-(3,5-dimethoxy-4-methylphenyl)-3-hydroxylpropyl]-1H-pyrrol-3-yl}-2-methylpropanoic acid,

(55) N-(3-{1-[(2S,3S)-2-(2,3-dihydro-1H-inden-2-ylmethyl)-3-(3,5-dimethoxy-4-methylphenyl)-3-hydroxylpropyl]-1H-pyrrol-3-yl}propanoyl)-2-methylbenzenesulfonamide,

(56) (2E)-3-{1-[(2S,3S)-2-(2,3-dihydro-1H-inden-2-ylmethyl)-3-(3,5-dimethoxy-4-methylphenyl)-3-hydroxylpropyl]-1H-pyrrol-3-yl}acrylic acid,

(57) N-(2-{1-[(2S,3S)-2-(2,3-dihydro-1H-inden-2-ylmethyl)-3-(4-ethyl-3,5-dimethoxyphenyl)-3-hydroxylpropyl]-1H-pyrrol-3-yl}acetyl)methanesulfonamide,

(58) N-(2-{1-[(2S,3S)-2-(2,3-dihydro-1H-inden-2-ylmethyl)-3-(4-ethyl-3,5-dimethoxyphenyl)-3-hydroxylpropyl]-1H-pyrrol-3-yl}acetyl)benzenesulfonamide,

(59) 2-{1-[(2S,3S)-2-(2,3-dihydro-1H-inden-2-ylmethyl)-3-(3,5-dimethoxy-4-methylphenyl)-3-hydroxylpropyl]-1H-pyrol-3-yl}-2-methylpropanoic acid,

(60) methyl2-{[(3-{1-[(2S,3S)-2-(2,3-dihydro-1H-inden-2-ylmethyl)-3-(3,5-dimethoxy-4-methylphenyl)-3-hydroxylpropyl]-1H-pyrrol-3-yl}propanoyl)amino]sulfonyl}benzoate,

(61) N-(3-{1-[(2S,3S)-2-(2,3-dihydro-1H-inden-2-ylmethyl)-3-(3,5-dimethoxy-4-methylphenyl)-3-hydroxylpropyl]-1H-pyrrol-3-yl}propanoyl)-2-thiophenesulfonamide,

(62) N-(2-{1-[(2S,3S)-2-(2,3-dihydro-1H-inden-2-ylmethyl)-3-(3,5-dimethoxy-4-methylphenyl)-3-hydroxylpropyl]-1H-pyrrol-3-yl}-2-methylpropanoyl)methanesulfonamide,

(63) N-({1-[(2S,3S)-2-(2,3-dihydro-1H-inden-2-ylmethyl)-3-(3,5-dimethoxy-4-methylphenyl)-3-hydroxylpropyl]-1H-pyrrol-3-yl}acetyl)-4-fluorobenzenesulfonamide,

(64) N'-(3-{1-[(2S,3S)-2-(2,3-dihydro-1H-inden-2-ylmethyl)-3-(3,5-dimethoxy-4-methylphenyl)-3-hydroxylpropyl]-1H-pyrrol-3-yl}propanoyl)-N,N-dimethylsulfamide,

(65) N-({1-[(2S,3S)-2-(2,3-dihydro-1H-inden-2-ylmethyl)-3-(3,5-dimethoxy-4-methylphenyl)-3-hydroxylpropyl]-1H-pyrrol-3-yl}acetyl)-2-methylbenzenesulfonamide,

(66) N-({1-[(2S,3S)-2-(2,3-dihydro-1H-inden-2-ylmethyl)-3-(3,5-dimethoxy-4-methylphenyl)-3-hydroxylpropyl]-1H-pyrrol-3-yl}acetyl)-2-(trifluoromethyl)benzenesulfonamide,

(67) N-({1-[(2S,3S)-2-(2,3-dihydro-1H-inden-2-ylmethyl)-3-(3,5-dimethoxy-4-methylphenyl)-3-hydroxylpropyl]-1H-pyrrol-3-yl}acetyl)-2-fluorobenzenesulfonamide,

(68) 2-chloro-N-({1-[(2S,3S)-2-(2,3-dihydro-1H-inden-2-ylmethyl)-3-(3,5-dimethoxy-4-methylphenyl)-3-hydroxylpropyl]-1H-pyrrol-3-yl}acetyl)benzenesulfonamide,

(69) N-({1-[(2S,3S)-2-(2,3-dihydro-1H-inden-2-ylmethyl)-3-(3,5-dimethoxy-4-methylphenyl)-3-hydroxylpropyl]-1H-pyrrol-3-yl}acetyl)-2,6-difluorobenzenesulfonamide,

(70) N-({1-[(2S,3S)-2-(2,3-dihydro-1H-inden-2-ylmethyl)-3-(3,5-dimethoxy-4-methylphenyl)-3-hydroxylpropyl]-1H-pyrrol-3-yl}acetyl)-3-fluorobenzenesulfonamide,

(71) 3-chloro-N-({1-[(2S,3S)-2-(2,3-dihydro-1H-inden-2-ylmethyl)-3-(3,5-dimethoxy-4-methylphenyl)-3-hydroxylpropyl]-1H-pyrrol-3-yl}acetyl)benzenesulfonamide,

(72) N-(2-{1-[(2S,3S)-2-(2,3-dihydro-1H-inden-2-ylmethyl)-3-(3,5-dimethoxy-4-methylphenyl)-3-hydroxylpropyl]-1H-pyrrol-3-yl}acetyl)-2-thiophenesulfonamide,

(73) 2-chloro-N-(3-{1-[(2S,3S)-2-(2,3-dihydro-1H-inden-2-ylmethyl)-3-(3,5-dimethoxy-4-methylphenyl)-3-hydroxylpropyl]-1H-pyrrol-3-yl}propanoyl)-6-methylbenzenesulfonamide,

(74) N-(3-{1-[(2S,3S)-2-(2,3-dihydro-1H-inden-2-ylmethyl)-3-(3,5-dimethoxy-4-methylphenyl)-3-hydroxylpropyl]-1H-pyrrol-3-yl}propanoyl)-2-methoxy-4-methylbenzenesulfonamide,

(75) N-(3-{1-[(2S,3S)-2-(2,3-dihydro-1H-inden-2-ylmethyl)-3-(3,5-dimethoxy-4-methylphenyl)-3-hydroxylpropyl]-1H-pyrrol-3-yl}propanoyl)-4-fluoro-2-methylbenzenesulfonamide,

(76) N-(3-{1-[(2S,3S)-2-(2,3-dihydro-1H-inden-2-ylmethyl)-3-(3,5-dimethoxy-4-methylphenyl)-3-hydroxylpropyl]-1H-pyrrol-3-yl}propanoyl)-5-methyl-2-furansulfonamide,

(77) N-({1-[(2S,3S)-2-(2,3-dihydro-1H-inden-2-ylmethyl)-3-(3,5-dimethoxy-4-methylphenyl)-3-hydroxylpropyl]-1H-pyrrol-3-yl}acetyl)-4-(trifluoromethyl)benzenesulfonamide,

(78) N-({1-[(2S,3S)-2-(2,3-dihydro-1H-inden-2-ylmethyl)-3-(3,5-dimethoxy-4-methylphenyl)-3-hydroxylpropyl]-1H-pyrrol-3-yl}acetyl)-4-methoxybenzenesulfonamide,

(79) N-(3-{1-[(2S,3S)-2-(2,3-dihydro-1H-inden-2-ylmethyl)-3-(3,5-dimethoxy-4-methylphenyl)-3-hydroxylpropyl]-1H-pyrrol-3-yl}propanoyl)-4-morpholinesulfonamide,

(80) N-(2-{1-[(2S,3S)-2-(2,3-dihydro-1H-inden-2-ylmethyl)-3-(3,5-dimethoxy-4-methylphenyl)-3-hydroxylpropyl]-1H-pyrrol-3-yl}acetyl)-4-morpholinesulfonamide,

(81) N-(3-{1-[(2S,3S)-2-(2,3-dihydro-1H-inden-2-ylmethyl)-3-(3,5-dimethoxy-4-methylphenyl)-3-hydroxylpropyl]-1H-pyrrol-3-yl}propanoyl)-4-methyl-1,3-thiazole-2-sulfonamide,

(82) 2-{1-[(2S,3S)-2-(2,3-dihydro-1H-inden-2-ylmethyl)-3-(4-ethyl-3,5-dimethoxyphenyl)-3-hydroxylpropyl]-1H-pyrrol-3-yl}-2-methylpropanoic acid,

(83) N-((2E)-3-{1-[(2S,3S)-2-(2,3-dihydro-1H-inden-2-ylmethyl)-3-(3,5-dimethoxy-4-methylphenyl)-3-hydroxylpropyl]-1H-pyrrol-3-yl}-2-propenoyl)methanesulfonamide, and

(84) (2E)-3-{1-[(2S,3S)-2-(2,3-dihydro-1H-inden-2-ylmethyl)-3-(3,5-dimethoxy-4-methylphenyl)-3-hydroxylpropyl]-1H-pyrrol-3-yl}-2-methylacrylic acid.

Additionally, in the present invention, compounds of formula (I) containing a combination of preferable groups and preferable rings described above are preferable.

Processes for the Preparation of the Compound of the Present Invention:

The compound of formula (I) of the present invention can be produced by the following processes, the processes shown in Examples, the processes according to them, or modified known processes (e.g., process described in *Comprehensive Organic Transformations: A Guide to Functional Group Preparations*, 2nd Edition (Richard C. Larock, John Wiley & Sons Inc, 1999)). In this connection, the starting material may be used as a salt in each of the following production processes. Such a salt includes those described above as the salts of formula (I).

The compound of formula (I) can be produced by subjecting a compound of formula (2):

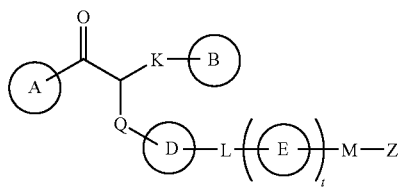

[wherein all symbols have the same meanings as described above] to a reduction of carbonyl.

The reduction of carbonyl is conventionally known and carried out, for example, by reaction at a temperature of from 0 to 100° C. in an organic solvent (methanol, tetrahydrofuran, a mixed solvent thereof, etc.) using a reducing agent (sodium borohydride, sodium triacetoxy-borohydride, sodium cyanoborohydride, tetrabutylammonium borohydride, etc.).

The compound of formula (I), at least one group of which represents a group having carboxyl, hydroxy, amino or mercapto, can be prepared by a deprotection of a compound protected by protecting group(s).

The protective group for carboxyl includes such as methyl, ethyl, allyl, t-butyl, trichloroethyl, benzyl (Bn), or phenacyl.

The protective group for hydroxyl includes such as methyl, trityl, methoxymethyl (MOM), 1-ethoxyethyl (EE), methoxyethoxymethyl (MEM), 2-tetrahydropyranyl (THP), trimethylsilyl (TMS), triethylsilyl (TES), t-butyldimethylsilyl (TBDMS), t-butyldiphenylsilyl (TBDPS), acetyl (Ac), pivaloyl, benzoyl, benzyl (Bn), p-methoxybenzyl, allyloxycarbonyl (Alloc) and 2,2,2-trichloroethoxycarbonyl (Troc) and the like.

The protective group of amino includes such as benzyloxycarbonyl, tert-butoxycarbonyl, allyloxycarbonyl (Alloc), 1-methyl-1-(4-biphenyl)ethoxycarbonyl (Bpoc), trifluoroacetyl, 9-fluorenylmethoxycarbonyl, benzyl (Bn), p-methoxybenzyl, benzyloxymethyl (BOM) and 2-(trimethylsilyl)ethoxymethyl (SEM) and the like.

The protective group of mercapto includes such as benzyl, methoxybenzyl, methoxymethyl (MOM), 2-tetrahydropyranyl (THP), diphenylmethyl and acetyl (Ac) and the like.

With regard to the protective group for carboxyl, hydroxyl, amino and mercapto, there is no particular limitation to the above ones so far as it is a group which is able to be easily and selectively removed. For example, a deprotection reaction may be carried out by a method mentioned in "T. W. Greene, *Protective Groups in Organic Synthesis*, John Wiley & Sons Inc, 1999".

Deprotection reaction of a protective group for carboxyl, hydroxyl, amino or mercapto is known and its examples are as follows: (1) a deprotecting reaction by alkali hydrolysis; (2) a deprotection reaction under acidic conditions; (3) a deprotection reaction by hydrogenolysis; (4) a deprotection reaction of silyl; (5) a deprotection reaction using metal; and (6) a deprotection reaction using an organic metal.

Those methods will be specifically illustrated as follows.

(1) A deprotection reaction by alkali hydrolysis is carried out, for example, at a temperature of 0 to 40° C. using a hydroxide of alkaline metal (sodium hydroxide, potassium hydroxide, lithium hydroxide, etc.), a hydroxide of alkaline earth metal (barium hydroxide, calcium hydroxide, etc.), a carbonate (sodium carbonate, potassium carbonate, etc.), an aqueous solution thereof or a mixture thereof in an organic solvent (methanol, tetrahydrofuran, 1,4-dioxane etc. alone, or a mixed solvent containing two or more solvents thereof at an optional ratio).

(2) A deprotection reaction under acidic conditions is carried out, for example, at a temperature of 0 to 100° C. in an organic acid (acetic acid, trifluoroacetic acid, methanesulfonic acid, p-toluenesulfonic acid, etc.), an inorganic acid (hydrochloric acid, sulfuric acid, etc.) or a mixture thereof (hydrogen bromide/acetic acid, etc.) in an organic solvent (dichloromethane, chloroform, 1,4-dioxane, ethyl acetate, anisole etc. alone, or a mixed solvent containing two or more solvents thereof at an optional ratio).

(3) A deprotection reaction by hydrogenolysis is carried out, for example, at a temperature of 0 to 200° C. in a hydrogen atmosphere of ordinary pressure or high pressure or in the presence of ammonium formate in the presence of a catalyst (palladium-carbon, palladium black, palladium hydroxide, platinum oxide, Raney nickel, etc.) in a solvent [an ether type (tetrahydrofuran, 1,4-dioxane, dimethoxyethane, diethyl ether, etc.), an alcohol type (methanol, ethanol, etc.), a benzene type (benzene, toluene, etc.), a ketone type (acetone, methyl ethyl ketone, etc.), a nitrile type (acetonitrile, etc.), an amide type (N,N-dimethylformamide, etc.), water, ethyl acetate, acetic acid or a mixed solvent comprising two or more thereof].

(4) A deprotection reaction of silyl is carried out, for example, at a temperature of 0 to 40° C. using tetrabutylammonium fluoride in an organic solvent miscible with water (tetrahydrofuran, acetonitrile etc. alone, or a mixed solvent containing two or more solvents thereof at an optional ratio).

(5) A deprotection reaction using a metal is carried out, for example, at a temperature of 0 to 40° C. with or without ultrasonic wave in the presence of powdery zinc in an acidic solvent (acetic acid, a buffer of pH 4.2 to 7.2 and a mixed solution of a solution thereof with an organic solvent such as tetrahydrofuran).

(6) A deprotection reaction using a metal complex is carried out, for example, at a temperature of 0 to 40° C. using a metal complex [tetrakistriphenylphosphine palladium (0), bis(triphenylphosphine) palladium (II) dichloride, palladium (II) acetate and tris(triphenylphosphine) rhodium (I) chloride, etc.] in the presence or absence of a phosphine agent (triphenyl phosphine, etc.) in the presence of a trap reagent (tributyltin hydride, triethylsilane, dimedone, morpholine, diethylamine, pyrrolidine, etc.), an organic acid (acetic acid, formic acid, 2-ethylhexanoic acid, etc.) and/or an organic acid salt (sodium 2-ethylhexanoate, potassium 2-ethylhexanoate, etc.) in an organic solvent (dichloromethane, N,N-dimethylformamide, tetrahydrofuran, ethyl acetate, acetonitrile, 1,4-dioxane, ethanol, etc.), water or a mixed solvent thereof.

Besides the above-mentioned method, for example, a deprotection reaction may be carried out by a method mentioned in T. W. Greene, *Protective Groups in Organic Synthesis*, John Wiley & Sons Inc (1999).

As persons skilled in the art can easily understand that the aimed compound of the present invention is able to be easily produced by using appropriate ones among those deprotection reactions.

The reaction can be followed by conversion to a desired non-toxic salt thereof by a known method, if necessary.

Among the compounds of formula (I), a compound wherein Q is —O— or —CH$_2$—O— (wherein ring D binds to the right of each group), namely, a compound of formula (I-1):

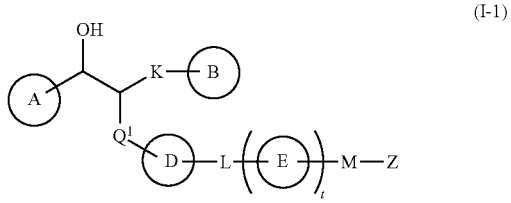

[wherein Q$^1$ represents —O— or —CH$_2$—O— (wherein ring D binds to the right of each group); and other symbols have the same meanings as described above.]

can be produced by subjecting a compound of formula (3):

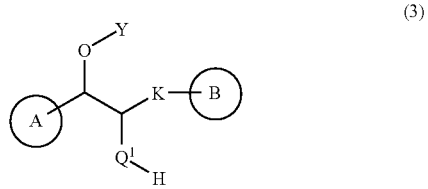

[wherein Y represents a protecting group of hydroxy (e.g., trimethylsilyl, t-butyldimethylsily, methoxymethyl, 1-ethoxyethyl, 2-tetrahydropyranyl, etc.), and other symbols have the same meanings as described above.]

and a compound of formula (4):

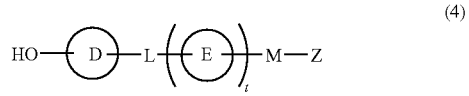

[wherein all symbols have the same meanings as described above]

to an etherification, followed by a deprotection of the protecting group of hydroxyl and, if necessary, a deprotection of the protecting group.

This etherification is conventionally known and carried out, for example, by reaction with a corresponding alcohol compound at a temperature of 0 to 60° C. in an organic solvent (dichloromethane, diethyl ether, tetrahydrofuran, acetonitrile, benzene, toluene, etc.) in the presence of an azo compound (diethyl azodicarboxylate (DEAD), diisopropyl azodicarboxylate, 1,1'-(azodicarbonyl)dipiperidine, 1,1'-azobis(N,N-dimethylformamide), etc.) and a phosphine compound (triphenylphosphine, tributylphosphine, trimethylphosphine, polymer-supported triphenylphosphine, etc.).

The deprotection of the protecting group of hydroxy and the deprotection of the protecting group can be carried out in the same manner as described above.

Among the compounds of formula (I), a compound wherein Q is C1-8 alkylene, C2-8 alkenylene or C2-8 alkynylene, and ring D represents an aromatic carbocyclic ring or an aromatic heterocyclic ring, namely, a compound of formula (I-2):

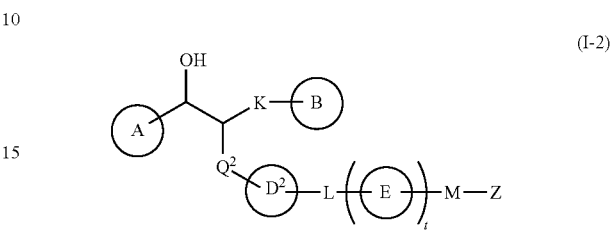

[wherein Q$^2$ represents C1-8 alkylene, C2-8 alkenylene or C2-8 alkynylene; ring D$^2$ represents an aromatic carbocyclic ring or an aromatic heterocyclic ring; and other symbols have the same meanings as described above]

can be produced by subjecting a compound of formula (5):

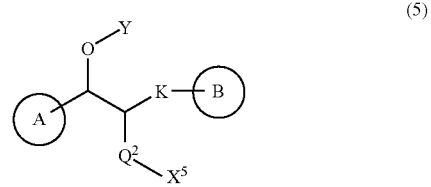

[wherein X$^5$ represents a halogen atom; and other symbols have the same meanings as described above]

and a compound of formula (6):

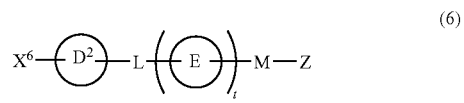

[wherein X$^6$ represents a halogen atom or trifluoromethanesulfonyloxy, and other symbols have the same meanings as described above.]

to a coupling reaction, followed by a deprotection of the protecting group of hydroxyl and, if necessary, a deprotection of the protecting group.

This coupling reaction is conventionally known and carried out, for example, by modifying the methods described in Ei-ichi Negishi, *J. Org Chem.*, 42, 1821 (1977), Shouquan Ho, *Organic Letters*, 5, 423 (2003), Paul Knochel, *Tetrahedron*, 54, 8275 (1998), Paul Knochel, *Chem. Rev.*, 93, 2117 (1993) and the like. For example, the compound of formula (5) is allowed to react at a temperature of –20 to 80° C. in an organic solvent (dimethylformamide, dimethylacetamide, tetrahydropyran, diethyl ether, acetonitril, benzene, toluene, a mixture thereof, etc.) in the presence of a metal (e.g., zinc, mangesium, etc.) and in the presence or absence of a metal activating agent (e.g., trimethylsilyl chloride, 1,2-dibromoethane, etc.), and then is allowed to react with a compound of formula (6) at –10 to 150° C. in the presence of a catalyst [e.g., tris(dibenzylideneacetone)dipalladium (0)-chloroform complex, tris(dibenzylideneacetone)dipalladium complex, palladium acetate, dichlorobis(acetonitrile)palladium, dichlorobis(benzonitrile)palladium, dichloro[1,1'-bis(diphenylphosphino)ferrocene]nickel, tetrakis(triphenylphosphine)palladium, etc.] and an organic phosphorus compound [e.g., triphenylphosphine, tris(2-methylphenyl)phosphine, tris(t-butyl)phosphine, 1,1'-bis(diphenylphosphino) ferrocene, tri-2-furylphosphine, etc.].

The deprotection of the protecting group of hydroxy and the deprotection of the protecting group can be carried out in the same manner as described above.

Among the compounds of formula (I), a compound wherein Q is C1-8 alkylene, and ring D is a heterocyclic ring bound to Q via a nitrogen atom, namely, a compound of formula (I-3):

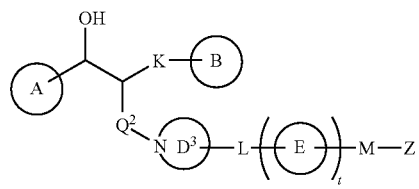
(I-3)

[wherein ring $D^3$ is a heterocyclic ring bound to Q via a nitrogen atom; and other symbols have the same meanings as described above]

can be produced by subjecting a compound of formula (7):

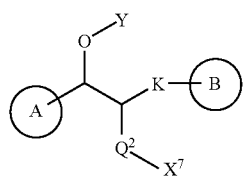
(7)

[wherein $X^7$ represents a leaving group (the leaving group represents a halogen atom, methanesulfonyloxy (OMs), p-toluenesulfonyloxy (OTs), trifluoromethanesulfonyloxy (OTf), etc.); and other symbols have the same meanings as described above]

and a compound of formula (8):

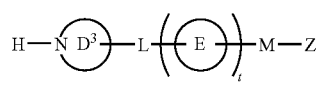
(8)

[wherein all symbols have the same meanings as described above]

to an N-alkylation, followed by a deprotection of the protecting group of hydroxyl and, if necessary, a deprotection of the protecting group.

This N-alkylation is conventionally known and carried out, for example, by reaction at a temperature of −78 to 40° C. in an organic solvent (tetrahydrofuran, diethyl ether, N,N-dimethylformamide, etc. alone, or a mixed solvent containing two or more solvents thereof at an optional ratio) in the presence of a base (lithium diisopropylamine (if necessary, in the presence of amine (N,N,N',N",N"-pentamethyldiethylenetriamine, N,N,N',N'-tetramethylethylenediamine, etc.)), sodium hydride, potassium carbonate, cesium carbonate, etc.).

The deprotection of the protecting group of hydroxy and the deprotection of the protecting group can be carried out in the same manner as described above.

Among the compounds of formula (I), a compound wherein Z is tetrazolyl, namely, a compound of formula (I-4):

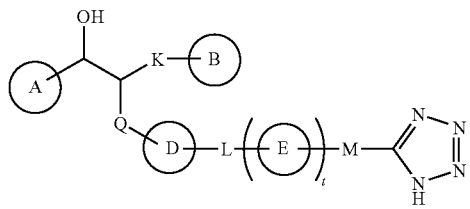
(I-4)

[wherein all symbols have the same meanings as described above]

can be produced by reacting a compound of formula (9):

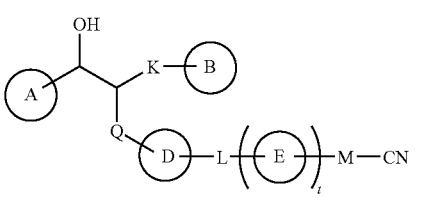
(9)

[wherein all symbols have the same meanings as described above]

with an azide compound, followed by, if necessary, a deprotection of the protecting group.

This reaction is conventionally known and carried out, for example, by reaction with an azide compound (e.g., sodium azide, lithium azide, trimethylsilylazide, trimethyltin azide, tributyltin azide, etc.) at a temperature of 20 to 150° C. in water or an organic solvent (benzene, toluene, xylene, N,N-dimethylformamide, tetrahydrofuran, 1,4-dioxane, isopropanol, etc.) alone, or a mixed solvent containing two or more solvents thereof at an optional ratio and in the presence or absence of an additive (e.g., zinc bromide, lithium chloride, ammonium chloride, acetic acid, trifluoroacetic acid, triethylamine, pyridine, etc.).

Among the compounds of formula (I), a compound wherein Z represents $CONHSO_2R^1$, namely, a compound of formula (I-5):

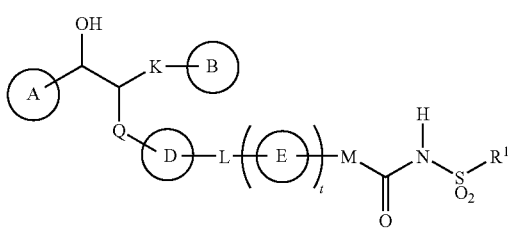
(I-5)

[wherein all symbols have the same meanings as described above]

can be produced by subjecting a compound of formula (10):

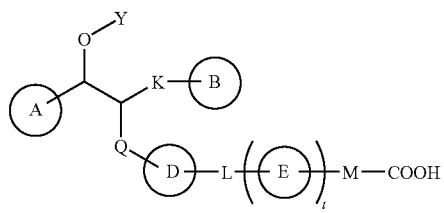
(10)

[wherein all symbols have the same meanings as described above]

and a compound of formula (11):

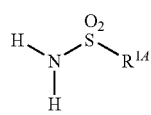
(11)

[wherein $R^{1A}$ has the same meaning as $R^1$, but, when protection is necessary, it may be protected.]

to an amidation, followed by a deprotection of the protecting group of hydroxyl and, if necessary, a deprotection of the protecting group.

The amidation is known and its examples are
(1) a process using an acid halide,
(2) a process using a mixed acid anhydride and
(3) a process using a condensing agent.

Such processes will be specifically illustrated as follows.
(1) A process using an acid halide is carried out, for example, in such a manner that carboxylic acid is allowed to react with an agent for producing an acid halide (such as oxalyl chloride, thionyl chloride, etc.) in an organic solvent (such as chloroform, dichloromethane, diethyl ether and tetrahydrofuran) or without solvent at −20° C. to refluxing temperature and the resulting acid halide is allowed to react with an amine in the presence of a base (such as pyridine, triethylamine, dimethylaniline, dimethylaminopyridine and diisopropylethylamine) in an inert organic solvent (such as chloroform, dichloromethane, diethyl ether and tetrahydrofuran) at a temperature of 0 to 40° C. It is also possible to conduct the reaction with an acid halide at 0 to 40° C. in an organic solvent (such as dioxane and tetrahydrofuran) using an aqueous solution of alkali (such as aqueous solution of sodium hydrogen carbonate or an aqueous solution of sodium hydroxide).
(2) A process using a mixed acid anhydride is carried out, for example, in such a manner that carboxylic acid is allowed to react with an acid halide (such as pivaloyl chloride, tosyl chloride or mesyl chloride) or with an acid derivative (such as ethyl chloroformate and isobutyl chloroformate) at 0 to 40° C. in an organic solvent (such as chloroform, dichloromethane, diethyl ether and tetrahydrofuran) or without a solvent in the presence of a base (such as pyridine, triethylamine, dimethylaniline, dimethylaminopyridine and diisopropylethylamine) and the resulting mixed acid anhydride is allowed to react with an amine at 0 to 40° C. in an organic solvent (such as chloroform, dichloromethane, diethyl ether and tetrahydrofuran).
(3) A process using a condensing agent is carried out, for example, in such a manner that carboxylic acid and an amine are allowed to react at 0 to 40° C. with or without 1-hydroxybenztriazole (HOBt) using a condensing agent (such as 1,3-dicyclohexylcarbodiimide (DCC), 1-ethyl-3-[3-(dimethylamino)propyl]carbodiimide (EDC), 1,1′-carbonyldiimidazole (CDI), 2-chloro-1-methylpyridinium iodide and 1-propanephosphonic acid cyclic anhydride (PPA)) in the presence or absence of a base (such as pyridine, triethylamine, dimethylanilin, dimethylaminopyridine and 1,8-diazabicyclo[5.4.0]-undec-7-ene) in an organic solvent (such as chloroform, dichloromethane, N,N-dimethylformamide, diethyl ether and tetrahydrofuran) or without a solvent.

It is preferred that all of the reactions (1), (2) and (3) are carried out in an atmosphere of inert gas (such as argon and nitrogen) under an anhydrous condition.

The compounds of formulae (2) to (11) using as the starting materials or reagents are known per se or can easily produced by known methods, such as *Comprehensive Organic Transformations: A Guide to Functional Group Preparations*, 2nd Edition (Richard C. Larock, John Wiley & Sons Inc (1999)) or methods shown Examples.

In each reaction in the present specification, as apparent to the skilled persons in the art, the reactions involving heating may be carried out using a water bath, an oil bath, a sand bath or a microwave.

In each reaction in the present specification, a solid-supported reagent which is supported on a high molecular polymer (e.g., polystyrene, polyacrylamide, polypropylene, polyethylene glycol, etc.) may be suitably used.

In each reaction in this description, the reaction product can be purified by general purification techniques, such as distillation under ordinary pressure or a reduced pressure, high performance liquid chromatography using silica gel or magnesium silicate, thin layer chromatography, ion exchange resin, scavenger resin, column chromatography, washing, recrystallization and the like. Purification may be carried out for each reaction or after completion of several reactions.

In the reaction using the polystyrene in the present specification, the reaction products can be purified by general purification means such as washing several times with solvent (N,N-dimethylformamide, dichloromethane, methanol, tetrahydrofuran, toluene, acetic acid/toluene, etc.).

Toxicity:

Toxicity of the compound of formula (I) of the present invention is sufficiently low and it was confirmed to be sufficiently safe to be used as pharmaceuticals.

Application to Pharmaceuticals:

Since the compound of formula (I) of the present invention is antagonistic to LPA receptors (especially EDG-2), they are believed to be useful for prevention and/or treatment of EDG-2 related diseases (e.g., urinary system disease, carcinoma-associated disease, proliferative disease, inflammation/immune system disease, disease caused by secretory dysfunction, brain-related disease, chronic disease, etc.).

For example, for urinary system disease, prostatic hypertrophy or neurogenic bladder dysfunction disease, and dysuria (micturation initiation delay, extension between on urination, urinary stream very small, intermission micturation, two steps of micturation, etc.), pollakiuria, night urination, urodynia, etc. are known as symptoms with a urinary system disease. Similar urologic symptoms are symptoms caused by cerebrovascular disorder, Parkinson disease, brain tumor, a multiple sclerosis, Shy-Drager symptom, spinal cord neoplasm, nucleous hernia, spinal canal stenosis, diabetes, etc.

(such as dysuria (micturation initiation delay, extension between on urination, urinary stream very small, intermission micturation, two steps of miction), pollakiuria, night urination, urodynia). Other example of urinary system disease include lower urinary tract symptom (for example, occlusion disease of lower urinary tract), inflammatory disease of lower urinary tract (such as infection), interstitial cystitis, polyuria and the like. And these diseases and symptoms are considered to be cured by LPA receptor antagonists.

For example, for carcinoma-associated disease, solid tumor, solid tumor metastasis, angiofibroma, myeloma, multiple myeloma, Kaposi's sarcoma, leucemia are given. In solid tumor, mammary cancer, lung cancer, gastric cancer, carcinoma oesophagi, large bowel cancer, colon rectal cancer, liver cancer, ovarian cancer, theca cell tumor, androblastoma, cervix cancer, endometrial carcinoma, prostate cancer, kidney cancer, carcinoma cutaneum, osteosarcoma, pancreas cancer, urinary tract carcinoma, thyroid cancer, and brain tumor such as glioblastoma and neuroblastoma are given. In addition, it is thought that carcinomatous infiltration transition is suppressed by LPA receptor antagonist.

For example, for proliferative disease, disorder with aberrant angiogenesis (for example, re-arctation, diabetic retinopathy, angiogenesis-related glaucoma, crystalline lens fiber multiplication symptom, thyroid gland hyperplasia (including Basedow's disease), lung inflammation, nephrotic syndrome and osteoporosis), artery obstruction, pulmonary fibrosis are given.

For example, for inflammation/immune system disease, psoriasis, nephropathy (for example, IgA nephropathy), nephritis by other inflammation/immunopathy, hepatitis, pneumonitis symptom are given.

For example, for disease caused by secretory dysfunction, secretion fault by autonomic nervous system anomaly is given, for example, for disease caused by secretory dysfunction by autonomic nervous system anomaly, Sjogren syndrome is given.

For example, for brain-/nervous-related disease, brain infarction, cerebral apoplexy, brain or peripheral neuropathy are given. Also, for nervous disease relating to pain, cancer pain, chronic pelvic pain syndrome, algesia, allodynia, etc. are given.

For example, for chronic disease, chronic asthma, glomerulonephritis, obesity, prostate hyperplasia, chronic prostatitis, diseases caused by arteriosclerosis process, rheumatism or atopic dermatitis, cirrhosis, fatty liver, chronic diarrhea, chronic constipation, etc. are given.

The compound of formula (I) of the present invention, a salt thereof, a solvate thereof, or a prodrug thereof may be administered as a combined preparation by combining with other pharmaceuticals for the purpose of
1) supplement and/or enhancing of prevention and/or treatment effect of the compound,
2) improvement in pharmacokinetics and absorption and reduction of dose of the compound, and/or
3) reduction of side effect of the compound.

The combined preparation of the compound of formula (I) of the present invention with other pharmaceuticals may be administered in a form of a compounded agent in which both components are compounded in a preparation or may be in a form in which they are administered by means of separate preparations. The case of administration by means of separate preparations includes a simultaneous administration and administrations with time difference. In the case of administrations with time difference, the compound of formula (I) of the present invention may be firstly administered followed by administering the other pharmaceutical or the other pharmaceutical may be administered firstly followed by administering the compound of formula (I) of the present invention. Methods for each of the administration are the same or different.

There is no particular limitation for the diseases showing prevention and/or treatment effect by the above-mentioned combined preparation, so far as it is a disease in which the prevention and/or treatment effect of the compound of present invention of formula (I) are supplemented and/or enhanced.

The other pharmaceutical for supplement and/or enhancing the prevention and/or treatment effect of the compound of formula (I) of the present invention for urinary system disease includes other urologic disease therapeutic agent such as other LPA receptor antagonist, (α1 blocking agent, anticholinergic agent, 5α-reductase inhibitor and/or anti-androgenic agent. But anticholinergic agent is used only by case without prostatic hypertrophy. It is mainly used by remedy of pollakiuria or anischuria of case without prostatic hypertrophy.

The other pharmaceutical for supplement and/or enhancing the prevention and/or treatment effect of the compound of formula (I) of the present invention for carcinoma disease region includes such as other carcinoma treatment of disease agent.

Examples of the other pharmaceutical preparations for supplement for and/or enhancing the preventive and/or treatment effect of the compound of formula (I) of the present invention on chronic asthma include steroids, $\beta_2$ adrenoreceptor stimulant, leukotriene receptor antagonist, thromboxane synthetase inhibitor, thromboxane $A_2$ receptor antagonist, mediator releasing inhibitor, antihistamines, xanthine derivatives, anticholinergic agent, cytokine inhibitor, prostaglandins, forskolin, phosphodiesterase inhibitor, elastase inhibitor, metalloproteinase inhibitor, expectorant, and antibiotic.

Examples of the other pharmaceutical preparations for supplement for and/or enhancing the preventive and/or treatment effect of the compound of formula (I) of the present invention on prostatic hypertrophy include anti-androgenic agent, α1 receptor blocking agent, and 5α-reductase inhibitor, etc.

Examples of the other pharmaceutical preparations for supplement for and/or enhancing the preventive and/or treatment effect of the compound of formula (I) of the present invention on disease caused by progress of arterial sclerosis include HMG-CoA reductase inhibitor, fibrate preparations, probucol preparations, anion-exchange resin, EPA preparations, nicotinic acid preparations, MTP (Microsomal Triglyceride Transfer Protein) inhibitor, PPAR agonist preparations, and other antihypercholesterolemic agent, etc.

Examples of the other pharmaceutical preparations for supplement for and/or enhancing the preventive and/or treatment effect of the compound of formula (I) of the present invention on rheumatism include nonsteroidal antiinflammatory drug, disease modifying anti-rheumatic drug (slow-acting anti-rheumatic drug), steroids, immunosuppressant agent, antiinflammatory enzyme preparations, chondroprotective agents, T-cell inhibitors, TNFα inhibitor (include protein preparation such as anti-TNFα antibody), prostaglandin synthase inhibitor, IL-6 inhibitor (include protein preparation such as anti-IL-6 receptor antibody), interferon gamma agonists, IL-1 inhibitor, prostaglandins, phosphodiesterase inhibitor, metalloproteinase inhibitor, etc.

Examples of the other pharmaceutical preparations for supplement for and/or enhancing the preventive and/or treatment effect of the compound of formula (I) of the present invention on atopic dermatitis include steroids, nonsteroidal antiinflammatory drug, immunosuppressant agent, prostaglandins, antiallergic agent, mediator releasing depressant, antihistamine drug, forskolin preparations, phosphodiesterase inhibitor, Decoy preparations such as NF-kB, cannabinoid-2 receptor stimulator, etc.

The other LPA receptor antagonist includes such as methyl3-({4-[4-({[1-(2-chlorophenyl)ethoxy]carbonyl}amino)-3-methyl-5-isoxazolyl]benzyl}sulfanyl)propanoate, etc.

The α1 blocking agent includes such as terazosin hydrochloride, Bunazosin Hydrochloride, urapidil, tamsulosin hydrochloride, doxazosin mesilate, prazosin hydrochloride, indolamine, naftopidil, alfuzosin hydrochloride and AIO-8507L, etc.

The anticholinergic agent includes such as oxybutinin hydrochloride, bethanechol chloride, propiverine hydrochloride, propantheline bromide, methylbenactyzium bromide, butylscopolamine bromide, tolterodine tartrate, trospium chloride, Z-338, UK-112166-04, KRP-197 (ONO-8025), darifenacin and YM-905 (solifenacin succinate), etc.

The 5α-reductase inhibitor includes such as finasteride and GI-998745, etc.

The anti-androgenic agent includes such as oxendolone, osaterone acetate and bicalutamide, etc.

The other carcinoma treatment of disease agent includes alkylating agent (such as nitrogen mustard N-oxide hydrochloride, cyclophosphamide, ifosfamide, melphalan, thiotepa, carboquone, busulfan), nitrosourea derivative (such as nimustine hydrochloride, ranimustine), an antimetabolite (such as methotrexate, mercaptopurine, 6-mercapropurinboside, fluorouracil, tegafur, UFT, carmofur, doxifluridine, cytarabine, enocitabine), anticancer antibiotics (such as actionmycin D, mitomycin C, daunorubicin hydrochloride, doxorubicin hydrochloride, aclarubicin hydrochloride, neocarzinostatin, pirarubicin, epirubicin, idarubicin, chromomycin A3, bleomycin, peplomycin sulfate), plant alkaloid (such as vinblastine sulfate, vincristine sulfate, vindesine sulfate), hormone (such as estramustine phosphate sodium, mepitiostane, epitiostanol, tamoxifen citrate, diethylstilbestrol phosphate, medroxyprogesterone acetate), immunopotentiation agent (such as lentinan, picibanil, krestin, shizophyllan, ubenimex, interferon), others (such as L-asparaginase, procarbazine hydrochloride, mitoxantrone hydrochloride, cisplatin, carboplatin), etc.

Examples of the steroids for external application include clobetasol propionate, diflorasone acetate, fluocinonide, monometasone furancarboxylate, betamesone dipropionate, betamesone butyropropionate, betamesone valerate, difluprednate, budesonide, diflucortolone valerate, amcinonide, halcinonide, dexamethasone, dexamethasone propionate, dexamethasone valerate, dexamethasone acetate, hydrocortisone acetate, hydrocortisone butyrate, hydrocortisone acetopropionate, deprodone propionate, prednisolone valeroacetate, fluocinolone acetonide, beclometasone dipropionate, triamcinonide acetonide, flumethasone pivalate, prednisolone, beclometasone propionate, and fludroxycortide, etc.

Examples of the steroids for internal use or injection include cortisone acetate, hydrocortisone, hydrocortisone sodium phosphate, hydrocortisone sodium succinate, fludrocortisone acetate, prednisolone, prednisolone acetate, prednisolone sodium succinate, prednisolone butylacetate, prednisolone sodium phosphate, halopredon acetate, methyl prednisolone, methyl prednisolone acetate, methyl prednisolone sodium succinate, triamicinolon, triamicinolon acetate, triamicinonolon acetonide, dexamethasone, dexamethasone acetate, dexamethasone sodium phosphate, dexamethasone palmitate, paramethasone acetate, and betamethasone, etc.

Examples of the steroids as an inhalant include beclomethasonepropionate, fluticasone propionate, budesonide, flunisolide, triamcinolon, ST-126P, ciclesonide, dexamethasone palomitionate, monometasone furancarboxylate, prasterone sulfonate, deflazacort, methylprednisolone suleptanate, and methylprednisolone sodium succinate, etc.

Examples of the $β_2$ adrenoreceptor stimulant include fenoterol hydrobromide, salbutamol sulfate, terbutaline sulfate, formoterol fumarate, salmeterol xinafoate, isoprotenol sulfate, orciprenalin sulfate, chloroprenalin sulfate, epinephrine, trimetoquinol hydrochloride, hexoprenalinmesyl sulfate, procaterol hydrochloride, tulobuterol hydrochloride, tulobuterol, pirbuterol hydrochloride, clenbuterol hydrochloride, mabuterol hydrochloride, ritodrine hydrochloride, bambuterol, dopexamine hydrochloride, meradrin tartrate, AR-C68397, levosalbutamol, R,R-formoterol, KUR-1246, KUL-7211, AR-C89855, and S-1319, etc.

Examples of the leukotriene receptor antagonist include pranlukast hydrate, montelukast, zafirlukast, seratrodast, MCC-847, KCA-757, CD-615, YM-158, L-740515, CP-195494, LM-1484, RS-635, A-93178, S-36496, BIIL-284, and ONO-4057, etc.

Examples of the thromboxane synthetase inhibitor include ozagrel hydrochloride, and imitrodast sodium, etc.

Examples of the thromboxane $A_2$ receptor antagonist include seratrodast, ramatroban, domitroban calcium dihydrate, and KT-2-962, etc.

Examples of the mediator releasing inhibitor include tranilast, sodium cromoglicate, anlexanox, repirinast, ibudilast, tazanolast, and pemilolast potassium, etc.

Examples of the antihistamines include ketotifen fumarate, mequitazine, azelastine hydrochloride, oxatomide, terfenadine, emedastine fumarate, epinastine hydrochloride, astemizole, ebastin, cetirizine hydrochloride, bepotastine, fexofenadine, lolatadine, deslolatadine, olopatadine hydrochloride, TAK-427, ZCR-2060, NIP-530, mometasone furoate, mizolastine, BP-294, andolast, auranofin, and acribastin, etc.

Examples of the xanthine derivatives include aminophylline, thoeophyline, doxophylline, cipamfylline, and diprophilline, etc.

Examples of the anticholinergic agent include ipratropium bromide, oxitropium bromide, flutropium bromide, temiverine, tiotropium bromide, and revatropate (UK-112166), etc.

Examples of the cytokine inhibitor include suplatast tosilate (trade name: IPD), etc.

Examples of the prostaglandins (hereinafter abbreviated as "PG") include PG receptor agonist, and PG receptor antagonist, etc.

Examples of PG receptor include PGE receptors (EP1, $EP_2$, $EP_3$, $EP_4$), PGD receptors (DP, CRTH2), PGF receptors (FP), PGI receptors (IP) and TX receptors (TP), etc.

Examples of the phosphodiesterase inhibitor include, for example, rolipram, cilomilast (trade name: Ariflo), Bay 19-8004, NIK-616, roflumilast (BY-217), cipamfylline (BGL-61063), atizolam (CP-80633), SCH-351591, YM-976, V-11294A, PD-168787, D-4386, and IC-485 as PDE-4 inhibitor, etc.

Examples of the elastase inhibitors include ONO-5046, ONO-6818, MR-889, PBI-1101, EPI-HNE-4, R-665, ZD-0892, ZD-8321, GW-311616, and AE-3763 etc.

Examples of the expectorant include foeniculated ammonia spirit, sodium hydrogencarbonate, bromhexine hydrochloride, carbocisteine, ambroxol hydrochloride, sustained release ambroxol hydrochloride, methylcysteine hydrochloride, acetyl cysteine, L-ethylcysteine hydrochloride, and tyloxapol, etc.

Examples of the HMG-CoA reductase inhibitor include, for example, simvastatin, lovastatin, pravastatin, fluvastatin, atorvastatin, pitavastatin, and rosuvastatin.

Examples of the fibrate preparations include, for example, fenofibrate, clinofibrate, clofibrate, aluminium clofibrate, simfibrate, and bezafibrate.

Examples of the probucol preparations include, for example, probucol.

Examples of the nicotinic acid preparations include, for example, tocopherol nicotinate, nicomol, and niceritrol.

Examples of the other antihypercholesterolemic agent include, for example, cholestyramine, soysterol, and colestimide.

Examples of the nonsteroidal antiinflammatory drug include sasapyrine, sodium salicylate, aspirin, aspirin dialuminate formulation, diflunisal, indomethacin, suprofen, ufenamate, dimethylisopropyl azulen, bufexamac, felbinac, diclofenac, tolmetin sodium, Clinoril, fenbufen, napmetone, proglumetacin, indomethacin farnesil, acemetacin, proglumetacin maleate, amfenac sodium, mofezolac, etodolac, ibuprofen, ibuprofen piconol, naproxen, flurbiprofen, flurbiprofen axethyl, ketoprofen, fenoprofen calcium, tiaprofenen, oxaprozin, pranoprofen, loxoprofen sodium, aluminoprofen, zaltoprofen, mefenamic acid, aluminum mefenamate, tolfenamic acid, floctafenine, ketophenylbutazone, oxyfenbutazone, piroxicam, tenoxicam, anpiroxicam, napageln cream, epirizole, tiaramide hydrochloride, tinoridine hydrochloride, emorfazone, sulpyrine, Migrenin, Saridon, Sedes G, Amipylo N, Sorbon, pyrine system antipyretics, acetaminophen, phenacetin, dimethothiazine mesylate, simetride formulation, and antipyrine system antipyretics, etc.

Examples of the disease modifying anti-rheumatic drug (slow-acting anti-rheumatic drug) include, for example, gold thioglucose, aurothiomalate sodium, auranofin, actarit, D-penicillamine preparations, lobenzarit disodium, bucillamine, hydroxychloroquine, and salazosulfapyridine, etc.

Examples of the chondroprotective agents include, for example, hyaluronate sodium, glucosamine, chondroitin sulfate, and glucosaminoglycan polysulfate, etc.

Examples of the prostaglandin synthase inhibitor include, for example, salazosulfapyridine, mesalazine, olsalazine, 4-aminosalicylic acid, JTE-522, auranofin, carprofen, diphenpyramid, flunoxaprofen, flurbiprofen, indomethacin, ketoprofen, lornoxicam, loxoprofen, Meloxicam, oxaprozin, parsalmide, piproxen, piroxicam, piroxicam betadex, piroxicam cinnamate, tropine indomethacinate, zaltoprofen, and pranoprofen, etc.

There is no particular limitation for the ratio by weight of the compound of formula (I) to other pharmaceuticals.

With regard to other pharmaceuticals, any two or more may be compounded and administered.

With regard to other pharmaceuticals which supplement and/or enhance the prevention and/or treatment effect of the compound of formula (I), not only that which has been found up to now but also that which will be found in future on the basis of the above-mentioned mechanism are included.

When the compound of formula (I) which are used in the present invention, or concomitant drug combined the compound of formula (I) with other drugs are used for the above-described purpose, it is usually administered systemically or topically via an oral or parenteral route.

The dose of these compounds depends on the age, weight and symptom of the patient, the remedial value, the administration method, the treatment time, etc. In practice, however, these compounds are administered orally once or several times per day each in an amount of from 0.01 mg to 1000 mg, preferably 0.1 mg to 500 mg or more preferably 0.1 mg to 300 mg per adult, parenterally once or several times per day each in an amount of from 0.01 mg to 500 mg, preferably 0.1 mg to 100 mg or more preferably 0.1 mg to 50 mg per adult or continuously administered into vein for 1 hour to 24 hours per day.

It goes without saying that the dose of these compounds may be less than the aforementioned value or may need to exceed the aforementioned range because the dose varies under various conditions as mentioned above.

When the compound of formula (I) which are used in the present invention, or a pharmaceutical composition comprising a concomitant drug combined the compound of formula (I) with other drugs is administered, they are used in the form of solid or liquid agent for oral administration, injection, agent for external application, suppository, eye drops or inhalant for parenteral administration or the like.

Examples of the solid agent for oral administration include tablet, pill, capsule, powder, and granulated powder. Examples of the capsule include hard capsule, and soft capsule.

In such a solid agent for internal application, one or more active materials are used in the form of preparation produced by an ordinary method singly or in admixture with a vehicle (e.g., lactose, mannitol, glucose, microcrystalline cellulose, starch), binder (e.g., hydroxypropyl cellulose, polyvinyl pyrrolidone, magnesium metasilicoaluminate), disintegrant (e.g., calcium fibrinoglycolate), glidant (e.g., magnesium stearate), stabilizer, dissolution aid (e.g., glutamic acid, aspartic acid) or the like. The solid agent may be coated with a coating agent (e.g., white sugar, gelatin, hydroxypropyl cellulose, hydroxypropyl methyl cellulose phthalate) or two or more layers. Alternatively, the solid agent may be capsulized by an absorbable material such as gelatin.

Examples of the liquid agent for oral administration include pharmaceutically acceptable aqueous solution, suspension, emulsion, syrup, and elixir. In such a liquid agent, one or more active agents are dissolved, suspended or emulsified in a commonly used diluent (e.g., purified water, ethanol, mixture thereof). Furthermore, such a liquid agent may comprise a wetting agent, a suspending agent, an emulsifier, a sweetening agent, a flavor, a preservative, a buffer, etc.

The agent for parenteral administration may be in the form of, e.g., ointment, gel, cream, wet compress, paste, liniment, nebula, inhalant, spray, aerosol, eye drops, collunarium or the like. These agents each contain one or more active materials and are prepared by any known method or commonly used formulation.

The ointment is prepared by any known or commonly used formulation. For example, one or more active materials are triturated or dissolved in a base to prepare such an ointment. The ointment base is selected from known or commonly used materials. In some detail, higher aliphatic acid or higher aliphatic acid ester (e.g., adipic acid, myristic acid, palmitic acid, stearic acid, oleic acid, adipic acid ester, myristic acid ester, palmitic acid ester, stearic acid ester, oleic acid ester), wax (e.g., beeswax, whale wax, ceresin), surface active agent (e.g., polyoxyethylenealkylether phosphoric acid ester), higher alcohol (e.g., cetanol, stearyl alcohol, setostearyl alcohol), silicon oil (e.g., dimethyl polysiloxane), hydrocarbon (e.g., hydrophilic petrolatum, white petrolatum, purified lanolin, liquid paraffin), glycol (e.g., ethylene glycol, diethylene glycol, propylene glycol, polyethylene glycol, macrogol), vegetable oil (e.g., castor oil, olive oil, sesame oil, turpentine oil), animal oil (mink oil, vitelline oil, squalane, squalene), water, absorption accelerator and rash preventive may be used singly or in admixture of two or more thereof.

The base may further comprise a humectant, a preservative, a stabilizer, an antioxidant, a perfume, etc.

The gel is prepared by any known or commonly used formulation. For example, one or more active materials are dissolved in a base to prepare such a gel. The gel base is selected from known or commonly used materials. For example, lower alcohol (e.g., ethanol, isopropyl alcohol), gelling agent (e.g., carboxymethyl cellulose, hydroxyethyl cellulose, hydroxypropyl cellulose, ethyl cellulose), neutralizing agent (e.g., triethanolamine, diisopropanolamine), surface active agent (e.g., polyethylene glycol monostearate), gum, water, absorption accelerator, and rash preventive are used singly or in admixture of two or more thereof. The gel base may further comprise a humectant, an antioxidant, a perfume, etc.

The cream is prepared by any known or commonly used formulation. For example, one or more active materials are dissolved in a base to prepare such a cream. The cream base is selected from known or commonly used materials. For example, higher aliphatic acid ester, lower alcohol, hydrocarbon, polyvalent alcohol (e.g., propylene glycol, 1,3-butylene glycol), higher alcohol (e.g., 2-hexyl decanol, cetanol), emulsifier (e.g., polyoxyethylene alkyl ether, aliphatic acid ester), water, absorption accelerator, and rash preventive are used singly or in admixture of two or more thereof. The cream base may further comprise a humectant, an antioxidant, a perfume, etc.

The wet compress is prepared by any known or commonly used formulation. For example, one or more active materials are dissolved in a base to prepare a kneaded mixture which is then spread over a support to prepare such a wet compress. The wet compress base is selected from known or commonly used materials. For example, thickening agent (e.g., polyacrylic acid, polyvinyl pyrrolidone, gum arabic, starch, gelatin, methyl cellulose), wetting agent (e.g., urea, glycerin, propylene glycol), filler (e.g., kaolin, zinc oxide, talc, calcium, magnesium), water, dissolution aid, tackifier, and rash preventive may be used singly or in admixture of two or more thereof. The wet compress base may further comprise a humectant, an antioxidant, a perfume, etc.

The pasting agent is prepared by any known or commonly used formulation. For example, one or more active materials are dissolved in a base to prepare a kneaded mixture which is then spread over a support to prepare such a pasting agent. The pasting agent base is selected from known or commonly used materials. For example, polymer base, fat and oil, higher aliphatic acid, tackifier and rash preventive may be used singly or in admixture of two or more thereof. The pasting agent base may further comprise a humectant, an antioxidant, a perfume, etc.

The liniment is prepared by any known or commonly used formulation. For example, one or more active materials are dissolved, suspended or emulsified in water, alcohol (e.g., ethanol, polyethylene glycol), higher aliphatic acid, glycerin, soap, emulsifier, suspending agent, etc., singly or in combination of two or more thereof, to prepare such a liniment. The liniment may further comprise a humectant, an antioxidant, a perfume, etc.

The nebula, inhalant and spray each may comprise a stabilizer such as sodium hydrogensulfite and a buffer capable of providing isotonicity such as isotonic agent (e.g., sodium chloride, sodium citrate, citric acid). For the process for the preparation of spray, reference can be made to U.S. Pat. Nos. 2,868,691 and 3,095,355.

The injection for parenteral administration may be in the form of solution, suspension, emulsion or solid injection to be dissolved or suspended in a solvent in use. The injection is prepared by dissolving, suspending or emulsifying one or more active materials in a solvent. As such a solvent there may be used distilled water for injection, physiological saline, vegetable oil, alcohol such as propylene glycol, polyethylene glycol and ethanol, etc., singly or in combination. The injection may further comprise a stabilizer, a dissolution aid (e.g., glutamic acid, aspartic acid, Polysolvate 80 (trade name)), a suspending agent, an emulsifier, a soothing agent, a buffer, a preservative, etc. The injection is sterilized at the final step or prepared by an aseptic process. Alternatively, an aseptic solid agent such as freeze-dried product which has previously been prepared may be rendered aseptic or dissolved in an aseptic distilled water for injection or other solvent before use.

The eye drops for parenteral administration may be in the form of liquid, suspension, emulsion, formulation to be dissolved before use, or ointment or may be dissolved in a solvent in use.

These eye drops are prepared by any known method. For example, one or more active materials are dissolved, suspended or emulsified in a solvent. As such a solvent for eye drops there may be used sterilized purified water, physiological saline and other aqueous or nonaqueous solvents (e.g., vegetable oil), singly or in combination. The eye drops may comprise an isotonic agent (e.g., sodium chloride, concentrated glycerin), a buffering agent (e.g., sodium phosphate, sodium acetate), a surface active agent (e.g., Polysolvate 80 (trade name), polyoxyl stearate 40, polyoxyethylene-hardened castor oil), a stabilizer (sodium citrate, sodium edetate), a preservative (e.g., benzalconium chloride, Paraben), etc. properly selectively as necessary. The eye drops are sterilized at the final step or prepared by an aseptic process. Alternatively, an aseptic solid agent such as freeze-dried product which has previously been prepared may be rendered aseptic or dissolved in an aseptic distilled water for injection or other solvent before use.

The inhalant for parenteral administration may be in the form of aerosol, powder for inhalation or liquid for inhalation. The liquid for inhalation may be dissolved or suspended in water or other proper medium in use.

These inhalants are prepared by an known method.

For example, the liquid for inhalation is prepared from materials properly selected from preservatives (e.g., benzalconium chloride, Paraben), colorants, buffering agents (e.g., sodium phosphate, sodium acetate), isotonic agents (e.g., sodium chloride, concentrated glycerin), thickening agents (e.g., carboxyvinyl polymer), absorption accelerators, etc. as necessary.

The powder for inhalation is prepared from materials properly selected from glidants (e.g., stearic acid and salt thereof), binders (e.g., starch, dextrin), vehicles (e.g., lactose, cellulose), colorants, preservatives (e.g., benzalconium chloride, Paraben), absorption accelerators, etc., if necessary.

In order to administer the liquid for inhalation, a sprayer (e.g., atomizer, nebulizer) is normally used. In order to administer the powder for inhalation, a powder inhaler is normally used.

Other examples of the composition for oral administration include sublingual medication for sublingual administration, suppository for rectal administration and pessary for vaginal administration prepared by an ordinary formulation comprising one or more active materials.

Referring to the local administration of the compound of formula (I) of the present invention, medicament may be locally administered to site of disease. The form of medicament is not limited to its administration method. The medicament may be in the form of injection which is administered to intramuscular, subcutaneous, organic or articular site, solid agent (such as embedding agent, granulated powder and powder) or ointment.

The sustained release formulation of the compound of formula (I) of the present invention is not limited to its form so far as medicament can be continuously administered to site of disease. The sustained release formulation may be in the form of, e.g., sustained release injection (e.g., microcapsuled formulation, microspheric formulation, nanospheric formulation), embedding formulation (e.g., film-like formulation) or the like.

The microcapsuled formulation, microspheric formulation and nanospheric formulation of the invention each are particulate pharmaceutical composition with an biodegradable polymer comprising the compound of formula (I) of the present invention, or concomitant drug combined the compound of formula (I) of the present invention with other drugs as active components.

Examples of the biodegradable polymer of the invention include aliphatic acid ester polymers and copolymers thereof, polyacrylic acid esters, polyhydroxybutyric acids, polyalkylene oxalates, polyorthoesters, polycarbonates, and polyaminoacids. These compounds may be used singly or in admixture of two or more thereof. Examples of the aliphatic acid ester polymers and copolymers thereof include polylactic acid, polyglycolic acid, polycitric acid, polymalic acid, and lactic acid-glycolic acid copolymer. These compounds may be used singly or in admixture of two or more thereof. Besides these compounds, poly-α-cyanoacrylic acid esters, poly-β-hydroxybutyric acids, polytrimethyleneoxalates, polyorthoesters, polyorthocarbonates, polyethylene carbonates, poly-γ-benzyl-L-glutamic acids and poly-L-alanines may be used singly or in admixture of two or more thereof. Preferred among these compounds are polylactic acids, polyglycolic acids and lactic acid-glycolic acid copolymers, more preferably lactic acid-glycolic acid copolymers.

The average molecular weight of these biodegradable polymers to be used in the invention is preferably from about 2,000 to 800,000, more preferably from about 5,000 to 200,000. For example, the polylactic acid preferably has a weight-average molecular weight of from about 5,000 to 100,000, more preferably from about 6,000 to 50,000. The polylactic acid can be synthesized according to any known preparation method per se. In the lactic acid-glycolic acid copolymer, the composition ratio of the lactic acid to the glycolic acid is preferably from about 100/0 to 50/50 (w/w), particularly from about 90/10 to 50/50. The weight-average molecular weight of the lactic acid-glycolic acid copolymer is preferably from about 5,000 to 100,000, more preferably from about 10,000 to 80,000. The lactic acid-glycolic acid copolymer can be synthesized according to any known preparation method per se.

The term "weight-average molecular weight" as used herein is meant to indicate molecular weight in polystyrene equivalence determined by gel permeation chromatography (GPC).

The aforementioned biodegradable polymer may be changed depending on the intensity of pharmacological activity of the compound of formula (I) which are used in the present invention, or concomitant drug combined the compound of formula (I) with other drugs and the desired medicines to be released so far as the aforementioned aims of the invention are accomplished. For example, the biodegradable polymer may be used in an amount of from about 0.2 to 10,000 times (by weight), preferably from about 1 to 1,000 times (by weight), more preferably from about 1 to 100 times (by weight) that of the physiologically active material.

The nomenclature of the compound of the present invention is described below.

The nomenclature in the present specification was done by means of a method according as a rule of IUPAC, or ACD/Name or ACD/Name Batch (registered tradename, both manufactured by Advanced Chemistry Development Inc.), which is a computerized system to denominate a compound generally according to rule of IUPAC. For example, a compound shown by the following:

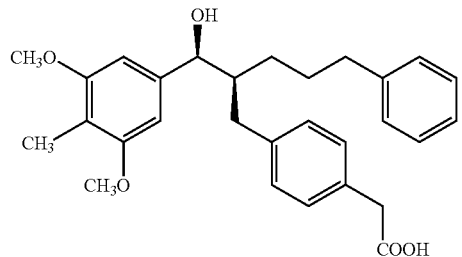

is named (4-{(2S)-2-[(S)-(3,5-dimethoxy-4-methylphenyl)(hydroxy)methyl]-5-phenylpentyl}phenyl)acetic acid.

EFFECT OF THE INVENTION

Since the compound of the present invention of formula (I) of the present invention, a salt thereof, a solvate thereof, or a prodrug thereof is antagonistic to LPA receptor (especially EDG-2), it is useful for prevention and/or treatment urinary system disease, carcinoma-associated disease, proliferative disease, inflammation /immune system disease, disease by secretory dysfunction, brain-related disease or chronic disease.

BEST MODE FOR CARRYING OUT THE INVENTION

The following reference examples and examples illustrate the present invention, but they do not limit the present invention.

The solvents in the parentheses show the developing solvents or eluting solvents and the ratios of the solvents used are by volume in chromatographic separations or TLC. The solvent used in the measurement of NMR was deuterochloroform ($CDCl_3$), unless otherwise indicated.

Whether the product is amorphous was confirmed by a polarization microscope.

EXAMPLE 1

2-{4-[5-phenyl-2-(3,4,5-trimethoxybenzoyl)pentyl]phenoxy}benzoic acid 3,4,5-Trimethoxybenzoic acid was allowed to react with oxalyl chloride, and the resulting acid chloride was allowed to react with N,O-dimethylhydroxyamine hydrochloride to obtain N,3,4,5-tetramethoxy-N-methylbenzamide. The resulting compound was allowed to react with 4-phenylbutylmagnesium chloride to obtain 5-phenyl-1-(3,4,5-trimethoxyphenyl)pentan-1-one. The resulting compound was allowed to react with lithium diisopropylamine and methyl2-[4-(bromomethyl)phenoxy]benzoate in the presence of N,N,N',N",N"-pentamethyldiethylenetriamine to obtain methyl2-{4-[5-phenyl-2-(3,4,5-trimethoxybenzoyl)pentyl]

phenoxy}benzoate. The resulting compound was hydrolyzed with sodium hydroxide to give the title compound having the following physical properties.

TLC: Rf 0.43 (dichloromethane:methanol=9:1);
$^1$HNMR: δ 8.19 (dd, 1H), 7.45 (m, 1H), 7.30-7.08 (m, 8H), 7.04 (s, 2H), 6.95 (d, 2H), 6.63 (d, 1H), 3.90 (s, 3H), 3.85 (s, 6H), 3.65 (m, 1H), 3.07 (dd, 1H), 2.83 (dd, 1H), 2.60 (t, 2H), 1.98-1.45 (m, 4H).

EXAMPLE 2

2-(4-{2-[hydroxy(3,4,5-trimethoxyphenyl)methyl]-5-phenylpentyl}phenoxy)benzoic acid

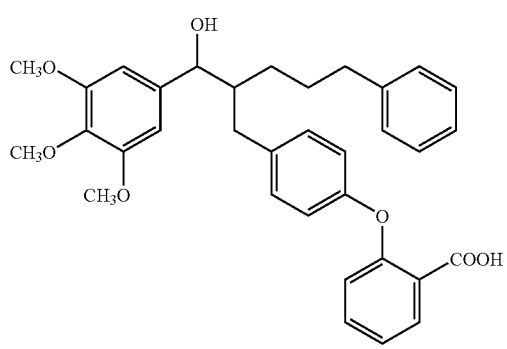

To a mixture solution of the compound produced in Example 1 (100 mg) in tetrahydrofuran (4 ml) and methanol (4 ml), sodium borohydride (100 mg) was added. The reaction mixture was stirred at room temperature for 1 hour. A saturated aqueous ammonium chloride solution was added to the reaction mixture, followed extraction with ethyl acetate. The extract was washed with brine, dried over anhydrous sodium sulfate, and concentrated. The residue was purified with silica gel column chromatography (dichloromethane:methanol=30:1→20:1) to give the title compound (34 mg) having the following physical properties.

TLC: Rf 0.46 (dichloromethane:methanol=9:1);
$^1$HNMR: δ 8.23 (dd, 1H), 7.46 (ddd, 1H), 7.30-6.98 (m, 10H), 6.79 (d, 1H), 6.56-6.48 (m, 2H), 4.58 (m, 1H), 3.88-3.80 (m, 9H), 2.92-2.45 (m, 4H), 2.02 (m, 1H), 1.82-1.30 (m, 4H).

EXAMPLE 2(1) TO EXAMPLE 2(7)

Using 3,4,5-trimethoxybenzoic acid or a corresponding carboxylic acid derivative, 4-phenylbutylmagnesium chloride or a corresponding Grignard reagent, or methyl2-[4-(bromomethyl)phenoxy]benzoate or a corresponding benzyl chloride derivative, procedures similar to Example 1→Example 2 were carried out to give each of the following compounds.

EXAMPLE 2(1)

2-(4-{2-[(3,5-dimethoxy-4-methylphenyl)(hydroxy)methyl]-5-phenylpentyl}phenoxy)benzoic acid TLC: Rf 0.48 (dichloromethane:methanol=9:1);
$^1$HNMR: δ 8.23 (dd, 1H), 7.45 (dd, 1H), 7.30-7.04 (m, 8H), 7.00 (d, 2H), 6.77 (m, 1H), 6.52-6.44 (m, 2H), 4.60 (m, 1H), 3.82-3.78 (m, 6H), 2.95-2.45 (m, 4H), 2.10-1.98 (m, 4H), 1.80-1.30 (m, 4H).

EXAMPLE 2(2)

3-{2-[hydroxy(3,4,5-trimethoxyphenyl)methyl]-5-phenylpentyl}benzoic acid

TLC: Rf 0.28 (dichloromethane:methanol=9:1);
$^1$HNMR: δ 7.98-7.88 (m, 2H), 7.40-7.02 (m, 7H), 6.58-6.46 (m, 2H), 4.62-4.54 (m, 1H), 3.88-3.78 (m, 9H), 2.95-2.44 (m, 4H), 2.05 (m, 1H), 1.80-1.15 (m, 4H).

EXAMPLE 2(3)

2-(4-{2-[(3,5-dimethoxy-4-methylphenyl)(hydroxy)methyl]-5-phenylpentyl}phenoxy)-4-methylbenzoic acid TLC: Rf 0.55 (dichloromethane:methanol=9:1);
$^1$HNMR: δ 8.11 (d, 1H), 7.28-6.96 (m, 10H), 6.58 (s, 1H), 6.52-6.45 (m, 2H), 4.60 (m, 1H), 3.83-3.78 (m, 6H), 2.92-2.45 (m, 4H), 2.28 (s, 3H), 2.12-2.06 (m, 3H), 2.04 (m, 1H), 1.82-1.42 (m, 4H).

EXAMPLE 2(4)

(4-{2-[(3,5-dimethoxy-4-methylphenyl)(hydroxy)methyl]-4-phenylbutyl}phenyl)acetic acid TLC: Rf 0.32 (dichloromethane:methanol=9:1);
$^1$HNMR: δ 7.35-6.92 (m, 9H), 6.5.0-6.42 (m, 2H), 4.64 (m, 1H), 3.81-3.75 (m, 6H), 3.63 (s, 2H), 2.92-2.44 (m, 4H), 2.08-2.04 (m, 3H), 2.03-1.35 (m, 3H).

EXAMPLE 2(5)

(4-{2-[(3,5-dimethoxy-4-methylphenyl)(hydroxy)methyl]-6-phenylhexyl}phenyl)acetic acid TLC: Rf 0.31 (dichloromethane:methanol=9:1);
$^1$HNMR: δ 7.32-7.05 (m, 9H), 6.52-6.42 (m, 2H), 4.60 (m, 1H), 3.82-3.78 (m, 6H), 3.62 (s, 2H), 2.82-2.42 (m, 4H), 2.10-2.02 (m, 3H), 2.02-1.20 (m, 7H).

EXAMPLE 2(6)

(4-{2-[(3,5-dimethoxy-4-methylphenyl)(hydroxy)methyl]-5-tetrahydro-2H-pyran-4-ylpentyl}phenyl)acetic acid TLC: Rf 0.67 (ethyl acetate:methanol=9:1);
$^1$HNMR: δ 7.19 (d, 2H), 7.11 (d, 2H), 6.51-6.45 (m, 2H), 4.60 (m, 2H), 4.00-3.50 (m, 10H), 3.40-3.20 (m, 2H), 2.90-2.40 (m, 2H), 2.20-1.90 (m, 4H), 1.50-1.00 (m, 11H).

EXAMPLE 2(7)

{4-[2-benzyl-3-(3,5-dimethoxy-4-methylphenyl)-3-hydroxypropyl]phenyl}acetic acid TLC: Rf 0.46 (chloroform:methanol =9:1);
$^1$HNMR: δ 2.06 (s, 3H), 2.44 (m, 2H), 2.69 (m, 3H), 3.58 (m, 2H), 3.72 (s, 1H), 3.79 (s, 6H), 4.61 (d, 1H), 6.45 (s, 2H), 7.15 (m, 9H).

EXAMPLE 3 methyl(4-{2-[(3,5-dimethoxy-4-methylphenyl)(hydroxy)methyl]-5-phenylpentyl}phenyl)acetate 3,5-Dimethoxy-4-methylbenzoic acid was allowed to react with oxalyl chloride, and the resulting acid chloride was allowed to react with N,O-dimethylhydroxyamine hydrochloride to obtain N,3,5-trimethoxy-N,4-dimethylbenzamide. The resulting compound was allowed to react with 4-phenylbutylmagnesium chloride to obtain 1-(3,5-dimethoxy-4-methylphenyl)-5-phenylpentan-1-one. The resulting compound was allowed to react with lithium diisopropylaminez and methyl[4-(bromomethyl)phenyl]acetate in the presence of N,N,N',N'',N''-pentamethyldiethylenetriamine to obtain methyl{4-[2-(3,5-dimethoxy-4-methylbenzolyl)-5-phenylpentyl]phenyl}acetate. Using the obtained compound, the procedure similar to Example 2 were carried out to give the title compound having the following physical properties.

TLC: Rf 0.40 (hexane:ethyl acetate=1:1);

¹HNMR: δ 7.32-7.02 (m, 9H), 6.50 (s, 1/2H), 6.44 (s, 3/2H), 4.60 (m, 1H), 3.81 (s, 3/2H), 3.78 (s, 9/2H), 3.69 (s, 3H), 3.60 (s, 2H), 2.90-2.42 (m, 4H), 2.07 (s, 3H), 2.02 (m, 1H), 1.75-1.05 (m, 4H).

EXAMPLE 4(1) TO EXAMPLE 4(4)

The compound produced in Example 3 was purified under the following HPLC conditions to separate syn-diasteromer (mixture of Example 4(1) with Example 4(2)) and anti-diastereomer (mixture of Example 4(3) with Example 4(4)).
HPLC preparative conditions:
Column: normal phase silica gel column YMC-Pack SIL (250×30 mm);
Elution solvent: hexane:tetrahydrofuran=85:15;
Flow rate: 25 ml/min;
Retention time: 37.03 min (syn-diastereomer), 39.56 min (anti-diastereomer).

Using the syn-diastereomer and anti-diastereomer obtained by the above method, purification was carried out by the following HPLC conditions to separate each of the following compounds.
HPLC preparative conditions:
Column: normal phase CHIRALCEL OJ-H (2 cmφ×25 cm);
Elution solvent: methanol;
Flow rate: 9.5 ml/min;
Retention time: 27.50 min [Example 4(1)], 24.73 min [Example 4(2)], 40.56 min [Example 4(3)], 48.83 min [Example 4(4)]

EXAMPLE 4(1)

methyl(4-{(2S)-2-[(S)-(3,5-dimethoxy-4-methylphenyl)(hydroxy)methyl]-5-phenylpentyl}phenyl)acetate

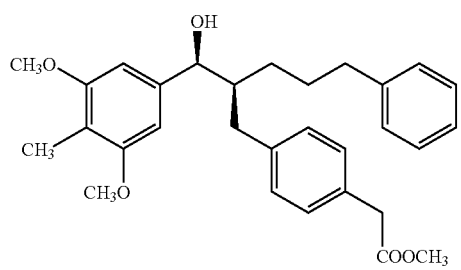

TLC: Rf 0.40 (hexane:ethyl acetate=1:1);

¹HNMR: δ 7.27-7.02 (m, 9H), 6.50 (s, 2H), 4.59 (m, 1H), 3.81 (s, 6H), 3.70 (s, 3H), 3.60 (s, 2H), 2.82 (dd, 1H), 2.61 (dd, 1H), 2.45 (t, 2H), 2.09 (s, 3H), 2.02 (m, 1H), 1.68-1.10 (m, 4H).

EXAMPLE 4(2)

methyl(4-{(2R)-2-[(R)-(3,5-dimethoxy-4-methylphenyl)(hydroxy)methyl]-5-phenylpentyl}phenyl)acetate

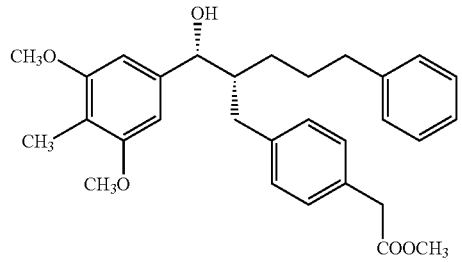

Data of TLC and ¹HNMR were similar to those in Example 4(1).

EXAMPLE 4(3)

methyl(4-{(2R)-2-[(S)-(3,5-dimethoxy-4-methylphenyl)(hydroxy)methyl]-5-phenylpentyl}phenyl)acetate

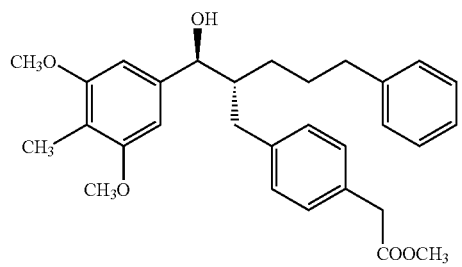

TLC: Rf 0.40 (hexane:ethyl acetate=1:1);

¹HNMR: δ 7.25-7.04 (m, 9H), 6.44 (s, 2H), 4.59 (m, 1H), 3.78 (s, 6H), 3.69 (s, 3H), 3.60 (s, 2H), 2.66 (dd, 1H), 2.55-2.45 (m, 3H), 2.07 (s, 3H), 2.03 (m, 1H), 1.78-1.38 (m, 4H).

EXAMPLE 4(4)

methyl(4-{(2S)-2-[(R)-(3,5-dimethoxy-4-methylphenyl)(hydroxy)methyl]-5-phenylpentyl}phenyl)acetate

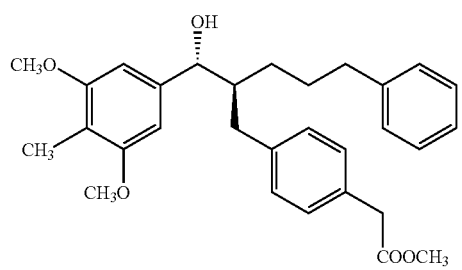

Data of TLC and ¹HNMR were similar to those in Example 4(3).

EXAMPLE 5(1)

(4-{(2S)-2-[(S)-(3,5-dimethoxy-4-methylphenyl)(hydroxy)methyl]-5-phenylpentyl}phenyl)acetic acid To a methanol (3 ml) solution of the compound (100 mg) purified in Example 4(1), 1N sodium hydroxide (3 ml) was added, followed by stirring at room temperature for 30 minutes. To the reaction mixture, 1N hydrochloric acid was added, followed by concentration. Water was added to the residue, followed by extraction with ethyl acetate. The extract was washed with brine, dried over anhydrous sodium sulfate, and concentration to give the title compound (85 mg) having the following physical properties.

TLC: Rf 0.39 (dichloromethane:methanol=9:1);
$^1$HNMR: δ 7.24-7.03 (m, 9H), 6.50 (s, 2H), 4.59 (d, 1H), 3.81 (s, 6H), 3.63 (s, 2H), 2.82 (dd, 1H), 2.61 (dd, 1H), 2.45 (t, 2H), 2.09 (s, 3H), 2.04 (m, 1H), 1.75-1.10 (m, 4H).

EXAMPLE 5(2) TO EXAMPLE 5(4)

Using each of the compounds purified in Example 4(2) to 4(4) instead of the compound purified in Example 4(1), procedures similar to Example 5(1) were carried out to obtain the following compound of the present invention.

EXAMPLE 5(2)

(4-{(2R)-2-[(R)-(3,5-dimethoxy-4-methylphenyl)(hydroxy)methyl]-5-phenylpentyl}phenyl)acetic acid Data of TLC and $^1$HNMR were similar to those in Example 5(1).

EXAMPLE 5(3)

(4-{(2R)-2-[(S)-(3,5-dimethoxy-4-methylphenyl)(hydroxy)methyl]-5-phenylpentyl}phenyl)acetic acid TLC: Rf 0.40 (dichloromethane:methanol=9:1);
$^1$HNMR: δ 7.30-7.05 (m, 9H), 6.43 (s, 2H), 4.59 (d, 1H), 3.78 (s, 6H), 3.63 (s, 2H), 2.66 (dd, 1H), 2.55-2.45 (m, 3H), 2.07 (s, 3H), 2.03 (m, 1H), 1.78-1.58 (m, 4H).

EXAMPLE 5(4)

(4-{(2S)-2-[(R)-(3,5-dimethoxy-4-methylphenyl)(hydroxy)methyl]-5-phenylpentyl}phenyl)acetic acid Data of TLC and $^1$HNMR were similar to those in Example 5(3).

EXAMPLE 6

(±)-methyl2-[4-({(1S*)-1-[(R*)-(3,5-dimethoxy-4-methylphenyl)(methoxymethoxy)methyl]-4-phenylbutyl}oxy)phenoxy]-4-methylbenzoate To a tetrahydrofuran (4 ml) solution of (±)-(1R*,2R*)-1-(3,5-dimethoxy-4-methylphenyl)-1-(methoxymethoxy)-5-phenylpentan-2-ol (142 mg) and methyl2-(4-hydroxyphenoxy)-4-methylbenzoate (249 mg), triphenylphosphine (262 mg) and diethyl azodicarboxylate (0.47 ml) were added, followed by stirring at room temperature overnight. The reaction mixture was concentrated, and the residue was purified with silica gel column chromatography (hexane:ethyl acetate=9:1) to obtain the title compound (128 mg) having the following physical properties.

TLC: Rf 0.62 (hexane:ethyl acetate=2:1);
$^1$HNMR: δ 1.66 (m, 1H), 1.85 (m, 3H), 2.06 (s, 3H), 2.30 (s, 3H), 2.59 (m, 2H), 3.37 (s, 3H), 3.77 (s, 6H), 3.81 (s, 3H), 4.33 (m, 1H), 4.59 (s, 2H), 4.76 (d, 1H), 6.50 (s, 2H), 6.68 (s, 1H), 6.85 (m, 5H), 7.15 (m, 5H), 7.79 (d, 1H).

EXAMPLE 7

(±)-methyl2-[4-({(1S )-1-[(R*)-(3,5-dimethoxy-4-methylphenyl)(hydroxy)methyl]-4-phenylbutyl}oxy)phenoxy]-4-methylbenzoate To a tetrahydrofuran (4 ml) solution of the compound (128 mg) produced in Example 6, 5N hydrochloric acid (1 ml) was added, and the mixture was stirred at 50° C. for 20 hours. The reaction mixture was diluted with ethyl acetate, washed with water and brine successively, dried over anhydrous magnesium sulfate, and concentrated. The residue was purified with silica gel column chromatography (hexane:ethyl acetate=4:1) to give the title compound (113 mg) having the following physical properties.

TLC: Rf 0.40 (hexane:ethyl acetate=2:1);
$^1$HNMR: δ 1.78 (m, 4H), 2.08 (s, 3H), 2.31 (s, 3H), 2.56 (t, 2H), 3.70 (m, 1H), 3.81 (m, 9H), 4.34 (m, 1H), 4.95 (t, 1H), 6.55 (s, 2H), 6.71 (br. s., 1H), 6.89 (m, 4H), 6.95 (m, 1H), 7.13 (m, 5H), 7.80 (d, 1H).

EXAMPLE 8

(±)-2-[4-({(1S*)-1-[(R*)-(3,5-dimethoxy-4-methylphenyl)(hydroxy)methyl]-4-phenylbutyl}oxy)phenoxy]-4-methylbenzoic acid Using the compound produced in Example 7 instead of the compound purified in Example 4(1), procedures similar to Example 5(1) were carried out to give the title compound having the following properties.

TLC: Rf 0.59 (hexane:ethyl acetate=1:4);
$^1$HNMR: δ 1.50-1.90 (m, 4H), 2.08 (s, 3H), 2.31 (s, 3H), 2.58 (t, 2H), 3.81 (s, 6H), 4.42 (m, 1H), 4.93 (d, 1H), 6.56 (s, 3H), 6.92-7.28 (m, 10 H), 8.10 (d, 1 H).

EXAMPLE 9

(±)-methyl2-[4-({(1 s*)-1-[(S*)-(benzoyloxy)(3,5-dimethoxy-4-methylphenyl)methyl]-4-phenylbutyl}oxy)phenoxy]-4-methylbenzoate Using the compound produced in Example 7 instead of (±)-(1R*,2R*)-1-(3,5-dimethoxy-4-methylphenyl)-1-(methoxymethoxy)-5-phenylpentan-2-ol and using benzoic acid instead of methyl2-(4-hydroxyphenoxy)-4-methylbenzoate, procedures similar to Example 6 were carried out to give the title compound having the following properties.

TLC: Rf 0.24 (hexane:ethyl acetate=4:1).

EXAMPLE 10

(±)-methyl2-[4-({(1S*)-1-[(S*)-(3,5-dimethoxy-4-methylphenyl)(hydroxy)methyl]-4-phenylbutyl}oxy)phenoxy]-4-methylbenzoate To a methanol (2 ml) solution of the compound (43 mg) produced in Example 9, potassium carbonate (20 mg) was added, and the mixture was stirred at room temperature for 5 hours. Water was added to the reaction mixture, and extracted with ethyl acetate. The extract was washed with brine, dried over anhydrous magnesium sulfate, and concentrated. The residue was purified with silica gel column chromatography (hexane:ethyl acetate=4:1) to give the title compound (29 mg) having the following properties.

TLC: Rf 0.32 (hexane:ethyl acetate=2:1);
$^1$HNMR: δ 1.76 (m, 4H), 2.08 (s, 3H), 2.30 (s, 3H), 2.52 (m, 2H), 2.71 (d, 1H), 3.81 (m, 9H), 4.32 (m, 1H), 4.73 (dd, 1H), 6.55 (s, 2H), 6.71 (s, 1H), 6.89 (s, 4H), 6.95 (m, 1H), 7.05 (m, 2H), 7.17 (m, 3H), 7.80 (d, 1H).

EXAMPLE 11

(±)-2-[4-({(1S*)-1-[(S*)-(3,5-dimethoxy-4-methylphenyl)(hydroxy)methyl]-4-phenylbutyl}oxy)phenoxy]-4-methylbenzoic acid Using the compound produced in Example 10 instead of the compound produced in Example 4(1), procedures similar to Example 5(1) were carried out to give the title compound having the following properties.

TLC: Rf 0.56 (hexane:ethyl acetate=1:4);
$^1$HNMR: δ 1.50-2.00 (m, 4H), 2.06-2.11 (m, 3H), 2.30 (s, 3H), 2.48-2.63 (m, 2H), 3.81 (s, 6H), 4.35-4.45 (m, 1H), 4.73-4.95 (m, 1H), 6.54-6.59 (m, 3H), 6.92-7.28 (m, 10H), 8.10 (d, 1H).

EXAMPLE 12

(4S)-4-benzyl-3-(5-phenylpentanoyl)-1,3-oxazolidin-2-one

To a tetrahydrofuran (300 ml) solution of (4S)-4-benzyl-1,3-oxazolidin-2-one (26.58 g), 1.58 M of n-butyl lithium (tetrahydrofuran solution; 100 ml) was added under argon atmosphere at −78° C., and the mixture was stirred at the same temperature for 40 minutes. To the mixture, a tetrahydrofuran (100 ml) solution of 5-phenylpentanoyl chloride (32.4 g) was added, followed by stirring at −78° C. for 5 minutes. An aqueous ammonium chloride solution was added to the reaction mixture, followed by extraction with ethyl acetate. The extract was washed with a saturated aqueous sodium hydrogen carbonate solution and brine successively, dried over anhydrous sodium sulfate and concentrated to give the title compound (55.29 g) having the following physical properties.

TLC: Rf 0.43 (hexane:ethyl acetate=4:1);
$^1$HNMR: δ 1.71 (m, 4H), 2.72 (m, 3H), 2.94 (m, 2H), 3.29 (dd, 1H), 4.16 (m, 2H), 4.66 (m, 1H), 7.26 (m, 10H).

EXAMPLE 13

(4S)-4-benzyl-3-{(2R)-2-[(S)-(3,5-dimethoxy-4-methylphenyl)(hydroxy)methyl]-5-phenylpentanoyl}-1,3-oxazolidin-2-one To an ethyl acetate (18 ml) solution, the compound (6.13 g) produced in Example 12 and 3,5-dimethoxy-4-methylbenzaldehyde (3.60 g), triethylamine (5.07 ml), trimethylsilyl chloride (3.47 ml) and magnesium chloride (347 mg) were added, and the mixture was stirred at room temperature overnight. Water was added to the reaction mixture, followed by extraction with ethyl acetate. The extract was washed with brine, dried over anhydrous sodium sulfate, and concentrated. The residue was dissolved in methanol (18 ml), and 1N hydrochloric acid (1.8 ml) was added thereto. The reaction mixture was stirred at room temperature for 5 mintues, and concentrated. The residue was purified with silica gel column chromatography (hexane:ethyl acetate=49:1→19:1→9:1 4:1) to give the title compound (8.24 g) having the following physical properties.

TLC: Rf 0.61 (hexane:ethyl acetate=2:1);
$^1$HNMR: δ 1.58 (m, 2H), 1.86 (m, 1H), 2.08 (s, 3H), 2.49 (dd, 1H), 2.57 (t, 2H), 3.09 (dd, 1H), 3.20 (d, 1H), 3.82 (s, 6H), 4.10 (m, 2H), 4.62 (m, 2H), 4.80 (m, 1H), 6.63 (s, 2H), 7.19 (m, 10H).

EXAMPLE 14

(4S)-4-benzyl-3-{(2R)-2-[(S)-{[tert-butyl(dimethyl)silyl]oxy}(3,5-dimethoxy-4-methylphenyl)methyl]-5-phenylpentanoyl}-1,3-oxazolidin-2-one To a dichloromethane (109 ml) solution of the compound (28.2 g) produced in Example 13, 2,6-lutidine (7 ml) and tert-butyldimethylsilyl trifluoromethanesulfonate (13.7 ml) were added, and the mixture was stirred at room temperature for 30 minutes. The reaction mixture was concentrated, and the residue was purified with silica gel column chromatography (hexane:ethyl acetate=49:1→19:1→9:1) to give the title compound (32.5 g) having the following properties.

TLC: Rf 0.64 (hexane:ethyl acetate=4:1);
$^1$HNMR: 6-0.27 (s, 3H), −0.03 (s, 3H), 0.83 (s, 9H), 1.43 (m, 4H), 2.10 (s, 3H), 2.41 (m, 2H), 2.58 (dd, 1H), 3.54 (dd, 1H), 3.82 (s, 6H), 4.10 (m, 2H), 4.44 (m, 1H), 4.64 (m, 1H), 4.80 (d, 1H), 6.59 (s, 2H), 7.19 (m, 10H).

EXAMPLE 15

(2S)-2-[(S)-{[tert-butyl(dimethyl)silyl]oxy}(3,5-dimethoxy-4-methylphenyl)methyl]-5-phenylpentan-1-ol To a tetrahydrofuran (500 ml) solution of the compound (31.59 g) produced in Example 14, lithium borohydride (10.9 g) was added, and the mixture was stirred at room temperature for 4 hours. To the reaction mixture, 1N hydrochloric acid was added at 0° C., followed by extraction with ethyl acetate. The extract was washed with a saturated aqueous sodium hydrogen carbonate solution and brine successively, dried over anhydrous sodium sulfate, and concentrated. The residue was purified with silica gel column chromatography (hexane:ethyl acetate=50:1→20:1→9:1) to give the title compound (6.52 g) having the following physical properties.

TLC: Rf 0.47 (hexane:ethyl acetate=4:1);
$^1$HNMR: δ −0.17 (s, 3H), 0.05 (s, 3H), 0.92 (s, 9H), 1.59 (m, 4H), 2.07 (s, 3H), 2.59 (t, 2H), 3.01 (dd, 1H), 3.55 (m, 1H), 3.77 (m, 1H), 3.80 (s, 6H), 4.70 (d, 1H), 6.46 (s, 2H), 7.21 (m, 5H).

EXAMPLE 16

(2S)-2-[(S)-{[tert-butyl(dimethyl)silyl]oxy}(3,5-dimethoxy-4-methylphenyl)methyl]-5-phenylpentyl methanesulfonate To a tetrahydrofuran (4.4 ml) solution of the compound (200 mg) produced in Example 15, triethylamine (218 μl) and mesyl chloride (102 μl) were added, and the mixture was stirred at room temperature for 2 hours. Water was added to the reaction mixture, followed by extraction with ethyl acetate. The extract was washed with brine, dried over anhydrous sodium sulfate, and concentrated to give the title compound (253 mg) having the following physical properties.

TLC: Rf 0.76 (toluene:ethyl acetate=9:1);
$^1$HNMR: δ −0.21 (s, 3H), 0.03 (s, 3H), 0.89 (s, 9H), 1.51 (m, 4H), 1.92 (m, 1H), 2.08 (s, 3H), 2.55 (m, 2H), 2.89 (s, 3H), 3.80 (s, 6H), 4.29 (dd, 1H), 4.36 (m, 1H), 4.58 (d, 1H), 6.43 (s, 2H), 7.19 (m, 5H).

EXAMPLE 17 tert-butyl{[(1S,2R)-1-(3,5-dimethoxy-4-methylphenyl)-2-(iodomethyl)-5-phenylpentyl]oxy}dimethylsilane To an acetone (4.4 ml) solution of the compound (253 mg) produced in Example 16, sodium iodide (654 mg) was added, and the mixture was stirred at 90° C. for 3 hours. Water was added to the reaction mixture, followed by extraction with ethyl acetate. The extract was washed with brine, dried over anhydrous sodium sulfate, and concentrated to give the title compound (263 mg) having the following physical properties.

TLC: Rf 0.71 (hexane:ethyl acetate=19:1);
$^1$HNMR: 6-0.24 (s, 3H), 0.08 (s, 3H), 0.87 (m, 9H), 1.25 (m, 4H), 1.58 (m, 1H), 2.08 (s, 3H), 2.49 (m, 2H), 3.32 (dd, 1H), 3.65 (dd, 1H), 3.80 (s, 6H), 4.34 (d, 1H), 6.44 (s, 2H), 7.19(m, 5H).

EXAMPLE 18 methyl3-(3-{(2S)-2-[(S)-{[tert-butyl(dimethyl)silyl]oxy}(3,5-dimethoxy-4-methylphenyl)methyl]-5-phenylpentyl}phenyl)propanoate To a mixture of zinc (276 mg) and N,N-dimethylformamide (0.8 ml), 1,2-dibromoethane (18 µl) was added under argon atmosphere, and the mixture was stirred at 60° C. for 30 minutes. To the mixture, trimethylsilyl chloride (50 µl) was added, followed by stirring at room temperature for 30 minutes. To the mixture, a solution of N,N-dimethylformamide (0.8 ml) of the compound (400 mg) produced in Example 17 was added at 0° C., and the mixture was stirred at 0° C. for 1 hour. To the mixture, an N,N-dimethylformamide (0.8 ml) solution of a tris(dibenzilideneacetone)dipalladium (0)-chloroform complex (73 mg), tris(2-methylphenyl)phosphine (171 mg) and methyl3-(3-iodophenyl)propanoate (408 mg) were added, and the mixture was stirred at 40° C. for 2 hours. The reaction mixture was diluted with ethyl acetate, and filtered with Celite (trade name). To the filtrate, 0.01N hydrochloric acid was added, followed by extraction with ethyl acetate. The extract was washed with brine, dried over anhydrous sodium sulfate, and concentrated. The residue was purified with silica gel column chromatography (hexane:ethyl acetate=50:1→20:1→12:1) to give the title compound (186 mg) having the following physical properties.

TLC: Rf 0.51 (hexane:ethyl acetate=9:1);
$^1$HNMR: δ −0.17 (s, 3H), 0.03 (s, 3H), 0.94 (m, 9H), 1.19 (m, 1H), 1.55 (m, 2H), 1.85 (m, 1H), 2.08 (s, 3H), 2.67 (m, 9H), 3.67 (m, 3H), 3.81 (m, 6H), 4.68 (d, 1H), 6.48 (s, 2H), 7.19 (m, 9H).

EXAMPLE 19 methyl3-(3-{(2S)-2-[(S)-(3,5-dimethoxy-4-methylphenyl)(hydroxy)methyl]-5-phenylpentyl}phenyl)propanoate To a tetrahydrofuran (1 ml) solution of the compound (186 mg) produced in Example 18, a tetrahydrofuran (2.66 ml) solution of 1.0M tetrabutylammonium fluoride was added at 0° C., and the mixture was stirred at room temperature for 2 hours. A saturated aqueous ammonium chloride solution was added to the reaction mixture, followed by extraction with ethyl acetate. The extract was washed with 0.01N hydrochloric acid, water and brine successively, dried over anhydrous sodium sulfate, and concentrated. The residue was purified with silica gel column chromatography (hexane:ethyl acetate=19:1→9:1→6:1) to give the title compound (129 mg) having the following physical properties.

TLC: Rf 0.25 (hexane:ethyl acetate=4:1);
$^1$HNMR: δ 1.52 (m, 5H), 2.09 (s, 3H), 2.45 (t, 2H), 2.63 (m, 3H), 2.82 (dd, 1H), 2.91 (t, 2H), 3.66 (s, 3H), 3.82(s, 6H), 4.59(d, 1H), 6.51 (s, 2H), 7.15(m, 9H).

EXAMPLE 20

3-(3-{(2S)-2-[(S)-(3,5-dimethoxy-4-methylphenyl)(hydroxy)methyl]-5-phenylpentyl}phenyl)propanoic acid

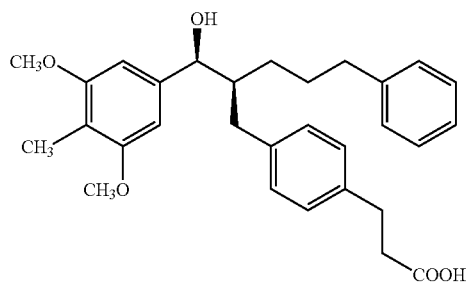

Using the compound produced in Example 19 instead of the compound produced in Example 4(1), procedures similar to Example 5(1) were carried out to give the title compound having the following physical properties.

TLC: Rf 0.13 (hexane:ethyl acetate=2:1);
$^1$HNMR: δ 1.26 (m, 2H), 1.58 (m, 2H), 2.04 (m, 4H), 2.45 (t, 2H), 2.61 (m, 3H), 2.79 (dd, 1H), 2.90 (t, 2H), 3.80 (s, 6H), 4.56 (d, 1H), 6.50 (s, 2H), 7.11 (m, 9H).

EXAMPLE 20(1) TO EXAMPLE 20(26)

Using 5-phenylpentanoyl chloride or a corresponding acid chloride derivative, 3,5-dimethoxy-4-methylbenzaldehyde or a corresponding aldehyde derivative, or methyl3-(3-iodophenyl)propanoate or a corresponding aryl halogen derivative, procedures similar to Example 12→Example 13→Example 14→Example 15→Example 16→Example 17→Example 18→Example 19→Example 20 were carried out to give each of the following compounds of the present invention.

EXAMPLE 20(1)

(4-{(2S)-2-[(S)-(3,5-dimethoxy-4-methylphenyl)(hydroxy)methyl]-5-phenylpentyl}phenyl)acetic acid TLC: Rf 0.45 (hexane:ethyl acetate=1:2);
$^1$HNMR: δ 7.24-7.03 (m, 9H), 6.50 (s, 2H), 4.59 (d, 1H), 3.81 (s, 6H), 3.63 (s, 2H), 2.82 (dd, 1H), 2.61 (dd, 1H), 2.45 (t, 2H), 2.09 (s, 3H), 2.04 (m, 1H), 1.75-1.10 (m, 4H).

EXAMPLE 20(2)

(4-{(2S)-2-[(S)-hydroxy(3,4,5-trimethoxyphenyl)methyl]-5-phenylpentyl}phenyl)acetic acid TLC: Rf 0.38 (dichloromethane:methanol=9:1);
$^1$HNMR: δ 7.26-7.02 (m, 9H), 6.53 (s, 2H), 4.57 (d, 1H), 3.84 (s, 3H), 3.84 (s, 6H), 3.62 (s, 2H), 2.80 (dd, 1H), 2.59 (dd, 1H), 2.46 (t, 2H), 2.05-1.96 (m, 1H), 1.67-1.14 (m, 4H).

EXAMPLE 20(3)

(3-{(2S)-2-[(S)-(3,5-dimethoxy-4-methylphenyl)(hydroxy)methyl]-5-phenylpentyl}phenyl)acetic acid TLC: Rf 0.44 (dichloromethane:methanol=9:1);
$^1$HNMR: δ 7.30-7.00 (m, 9H), 6.50 (s, 2H), 4.59 (d, 1H), 3.81 (s, 6H), 3.60 (s, 2H), 2.83 (dd, 1H), 2.60 (dd, 1H), 2.45 (t, 2H), 2.09 (s, 3H), 2.10-2.00 (m, 1H), 1.65-1.20 (m, 4H).

EXAMPLE 20(4)

3-(4-{(2S)-2-[(S)-(3,5-dimethoxy-4-methylphenyl)(hydroxy)methyl]-5-phenylpentyl}phenyl)propanoic acid TLC: Rf 0.15 (hexane:ethyl acetate=2:1);
$^1$HNMR: δ 1.28 (m, 2H), 1.58 (m, 2H), 2.02 (m, 1H), 2.09 (s, 3H), 2.45 (t, 2H), 2.62 (m, 3H), 2.80 (dd, 1H), 2.93 (t, 2H), 3.81 (s, 6H), 4.56 (d, 1H), 6.50 (s, 2H), 7.14 (m, 9H).

EXAMPLE 20(5)

{4-[(2S)-2-[(S)-(3,5-dimethoxy-4-methylphenyl)(hydroxy)methyl]-5-(2-thienyl)pentyl]phenyl}acetic acid TLC: Rf 0.45 (hexane:ethyl acetate=1:2);
$^1$HNMR: δ 7.18 (d, 2H), 7.11-7.06 (m, 3H), 6.86 (dd, 1H), 6.64 (dd, 1H), 6.50 (s, 2H), 4.61 (d, 1H), 3.81-3.75 (m, 6H), 3.62 (s, 2H), 2.83 (dd, 1H), 2.69-2.57 (m, 3H), 2.10-1.98 (m, 4H), 1.72-1.57 (m, 2H), 1.44-1.15 (m, 2H).

EXAMPLE 20(6)

(4-{(2S)-2-[(S)-(3,5-dimethoxyphenyl)(hydroxy)methyl]-5-phenylpentyl}phenyl)acetic acid TLC: Rf 0.42 (dichloromethane:methanol=9:1);
$^1$HNMR: δ 7.26-7.03 (m, 9H), 6.49 (d, 2H), 6.37 (t, 1H), 4.62 (d, 1H), 3.79 (s, 6H), 3.62 (s, 2H), 2.79 (dd, 1H), 2.55 (dd, 1H), 2.46 (t, 2H), 2.08-1.96 (m, 1H), 1.69-1.16 (m, 4H).

EXAMPLE 20(7)

(3-{(2S)-2-[(S)-(3,5-dimethoxy-4-methylphenyl)(hydroxy)methyl]-5-phenylpentyl}phenoxy)acetic acid TLC: Rf 0.22 (dichloromethane:methanol=9:1);
$^1$HNMR: δ 1.27 (m, 2H), 1.58 (m, 2H), 2.04 (m, 4H), 2.46 (t, 2H), 2.60 (m, 1H), 2.81 (m, 10H), 3.81 (s, 6H), 4.59 (m, 3H), 6.49 (s, 2H), 6.74 (m, 3H), 7.16 (m, 6H).

EXAMPLE 20(8)

(4-{(2S)-2-[(S)-(3,5-dimethoxy-4-methylphenyl)(hydroxy)methyl]-5-phenylpentyl}phenoxy)acetic acid TLC: Rf 0.17 (dichloromethane:methanol=9:1);
$^1$HNMR: δ 1.25 (m, 2H), 1.57 (m, 2H), 1.98 (m, 1H), 2.08 (s, 3H), 2.44 (t, 2H), 2.59 (m, 1H), 2.77 (m, 1H), 3.80 (s, 6H), 4.56 (d, 1H), 4.65 (s, 2H), 6.49 (s, 2H), 6.81 (m, 2H), 7.05 (m, 4H), 7.20 (m, 3H).

EXAMPLE 20(9)

4-{(2S)-2-[(S)-(3,5-dimethoxy-4-methylphenyl)(hydroxy)methyl]-5-phenylpentyl}benzoic acid TLC: Rf 0.42 (dichloromethane:methanol=9:1);
$^1$HNMR: δ 8.01-7.95 (m, 2H), 7.25-7.10 (m, 5H), 7.06-7.00 (m, 2H), 6.50 (s, 2H), 4.59 (d, 1H), 3.81 (s, 6H), 2.92 (dd, 1H), 2.69 (dd, 1H), 2.45 (t, 2H), 2.09 (s, 3H), 2.11-2.01 (m, 1H), 1.70-1.09 (m, 4H).

EXAMPLE 20(10)

{4-[(2S)-2-[(S)-(3,5-dimethoxy-4-methylphenyl)(hydroxy)methyl]-5-(3-thienyl)pentyl]phenyl}acetic acid TLC: Rf 0.31 (hexane:ethyl acetate:acetic acid=2:1:0.1);
$^1$ HNMR: δ 1.29 (m, 2H), 1.56 (m, 2H), 2.04 (m, 1H), 2.08 (s, 3H), 2.46 (t, 2H), 2.58 (m, 1H), 2.82 (dd, 1H), 3.60 (s, 2H), 3.80 (s, 6H), 4.59 (d, 1H), 6.49 (s, 2H), 6.78 (m, 2H), 7.08 (d, 2H), 7.17 (m, 3H).

EXAMPLE 20(11)

3-{(2S)-2-[(S)-(3,5-dimethoxy-4-methylphenyl)(hydroxy)methyl]-5-phenylpentyl}benzoic acid TLC: Rf 0.52 (dichloromethane:methanol=9:1);
$^1$HNMR: δ 7.97-7.91 (m, 2H), 7.37-7.01 (m, 7H), 6.50 (s, 2H), 4.60 (d, 1H), 3.81 (s, 6H), 2.91 (dd, 1H), 2.69 (dd, 1H), 2.45 (t, 2H), 2.08 (s, 3H), 2.12-2.03 (m, 1H), 1.70-1.13 (m, 4H).

EXAMPLE 20(12)

2-(4-{(2S)-2-[(S)-(3,5-dimethoxy-4-methylphenyl)(hydroxy)methyl]-5-phenylpentyl}phenoxy)-2-methylpropanoic acid TLC: Rf 0.60 (dichloromethane:methanol=9:1);
$^1$HNMR: δ 7.25-7.15 (m, 3H), 7.10-7.00 (m, 4H), 6.83 (d, 2H), 6.49 (s, 2H), 4.58 (d, 1H), 3.81 (s, 6H), 2.80 (dd, 1H), 2.56 (dd, 1H), 2.45 (t, 2H), 2.08 (s, 3H), 2.05-1.90 (m, 1H), 1.56 (s, 6H), 1.60-1.10 (m, 4H).

EXAMPLE 20(13)

2-(4-{(2S)-2-[(S)-(3,5-dimethoxy-4-methylphenyl)(hydroxy)methyl]-5-phenylpentyl}phenoxy)benzoic acid TLC: Rf 0.20 (hexane:ethyl acetate=2:1);
$^1$HNMR: δ 8.22 (dd, 1H), 7.48-7.42 (m, 1H), 7.26-7.13 (m, 6H), 7.08-7.04 (m, 2H), 7.00-6.96 (m, 2H), 6.79 (dd, 1H), 6.50 (s, 2H), 4.61 (d, 1H), 3.82 (s, 6H), 2.88 (dd, 1H), 2.64 (dd, 1H), 2.48 (t, 2H), 2.10-1.98 (m, 4H), 1.66-1.54 (m, 2H), 1.44-1.15 (m, 2H).

EXAMPLE 20(14)

2-(4-{(2S)-2-[(S)-(3,5-dimethoxy-4-methylphenyl)(hydroxy)methyl]-5-phenylpentyl}phenyl)-2-methylpropanoic acid TLC: Rf 0.25 (hexane:ethyl acetate=2:1);
$^1$HNMR: δ 7.30-7.03 (m, 9H), 6.50 (s, 2H), 4.60 (d, 1H), 3.81 (s, 6H), 2.82 (dd, 1H), 2.58 (dd, 1H), 2.45 (t, 2H), 2.08 (s, 3H), 2.10-2.00 (m, 1H), 1.70-1.20 (m, 4H), 1.59 (s, 6H).

EXAMPLE 20(15)

(4-{(2S)-2-[(S)-(2-chloro-4,5-dimethoxyphenyl)(hydroxy)methyl]-5-phenylpentyl}phenyl)acetic acid TLC: Rf 0.24 (hexane:ethyl acetate=1:4);
$^1$HNMR: δ 7.26-6.94 (m, 10H), 6.81 (s, 1H), 5.13 (d, 1H), 3.86 (s, 3H), 3.85 (s, 3H), 3.58 (s, 2H), 2.81 (dd, 1H), 2.56-2.36 (m, 3H), 2.19-2.05 (m, 1H), 1.77-1.24 (m, 4H).

EXAMPLE 20(16)

(4-{(2S)-2-[(S)-(3,4-dimethoxyphenyl)(hydroxy)methyl]-5-phenylpentyl}phenyl)acetic acid TLC: Rf 0.50 (dichloromethane:methanol=9:1);
$^1$HNMR: δ 1.24 (m, 2H), 1.57 (m, 2H), 2.02 (m, 1H), 2.43 (t, 2H), 2.59 (dd, 1H), 2.81 (m, 1H), 3.62 (s, 2H), 3.87 (s, 3H), 3.89 (s, 3H), 4.58 (d, 1H), 6.84 (m, 3H), 7.15 (m, 9H).

EXAMPLE 20(17)

(4-{(2R)-2-[(S)-(3,5-dimethoxy-4-methylphenyl)(hydroxy)methyl]-4-phenoxybutyl}phenyl)acetic acid TLC: Rf 0.17 (hexane:ethyl acetate=1:1);
$^1$HNMR: δ 1.79 (m, 2H), 2.08 (s, 3H), 2.30 (d, 1H), 2.61 (m, 1H), 2.85 (dd, 1H), 3.60 (m, 2H), 3.87 (m, 8H), 4.78 (d, 1H), 6.55 (s, 2H), 6.78 (dd, 2H), 6.92 (m, 1H), 7.19 (m, 6H).

EXAMPLE 20(18)

(4-{(2S)-2-[(S)-(3-chloro-2-thienyl)(hydroxy)methyl]-5-phenylpentyl}phenyl)acetic acid TLC: Rf 0.32 (hexane:ethyl acetate=1:1);
$^1$HNMR: δ 7.26-7.00 (m, 10H), 6.90-6.86 (m, 1H), 5.09 (d, 1H), 3.60 (s, 2H), 2.95 (dd, 1H), 2.60-2.37 (m, 3H), 2.25-2.11 (m, 1H), 1.71-1.20 (m, 4H).

EXAMPLE 20(19)

(4-{(2S)-2-[(S)-(2,6-dimethoxy-3-pyridinyl)(hydroxy)methyl]-5-phenylpentyl}phenyl)acetic acid TLC: Rf 0.34 (hexane:ethyl acetate=1:1);
$^1$HNMR: δ 7.48 (d, 1H), 7.24-7.00 (m, 9H), 6.27 (d, 1H), 4.76 (d, 1H), 3.92 (s, 3H), 3.90 (s, 3H), 3.58 (s, 2H), 2.84 (dd, 1H), 2.55-2.34 (m, 3H), 2.18-2.09 (m, 1H), 1.66-1.12 (m, 4H).

EXAMPLE 20(20)

4-(4-{(2S)-2-[(S)-(3,5-dimethoxy-4-methylphenyl)(hydroxy)methyl]-5-phenylpentyl}phenyl)butanoic acid TLC: Rf 0.26 (hexane:ethyl acetate=2:1);
$^1$HNMR: δ 7.20-7.00 (m, 9H), 6.50 (s, 2H), 4.60 (d, 1H), 3.81 (s, 6H), 2.80 (dd, 1H), 2.64 (t, 2H), 2.58 (dd, 1H), 2.45 (t, 2H), 2.37 (t, 2H), 2.09 (s, 3H), 2.05-1.90 (m, 3H), 1.70-1.10 (m, 4H).

EXAMPLE 20(21)

(4-{(2S)-2-[(S)-2,3-dihydro-1,4-benzodioxin-6-yl(hydroxy)methyl]-5-phenylpentyl}phenyl)acetic acid TLC: Rf 0.48 (dichloromethane:methanol=9:1);
$^1$HNMR: δ 1.25 (m, 2H), 1.57 (m, 2H), 1.99 (m, 1H), 2.44 (t, 2H), 2.55 (dd, 1H), 2.79 (dd, 1H), 3.60 (s, 2H), 4.25 (s, 4H), 4.55 (d, 1H), 6.77 (dd, 1H), 6.82 (m, 1H), 6.86 (d, 1H), 7.15 (m, 9H).

EXAMPLE 20(22)

(4-{(2S)-2-[(S)-[4-(difluoromethoxy)phenyl](hydroxy)methyl]-5-phenylpentyl}phenyl)acetic acid TLC: Rf 0.26 (hexane:ethyl acetate=1:1);
$^1$HNMR: δ 7.34-7.02 (m, 13H), 6.50 (t, 1H), 4.67 (d, 1H), 3.61 (s, 2H), 2.74 (dd, 1H), 2.56 (dd, 1H), 2.45 (t 2H), 2.07-1.95 (m, 1H), 1.66-1.11 (m, 4H).

EXAMPLE 20(23)

(4-{(2S)-2-[(S)-hydroxy(4-methoxy-3,5-dimethylphenyl)methyl]-5-phenylpentyl}phenyl)acetic acid TLC: Rf 0.43 (hexane:ethyl acetate=1:1);
$^1$HNMR: δ 7.25-7.01 (m, 9H), 6.94 (s, 2H), 4.54 (d, 1H), 3.71 (s, 3H), 3.60 (s, 2H), 2.82 (dd, 1H), 2.55 (dd, 1H), 2.43 (t, 2H), 2.67 (s, 6H), 2.06-1.95 (m, 1H), 1.66-1.10 (m, 4H).

EXAMPLE 20(24)

(4-{(2S)-2-[(S)-[3-(cyclopentyloxy)-4-methoxyphenyl](hydroxy)methyl]-5-phenylpentyl}phenyl)acetic acid TLC: Rf 0.30 (hexane:ethyl acetate=1:1);
$^1$HNMR: δ 7.25-7.00 (m, 9H), 6.87-6.80 (m, 3H), 4.80-4.73 (m, 1H), 4.56 (d, 1H), 3.84 (s, 3H), 3.61 (s, 2H), 2.81 (dd, 1H), 2.57 (dd, 1H), 2.43 (t, 2H), 2.04-1.75 (m, 7H), 1.65-1.49 (m, 4H), 1.40-1.10 (m, 2H).

EXAMPLE 20(25)

(4-{(2S)-2-[(S)-(3,5-dimethoxy-4-methylphenyl)(hydroxy)methyl]-4-phenylbutyl}phenyl)acetic acid TLC: Rf 0.45 (hexane:ethyl acetate=1:2);
$^1$HNMR: δ 7.22-7.09 (m, 7H), 6.99-6.95 (m, 2H), 6.47 (s, 2H), 4.64 (d, 1H), 3.79 (s, 6H), 3.63 (s, 2H), 2.87 (dd, 1H), 2.67 (dd, 1H), 2.55 (t, 2H), 2.10-1.99 (m, 4H), 1.69-1.43 (m, 2H).

EXAMPLE 20(26)

{4-[(2S,3S)-2-(2,3-dihydro-1H-inden-2-ylmethyl)-3-(3,5-dimethoxy-4-methylphenyl)-3-hydroxypropyl]phenyl}acetic acid TLC: Rf 0.40 (dichloromethane:methanol=9:1);
$^1$HNMR: δ 7.22-7.04 (m, 8H), 6.53 (s, 2H), 4.64 (d, 1H), 3.82 (s, 6H), 3.62 (s, 2H), 3.00-2.90 (m, 2H), 2.82 (dd 1H), 2.70 (dd, 1H), 2.62-2.28 (m, 3H), 2.18 (m, 1H), 2.07 (s, 3H), 1.70-1.30 (m, 2H).

EXAMPLE 21

(4-{(2R)-2-[(R)-(3,5-dimethoxy-4-methylphenyl)(hydroxy)methyl]-4-phenylbutyl}phenyl)acetic acid Using (4R)-4-benzyl-1,3-oxazolidin-2-one instead of (4S)-4-benzyl-1,3-oxazolidin-2-one, 4-phenylbutanoyl chloride instead of 5-phenylpentanoyl chloride and methyl(4-iodophenyl)acetate instead of methyl3-(3-iodophenyl)propanoate, procedures similar to Example 12→Example 13→Example 14→Example 15→Example 16→Example 17 Example 18→Example 19→Example 20 were carried out to give the title compound having the following physical properties.

TLC: Rf 0.41 (hexane:ethyl acetate=1:2);
$^1$HNMR: δ 7.22-7.09 (m, 7H), 7.00-6.95 (m, 2H), 6.47 (s, 2H), 4.64 (d, 1H), 3.79 (s, 6H), 3.62 (s, 2H), 2.87 (dd, 1H), 2.67 (dd, 1H), 2.54 (t, 2H), 2.10-1.98 (m, 4H), 1.69-1.42 (m, 2H).

EXAMPLE 22 methyl2-({(2S)-2-[(S)-{[tert-butyl(dimethyl)silyl]oxy}(3,5-dimethoxy-4-methylphenyl)methyl]-5-phenylpentyl}oxy)benzoate Using the compound of Example 15 instead of (±)-(1R*,2R*)-1-(3,5-dimethoxy-4-methylphenyl)-1-(methoxymethoxy)-5-phenylpentan-2-ol, and methyl 2-hydroxybenzoate instead of methyl2-(4-hydroxyphenoxy)-4-methylbenzoate, procedures similar to Example 6 were carried out to give the title compound having the following properties.

TLC: Rf 0.73 (hexane: diethyl ether =4:1).

EXAMPLE 23

2-({(2S)-2-[(S)-(3,5-dimethoxy-4-methylphenyl)(hydroxy)methyl]-5-phenylpentyl}oxy)benzoic acid Using the compound produced in Example 22 instead of the compound produced in Example 18, procedures similar to Example 19→Example 20 were carried out to give the title compound having the following physical properties.

TLC: Rf 0.64 (hexane:ethyl acetate=1:2);
$^1$HNMR: δ 1.73 (m, 4H), 2.04 (s, 3H), 2.10 (m, 1H), 2.62 (m, 2H), 3.66 (s, 6H), 4.12 (m, 2H), 4.87 (d, 1H), 6.46 (s, 2H), 6.89 (d, 1H), 7.17 (m, 6H), 7.48 (m, 1H), 8.13 (d, 1H).

EXAMPLE 23(1) TO EXAMPLE 23(4)

Using a corresponding phenol derivative instead of methyl2-hydroxybenzoate, procedures similar to Example 22→Example 23 were carried out to give each of the following compounds of the present invention.

EXAMPLE 23(1)

3-({(2S)-2-[(S)-(3,5-dimethoxy-4-methylphenyl)(hydroxy)methyl]-5-phenylpentyl}oxy)benzoic acid TLC: Rf 0.098 (dichloromethane:methanol=9:1);
$^1$HNMR: δ 7.70 (d, 1H), 7.61 (m, 1H), 7.42-7.06 (m, 7H), 6.49 (s, 2H), 4.83 (d, 1H), 4.20 (dd, 1H), 4.03 (dd, 1H), 3.74 (s, 6H), 2.58 (m, 2H), 2.15 (m, 1H), 2.07 (s, 3H), 1.95-1.20 (m, 4H).

EXAMPLE 23(2)

4-({(2S)-2-[(S)-(3,5-dimethoxy-4-methylphenyl)(hydroxy)methyl]-5-phenylpentyl}oxy)benzoic acid TLC: Rf 0.64 (hexane:ethyl acetate=1:2);
$^1$HNMR: δ 1.59 (m, 4H), 2.08 (s, 3H), 2.14 (m, 1H), 2.60 (m, 2H), 3.75 (s, 6H), 4.05 (dd, 1H), 4.22 (dd, 1H), 4.81 (d, 1H), 6.48 (s, 2H), 6.93 (d, 2H), 7.18 (m, 5H), 8.04 (d, 2H).

EXAMPLE 23(3)

[3-({(2S)-2-[(S)-(3,5-dimethoxy-4-methylphenyl)(hydroxy)methyl]-5-phenylpentyl}oxy)phenyl]acetic acid TLC: Rf 0.31 (dichloromethane:methanol=9:1);
$^1$HNMR: δ 7.32-7.08 (m, 6H), 6.92-6.78 (m, 3H), 6.47 (s, 2H), 4.82 (d, 1H), 4.12 (dd, 1H), 3.95 (dd, 1H), 3.72 (s, 6H), 3.61 (s, 2H), 2.62-2.50 (m, 2H), 2.08-1.20 (m, 5H), 2.07 (s, 3H).

EXAMPLE 23(4)

[4-({(2S)-2-[(S)-(3,5-dimethoxy-4-methylphenyl)(hydroxy)methyl]-5-phenylpentyl}oxy)phenyl]acetic acid TLC: Rf 0.33 (dichloromethane:methanol=9:1);
$^1$HNMR: δ 7.30-7.08 (m, 7H), 6.86 (d, 2H), 6.47 (s, 2H), 4.81 (d, 1H), 4.10 (dd, 1H), 3.94 (dd, 1H), 3.72 (s, 6H), 3.59 (s, 2H), 2.62-2.50 (m, 2H), 2.08 (m, 1H), 2.07 (s, 3H), 1.80-1.20 (m, 4H).

EXAMPLE 24 ethyl1-{(2S)-2-[(S)-{[tert-butyl(dimethyl)silyl]oxy}(3,5-dimethoxy-4-methylphenyl)methyl]-5-phenylpentyl}-1H-pyrrole-2-carboxylate To a dimethylformamide (2 ml) solution of 60% sodium hydride (24 mg), an N,N-dimethylformamide (2 ml) solution of ethyl1H-pyrrole-2-carboxylate (78 mg) was added under argon atmosphere. The mixture was stirred at 50° C. for 30 minutes. To the mixture, the compound (200 mg) produced in Example 16 was added at room temperature. The reaction mixture was stirred at 50° C. for 15 hours. To the reaction mixture, 1N hydrochloric acid was added at room temperature, followed by extraction with ethyl acetate. The extract was washed with water and brine successively, dried over with anhydrous sodium sulfate, and concentrated. The residue was purified with silica gel column chromatography (hexane:ethyl acetate=10:1) to give the title compound (166 mg) having the following physical properties.

TLC: Rf 0.58 (hexane:ethyl acetate=4:1);

$^1$HNMR: δ 7.26-7.02 (m, 5H), 6.91 (dd, 1H), 6.66 (dd, 1H), 6.46 (s, 2H), 6.06 (dd, 1H), 4.71 (d, 1H), 4.37 (dd, 1H), 4.27 (dd, 1H), 4.17 (q, 2H), 3.79 (s, 6H), 2.42 (m, 2H), 2.07 (s, 3H), 1.60-1.00 (m, 4H), 1.27 (t, 3H), 0.95 (s, 9H), 0.05 (s, 3H), –0.15 (s, 3H).

EXAMPLE 25

1-{(2S)-2-[(S)-(3,5-dimethoxy-4-methylphenyl)(hydroxy)methyl]-5-phenylpentyl}-1H-pyrrole-2-caboxylic acid Using the compound produced in Example 24 instead of the compound produced in Example 18, procedures similar to Example 19→Example 20 were carried out to give the title compound having the following properties.

TLC: Rf 0.49 (dichloromethane:methanol=9:1);

$^1$HNMR: δ 7.26-7.00 (m, 6H), 6.79 (dd, 1H), 6.47 (s, 2H), 6.11 (dd, 1H), 4.65-4.55 (m, 2H), 4.26 (dd, 1H), 3.80 (s, 6H), 2.42 (m, 2H), 2.30 (m, 1H), 2.08 (s, 3H), 1.58-1.08 (m, 4H).

EXAMPLE 25(1) TO EXAMPLE 25(4)

Using a corresponding heterocyclic ring derivative instead of ethyl1H-pyrrole-2-carboxylate, procedures similar to Example 24→Example 25 were carried out to give each of the compounds of the present invention.

EXAMPLE 25(1)

1-{(2S)-2-[(S)-(3,5-dimethoxy-4-methylphenyl)(hydroxy)methyl]-5-phenylpentyl}-1H-pyrazole-4-carboxylic acid TLC: Rf 0.19 (dichloromethane:methanol=9:1);

$^1$HNMR: δ 7.97 (s, 1H), 7.84 (s, 1H), 7.30-7.04 (m, 5H), 6.50 (s, 2H), 4.48-4.38 (m, 2H), 4.22 (dd, 1H), 3.81 (s, 6H), 2.60-2.40 (m, 2H), 2.22 (m, 1H), 2.08 (s, 3H), 1.80-1.10 (m, 4H).

EXAMPLE 25(2)

1-{(2S)-2-[(S)-(3,5-dimethoxy-4-methylphenyl)(hydroxy)methyl]-5-phenylpentyl}-1H-pyrazole-3-carboxylic acid TLC: Rf 0.66 (hexane:ethyl acetate=1:3);

$^1$HNMR: δ 1.25 (m, 2H), 1.58 (m, 2H), 1.99 (m, 1H), 2.09 (s, 3H), 2.47 (m, 2H), 3.81 (s, 6H), 4.03 (dd, 1H), 4.14 (m, 1H), 4.40 (d, 1H), 6.45 (s, 2H), 6.53 (m, 1H), 6.59 (m, 1H), 7.05 (m, 2H), 7.21 (m, 3H), 7.36 (t, 1H).

EXAMPLE 25(3)

(1-{(2S)-2-[(S)-(3,5-dimethoxy-4-methylphenyl)(hydroxy)methyl]-5-phenylpentyl}-1H-imidazol-4-yl)acetic acid TLC: Rf 0.16 (dichloromethane:methanol=9:1);

$^1$HNMR: δ 8.00 (brs, 1H), 7.28-7.10 (m, 3H), 7.03-6.97 (m, 2H), 6.68 (brs, 1H), 6.45 (s, 2H), 4.30 (m, 1H), 4.20-3.95 (m, 2H), 3.75 (s, 6H), 3.74-3.50 (m, 2H), 2.60-2.20 (m, 3H), 2.05 (s, 3H), 1.80-1.20 (m, 4H).

EXAMPLE 25(4)

(1-{(2S)-2-[(S)-(3,5-dimethoxy-4-methylphenyl)(hydroxy)methyl]-5-phenylpentyl}-3,5-dimethyl-1H-pyrazol-4-yl)acetic acid TLC: Rf 0.38 (dichloromethane:methanol=4:1);

$^1$HNMR: 67.28-7.12 (m, 3H), 7.08-7.02 (m, 2H), 6.56 (s, 2H), 4.55 (d, 1H), 4.07 (dd, 1H), 3.94 (dd, 1H), 3.80 (s, 6H), 3.34 (s, 2H), 2.62-2.40 (m, 2H), 2.19 (s, 3H), 2.15 (m, 1H), 2.07 (s, 6H), 1.70-1.55 (m, 2H), 1.45-1.10 (m, 2H).

EXAMPLE 26

(1-{(2S)-2-[(S)-{[tert-butyl(dimethyl)silyl]oxy}(3,5-dimethoxy-4-methylphenyl)methyl]-5-phenylpentyl}-1H-pyrrol-3-yl)acetonitrile Using 1H-pyrrol-3-ylacetonitrile instead of ethyl1H-pyrrole-2-carboxylate, procedures similar to Example 24 was carried out to give the title compound having the following physical properties.

TLC: Rf 0.39 (hexane:ethyl acetate=4:1);

$^1$HNMR: δ –0.19 (s, 3H), 0.04 (s, 3H), 0.94 (s, 9H), 1.13 (m, 1H), 1.42 (m, 2H), 1.64 (m, 1H), 1.92 (m, 1H), 2.08 (s, 3H), 2.46 (m, 2H), 3.52 (s, 2H), 3.65 (dd, 1H), 3.80 (s, 6H), 3.97 (dd, 1H), 4.65 (d, 1H), 6.00 (m, 1H), 6.44 (m, 4H), 7.07 (m, 2H), 7.22 (m, 3H).

EXAMPLE 27

(1-{(2S)-2-[(S)-(3,5-dimethoxy-4-methylphenyl)(hydroxy)methyl]-5-phenylpentyl}-1H-pyrrol-3-yl)acetic acid To an ethanol (2 ml) solution of the compound (95 mg) produced in Example 26, a 5N aqueous sodium hydroxide solution (1 ml) was added, and the mixture was allowed to react with a microwave of 80 W at 150° C. and 15 bar for 45 minutes. To the reaction mixture, 1N hydrochloric acid was added, followed by extraction with ethyl acetate. The extract was washed with brine, dried over anhydrous magnesium sulfate, and concentrated. The residue was purified with silica gel column chromatography (hexane:ethyl acetate=2:1) to give the title compound (75 mg) having the following physical properties.

TLC: Rf 0.46 (hexane:ethyl acetate=1:2);

$^1$HNMR: δ 1.18 (m, 2H), 1.54 (m, 2H), 1.98 (m, 1H), 2.08 (s, 3H), 2.47 (m, 2H), 3.50 (s, 2H), 3.80 (s, 6H), 3.96 (dd, 1H), 4.05 (dd, 1H), 4.41 (d, 1H), 6.06 (m, 1H), 6.46 (s, 2H), 6.55 (m, 2H), 7.05 (m, 2H), 7.21 (m, 3H).

EXAMPLE 28

(1-{(2S)-2-[(S)-(3,5-dimethoxy-4-methylphenyl)(hydroxy)methyl]-5-phenylpentyl}-1H-indol-3-yl)acetic acid Using 1H-indol-3-ylacetic acid instead of ethyl1H-pyrrole-2-carboxylate, procedures similar to Example 24→Example 19 were carried out to give the title compound having the following physical properties.

TLC: Rf 0.16 (hexane:ethyl acetate=1:1);

$^1$HNMR: δ 1.47 (m, 4H), 2.09 (s, 3H), 2.22 (m, 1H), 2.42 (t, 2H), 3.76 (s, 2H), 3.78 (s, 6H), 4.12 (dd, 1H), 4.28 (dd, 1H), 4.65 (d, 1H), 6.48 (s, 2H), 6.99 (m, 3H), 7.15 (m, 6H), 7.57 (d, 1H).

EXAMPLE 29

(1-{(2S)-2-[(S)-{[tert-butyl(dimethyl)silyl]oxy}(3,5-dimethoxy-4-methylphenyl)methyl]-5-phenylpentyl}-1H-pyrazol-4-yl)methanol To a tetrahydrofuran (1 ml) solution of lithium aluminumhydride (15 mg), a tetrahydrofuran (1 ml) solution of ethyl1-{(2S)-2-[(S)-{[tert-butyl(dimethyl)silyl]oxy}(3,5-dimethoxy-4-methylphenyl)methyl]-5-phenylpentyl}-1H-pyrazole-4-carboxylate (produced by a method similar to Example 24 using the compound produced in Example 16 and ethyl1H-pyrazole-4-carboxylate) (40 mg) was added, and the mixture was stirred at room temperature for 15 minutes. To the reaction mixture, a saturated aqueous sodium sulfate solution, anhydrous magnesium sulfate and ethyl acetate were added successively, and the mixture was stirred at room temperature for 20 minutes. The mixture was filtered, and the filtrate was concentrated to give the title compound (35 mg) having the following physical properties.

TLC: Rf 0.23 (hexane:ethyl acetate=2:1);
$^1$HNMR: δ 7.42 (s, 1H), 7.30-7.05 (m, 6H), 6.45 (s, 2H), 4.72 (d, 1H), 4.50 (d, 2H), 4.21 (dd, 1H), 3.94 (dd, 1H), 3.79 (s, 6H), 2.50 (m, 2H), 2.20 (m., 1H), 2.06 (s, 3H), 1.78-1.12 (m, 4H), 0.94 (s, 9H), 0.04 (s, 3H), −0.16 (s, 3H).

EXAMPLE 30

1-{(2S)-2-[(S)-{[tert-butyl(dimethyl)silyl]oxy}(3,5-dimethoxy-4-methylphenyl)methyl]-5-phenylpentyl}-4-(chloromethyl)-1H-pyrazole To a tetrahydrofuran (2 ml) solution of the compound (100 mg) produced in Example 29, triethylamine (52 μl), lithium chloride (15.8 mg) and methanesulfonyl chloride (22 μl) were added at 0° C., and the mixture was stirred at 0° C. for 2 hours and at room temperature for 1 hour. The reaction mixture was diluted with ethyl acetate, and then filtered. The filtrate was concentrated to give the title compound having the following physical properties.

TLC: Rf 0.70 (hexane:ethyl acetate=2:1);
$^1$HNMR: δ 7.44 (s, 1H), 7.28-7.04 (m, 6H), 6.45 (s, 2H), 4.69 (m, 1H), 4.49 (s, 2H), 4.21 (dd, 1H), 3.95 (dd, 1H), 3.79 (s, 6H), 2.50 (m, 2H), 2.18 (m, 1H), 2.06 (s, 3H), 1.70-1.08 (m, 4H), 0.94 (s, 9H), 0.03 (s, 3H), −0.171 (s, 3H).

EXAMPLE 31

(1-{(2S)-2-[(S)-{[tert-butyl(dimethyl)silyl]oxy}(3,5-dimethoxy-4-methylphenyl)methyl]-5-phenylpentyl}-1H-pyrazol-4-yl)acetonitrile To a dimethylsulfoxide (2 ml) solution of the compound produced in Example 30, sodium cyanide (46 mg) was added, and the mixture was stirred at room temperature for 20 minutes. Water was added to the reaction mixture, followed by extraction with ethyl acetate. The extract was washed with water and brine successively, dried over with anhydrous sodium sulfate, and concentrated to give the title compound (88 mg) having the following physical properties.

TLC: Rf 0.49 (hexane:ethyl acetate=2:1);
$^1$HNMR: δ 7.37 (s, 1H), 7.30-7.05 (m, 6H), 6.45 (s, 2H), 4.72 (d, 1H), 4.21 (dd, 1H), 3.96 (dd, 1H), 3.80 (s, 6H), 3.52 (s, 2H), 2.50 (m, 2H), 2.07 (s, 3H), 1.75-1.02 (m, 4H), 0.94 (s, 9H), 0.04 (s, 3H), −0.17 (s, 3H).

EXAMPLE 32

(1-{(2S)-2-[(S)-(3,5-dimethoxy-4-methylphenyl)(hydroxy)methyl]-5-phenylpentyl}-1H-pyrazol-4-yl)acetic acid To an ethanol solution of the compound produced in Example 31, a 5N aqueous sodium hydroxide solution was added, and the mixture was stirred at 80° C. for 2 hours. The reaction mixture was added to 1N hydrochloric acid, followed by extraction with ethyl acetate. The extract was washed with brine, dried over anhydrous magnesium sulfate, and concentrated. The residue was purified with silica gel column chromatography to give the title compound having the following physical properties.

TLC: Rf 0.45 (chloroform:methanol=9:1);
$^1$HNMR: δ 7.46 (s, 1H), 7.28-7.05 (m, 6H), 6.52 (s, 2H), 4.42-4.35 (m, 2H), 4.06 (dd, 1H), 3.80 (s, 6H), 3.52 (s, 2H), 2.62-2.38 (m, 2H), 2.15 (m, 1H), 2.07 (s, 3H), 1.85-1.02 (m, 4H).

EXAMPLE 33

1-{(2S)-2-[(S)-{[tert-butyl(dimethyl)silyl]oxy}(3,5-dimethoxy-4-methylphenyl)methyl]-5-phenylpentyl}-1H-pyrazole-4-carbaldehyde To an ethyl acetate (1 ml)-dimethylsulfoxide (1 ml) solution of the compound (160 mg) produced in Example 29, triethylamine (248 μl) and a sulfur trioxide - pyridine complex (142 mg) were added, and the mixture was stirred at room temperature for 1 hour. The reaction mixture was diluted with ethyl acetate. The extract was washed with water and brine successively, dried over anhydrous sodium sulfate, and concentrated to give the title compound (274 mg) having the following physical properties.

TLC: Rf 0.50 (hexane:diethyl ether =4:1);
$^1$HNMR: δ 9.78 (s, 1H), 7.88 (s, 1H), 7.67 (s, 1H), 7.28-7.03 (m, 5H), 6.44 (s, 2H), 4.74 (d, 1H), 4.26 (dd, 1H), 4.02 (dd, 1H), 3.79 (s, 6H), 2.54-2.44 (m, 2H), 2.19 (m, 1H), 2.06 (s, 3H), 1.76-1.39 (m, 3H), 1.12 (m, 1H), 0.95 (s, 9H), 0.04 (s, 3H), −0.16 (s, 3H).

EXAMPLE 34 ethyl(2E)-3-(1-{(2S)-2-[(S)-{[tert-butyl(dimethyl)silyl]oxy}(3,5-dimethoxy-4-methylphenyl)methyl]-5-phenylpentyl}-1H-pyrazol-4-yl)acrylate To a tetrahydrofuran (0.5 ml) solution of ethyl2-(diethoxyphosphoryl)acetate (100 mg), sodium hydride (10.7 mg) was added under argon atmosphere at 0° C. The mixture was stirred for 10 minutes, a tetrahydrofuran (1.5 ml) solution of the compound (274 mg) produced in Example 33, and the mixture was stirred at room temperature for 30 minutes. Water was added to the reaction mixture, followed by extraction with ethyl acetate. The extract was washed with water and brine successively, dried over anhydrous sodium sulfate, and concentrated. The residue was purified with silica gel column chromatography (hexane:ethyl acetate=9:1 4:1) to give the title compound (112 mg) having the following physical properties.

TLC: Rf 0.56 (hexane:diethyl ether =4:1);
$^1$HNMR: δ 7.63 (s, 1H), 7.49 (d, 1H), 7.30 (s, 1H), 7.27-7.12 (m, 3H), 7.10-7.03 (m, 2H), 6.45 (s, 2H), 6.12 (d, 1H), 4.71 (d, 1H), 4.28-4.17 (m, 3H), 3.97 (dd, 1H), 3.79 (s, 6H), 2.52-2.42 (m, 2H), 2.17 (m, 1H), 2.06 (s, 3H), 1.71-1.37 (m, 3H), 1.32 (t, 3H), 1.12 (m, 1H), 0.94 (s, 9H), 0.03 (s, 3H), −0.17 (s, 3H).

EXAMPLE 35

(2E)-3-(1-{(2S)-2-[(S)-(3,5-dimethoxy-4-methylphenyl)(hydroxy)methyl]-5-phenylpentyl}-1H-pyrazol-4-yl)acrylic acid Using the compound produced in Example 34 instead of the compound produced in Example 18, procedures similar to Example 19→Example 20 were carried out to give the title compound having the following physical properties.

TLC: Rf 0.35 (hexane:ethyl acetate=1:3);
$^1$HNMR: δ 1.20 (m, 2H), 1.65 (m, 2H), 2.08 (s, 3H), 2.16 (m, 1H), 2.45 (m, 1H), 2.58 (m, 1H), 3.81 (s, 6H), 4.15 (dd, 1H), 4.35 (d, 1H), 4.41 (dd, 1H), 6.15 (d, 1H), 6.50 (s, 2H), 7.08 (m, 2H), 7.24 (m, 4H), 7.60 (d, 1H), 7.73 (s, 1H).

EXAMPLE 36 ethyl3-(1-{(2S)-2-[(S)-(3,5-dimethoxy-4-methylphenyl)(hydroxy)methyl]-5-phenylpentyl}-1H-pyrazol-4-yl)propanoate Using the compound produced in Example 34 instead of the compound produced in Example 18, procedures similar to Example 19 were carried out, and to a methanol (5 ml) solution of the resulting ethyl(2E)-3-(1-{(2S)-2-[(S)-(3,5-dimethoxy-4-methylphenyl)(hydroxy)methyl]-5-phenylpentyl}-1H-pyrazol-4-yl)acrylate (39 mg), 10% palladium-carbon (8 mg) was added. The mixture was stirred under hydrogen gas atmosphere at room temperature for 8 hours. The reaction mixture was filtered, and the filtrate was concentrated to give the title compound (39 mg) having the following physical properties.

TLC: Rf 0.50 (hexane:ethyl acetate=1:1);
$^1$HNMR: δ 7.35 (s, 1H), 7.29-7.12 (m, 3H), 7.10-7.04 (m, 2H), 7.00 (s, 1H), 6.53 (s, 2H), 4.77 (d, 1H), 4.40-4.29 (m, 2H), 4.14 (t, 2H), 4.02 (dd, 1H), 3.81 (s, 6H), 2.77 (t, 2H), 2.64-2.38 (m, 4H), 2.10 (m, 1H), 2.07 (s, 3H), 1.72-1.57 (m, 3H), 1.25 (t, 3H), 1.12 (m, 1H).

EXAMPLE 37

3-(1-{(2S)-2-[(S)-(3,5-dimethoxy-4-methylphenyl)(hydroxy)methyl]-5-phenylpentyl}-1H-pyrazol-4-yl)propanoic acid Using the compound produced in Example 36 instead of the compound produced in Example 4(1), procedures similar to Example 5(1) were carried out to give the title compound having the following physical properties.

TLC: Rf 0.35 (hexane:ethyl acetate=1:3);
$^1$HNMR: δ 1.23 (m, 2H), 1.62 (m, 2H), 2.07 (s, 3H), 2.17 (m, 1H), 2.55 (m, 4H), 2.75 (t, 2H), 3.79 (s, 6H), 4.03 (dd, 1H), 4.34 (m, 2H), 6.51 (s, 2H), 7.00 (s, 1H), 7.08 (m, 2H), 7.23 (m, 3H), 7.35 (s, 1H).

EXAMPLE 38

1-{(2S)-2-[(S)-{[tert-butyl(dimethyl)silyl]oxy}(3,5-dimethoxy-4-methylphenyl)methyl]-5-phenylpentyl}-1H-pyrazole-3-carbaldehyde Using 1H-pyrazole-3-carbaldehyde instead of ethyl1H-pyrrole-2-carboxylate, procedures similar to Example 24 were carried out to give the title compound having the following physical properties.

HPTLC: Rf 0.22 (hexane:ethyl acetate=9:1);
$^1$HNMR: δ 9.92 (s, 1H), 7.30-7.05 (m, 6H), 6.73 (d, 1H), 6.46 (s, 2H), 4.72 (d, 1H), 4.30 (dd, 1H), 4.11 (dd, 1H), 3.80 (s, 6H), 2.49 (m, 2H), 2.22 (m, 1H), 2.07 (s, 3H), 1.75-1.10 (m, 4H), 0.94 (s, 9H), 0.04 (s, 3H), −0.16 (s, 3H).

EXAMPLE 39

3-(1-{(2S)-2-[(S)-(3,5-dimethoxy-4-methylphenyl)(hydroxy)methyl]-5-phenylpentyl}-1H-pyrazol-3-yl)propanoic acid Using the compound produced in Example 38 instead of the compound produced in Example 33, procedures similar to Example 34→Example 36→Example 37 were carried out to give the title compound having the following physical properties.

TLC: Rf 0.32 (dichloromethane:methanol=9:1);
$^1$HNMR: δ 7.32-7.05 (m, 6H), 6.53 (s, 2H), 6.01 (d, 1H), 4.39 (d, 1H), 4.32 (dd, 1H), 4.03 (dd, 1H), 3.81 (s, 6H), 2.97 (t, 2H), 2.72 (t, 2H), 2.62-2.38 (m, 2H), 2.10 (m, 1H), 2.07 (s, 3H), 1.70-1.55 (m, 2H), 1.40-1.05 (m, 2H).

EXAMPLE 40

(1-{(2S)-2-[(S)-(3,5-dimethoxy-4-methylphenyl)(hydroxy)methyl]-5-phenylpentyl}-1H-pyrazol-3-yl)acetic acid Using the compound produced in Example 38 instead of ethyl1-{(2S)-2-[(S)-{[tert-butyl(dimethyl)silyl]oxy}(3,5-dimethoxy-4-methylphenyl)methyl]-5-phenylpentyl}-1H-pyrazole-4-carboxylate, procedures similar to Example 29 Example 30→Example 31→Example 32 were carried out to give the title compound having the following physical properties.

TLC: Rf 0.50 (chloroform:methanol=9:1);
$^1$HNMR: δ 1.23 (m, 2H), 1.64 (m, 2H), 2.07 (s, 3H), 2.15 (m, 1H), 2.50 (m, 2H), 3.72 (s, 2H), 3.79 (s, 6H), 4.09 (dd, 1H), 4.31 (dd, 1H), 4.43 (d, 1H), 6.13 (d, 1H), 6.51 (s, 2H), 7.08 (m, 2H), 7.20 (m, 4H).

EXAMPLE 41(1) TO EXAMPLE 41(2)

Using ethyl3-methyl-1H-pyrazole-5-carboxylate instead of ethyl1H-pyrrole-2-carboxylate, procedures similar to Example 24 were carried out to give each of the compounds having the following physical properties.

EXAMPLE 41(1)

ethyl1-{(2S)-2-[(S)-{[tert-butyl(dimethyl)silyl]oxy}(3,5-dimethoxy-4-methylphenyl)methyl]-5-phenylpentyl}-3-methyl-1H-pyrazole-5-carboxylate TLC: Rf 0.63 (hexane:ethyl acetate=2:1);
$^1$HNMR: δ 7.28-7.04 (m, 6H), 6.55 (s, 2H), 4.67 (d, 1H), 4.59 (dd, 1H), 4.41 (dd, 1H), 4.25 (q, 2H), 3.80 (s, 6H), 2.42 (m, 2H), 2.40 (m, 1H), 2.23 (s, 3H), 2.06 (s, 3H), 1.60-1.20 (m, 4H), 1.32 (t, 3H), 0.91 (s, 9H), 0.00 (s, 3H), −0.18 (s, 3H).

EXAMPLE 41(2)

ethyl1-{(2S)-2-[(S)-{[tert-butyl(dimethyl)silyl]oxy}(3,5-dimethoxy-4-methylphenyl)methyl]-5-phenylpentyl}-5-methyl-1H-pyrazole-3-carboxylate TLC: Rf 0.52 (hexane:ethyl acetate=2:1);
$^1$HNMR: δ 7.30-7.06 (m, 6H), 6.47 (s, 2H), 4.78 (d, 1H), 4.37 (q, 1H), 4.14 (m, 1H), 4.03 (dd, 1H), 3.80 (s, 6H), 2.48

(m, 2H), 2.08 (m, 1H), 2.06 (s, 3H), 2.02 (s, 3H), 1.72-1.20 (m, 4H), 1.37 (t, 3H), 0.95 (s, 9H), 0.04 (s, 3H), −0.15 (s, 3H).

EXAMPLE 42(1) TO EXAMPLE 42(2)

Using the compound produced in Example 41(1) or the compound produced in Example 41(2) instead of ethyl1-{(2S)-2-[(S)-{[tert-butyl(dimethyl)silyl]oxy}(3,5-dimethoxy-4-methylphenyl)methyl]-5-phenylpentyl}-1H-pyrazole-4-carboxylate, procedures similar to Example 29→Example 30→Example 31→Example 32 were carried out to give each of the following compounds.

EXAMPLE 42(1)

(1-{(2S)-2-[(S)-(3,5-dimethoxy-4-methylphenyl)(hydroxy)methyl]-5-phenylpentyl}-3-methyl-1H-pyrazol-5-yl)acetic acid TLC: Rf 0.19 (dichloromethane:methanol=9:1);
$^1$HNMR: 67.32-7.04 (m, 5H), 6.54 (s, 2H), 5.96 (s, 1H), 4.58 (d, 1H), 4.15-3.90 (m, 2H), 3.79 (s, 6H), 3.51 (d, 2H), 2.65-2.38 (m, 2H), 2.23 (s, 3H), 2.20 (m, 1H), 2.07 (s, 3H), 1.75-1.10 (m, 4H).

EXAMPLE 42(2)

(1-{(2S)-2-[(S)-(3,5-dimethoxy-4-methylphenyl)(hydroxy)methyl]-5-phenylpentyl}-5-methyl-1H-pyrazol-3-yl)acetic acid TLC: Rf 0.37 (dichloromethane:methanol=9:1);
$^1$HNMR: δ 7.32-7.04 (m, 5H), 6.52 (s, 2H), 5.90 (s, 1H), 4.64 (d, 1H), 4.03 (m, 2H), 3.80 (s, 6H), 3.67 (s, 2H), 2.62-2.40 (m, 2H), 2.20 (m, 1H), 2.15 (s, 3H), 2.07 (s, 3H), 1.72-1.16 (m, 4H).

EXAMPLE 43(1) TO EXAMPLE 43(2)

Using ethyl3-methyl-1H-pyrazole-4-carboxylate instead of ethyl1H-pyrrole-2-carboxylate, procedures similar to Example 24→Example 29 were carried out to give each of the compounds having the following physical properties.

EXAMPLE 43(1)

(1-{(2S)-2-[(S)-{[tert-butyl(dimethyl)silyl]oxy}(3,5-dimethoxy-4-methylphenyl)methyl]-5-phenylpentyl}-3-methyl-1H-pyrazol-4-yl)methanol HPTLC: Rf 0.41 (hexane:ethyl acetate=1:1);
$^1$HNMR: δ 7.30-7.02 (m, 6H), 6.44 (s, 2H), 4.71 (d, 1H), 4.44 (d, 2H), 4.15 (m, 1H), 3.86 (dd, 1H), 3.79 (s, 6H), 2.52 (m, 2H), 2.21 (s, 3H), 2.20 (m, 1H), 2.05 (s, 3H), 1.80-1.10 (m, 4H), 0.94 (s, 9H), 0.04 (s, 3H), −0.16 (s, 3H).

EXAMPLE 43(2)

(1-{(2S)-2-[(S)-{[tert-butyl(dimethyl)silyl]oxy}(3,5-dimethoxy-4-methylphenyl)methyl]-5-phenylpentyl}-5-methyl-1H-pyrazol-4-yl)methanol HPTLC: Rf 0.34 (hexane:ethyl acetate=1:1);
$^1$HNMR: δ 7.36 (s, 1H), 7.28-7.04 (m, 5H), 6.48 (s, 2H), 4.80 (d, 1H), 4.44 (s, 2H), 4.07 (m, 1H), 3.91 (dd, 1H), 3.79 (s, 6H), 2.52 (m, 2H), 2.18 (m, 1H), 2.06 (s, 3H), 2.01 (s, 3H), 1.78-1.10 (m, 4H), 0.97 (s, 9H), 0.05 (s, 3H), −0.14 (s, 3H).

EXAMPLE 44(1) TO EXAMPLE 44(2)

Using the compound produced in Example 43(1) or the compound produced in Example 43(2) instead of ethyl1-{(2S)-2-[(S)-{[tert-butyl(dimethyl)silyl]oxy}(3,5-dimethoxy-4-methylphenyl)methyl]-5-phenylpentyl}-1H-pyrazole-4-carboxylate, procedures similar to Example 29→Example 30→Example 31→Example 32 were carried out to obtain the following compound.

EXAMPLE 44(1)

(1-{(2S)-2-[(S)-(3,5-dimethoxy-4-methylphenyl)(hydroxy)methyl]-5-phenylpentyl}-3-methyl-1H-pyrazol-4-yl)acetic acid TLC: Rf 0.44 (dichloromethane:methanol=9:1);
$^1$HNMR: δ 7.29-7.05 (m, 6H), 6.54 (s, 2H), 4.39 (d, 1H), 4.27 (dd, 1H), 3.97 (dd, 1H), 3.81 (s, 6H), 3.43 (s, 2H), 2.62-2.38 (m, 2H), 2.21 (s, 3H), 2.10 (m, 1H), 2.07 (s, 3H), 1.70-1.52 (m, 2H), 1.38-1.05 (m, 2H).

EXAMPLE 44(2)

(1-{(2S)-2-[(S)-(3,5-dimethoxy-4-methylphenyl)(hydroxy)methyl]-5-phenylpentyl}-5-methyl-1H-pyrazol-4-yl)acetic acid TLC: Rf 0.44 (dichloromethane:methanol=9:1);
$^1$HNMR: δ 7.43 (s, 1H), 7.29-7.04 (m, 5H), 6.55 (s, 2H), 4.57 (d, 1H), 4.14 (dd, 1H), 4.02 (dd, 1H), 3.80 (s, 6H), 3.43 (s, 2H), 2.62-2.38 (m, 2H), 2.18 (m, 1H), 2.10 (s, 3H), 2.07 (s, 3H), 1.80-1.10 (m, 4H).

EXAMPLE 45

3-(1-{(2S)-2-[(S)-(3,5-dimethoxy-4-methylphenyl)(hydroxy)methyl]-5-phenylpentyl}-1H-pyrrol-3-yl)propanoic acid Using ethyl1-{(2S)-2-[(S)-{[tert-butyl(dimethyl)silyl]oxy}(3,5-dimethoxy-4-methylphenyl)methyl]-5-phenylpentyl}-1H-pyrrole-3-carboxylate (produced by carrying out procedures similar to Example 24 using the compound produced in Example 16 and ethyl1H-pyrrole-3-carboxylate) instead of ethyl1-{(2S)-2-[(S)-{[tert-butyl(dimethyl)silyl]oxy}(3,5-dimethoxy-4-methylphenyl)methyl]-5-phenylpentyl}-1H-pyrazole-4-carboxylate, procedures similar to Example 29→Example 33→Example 34→Example 36→Example 37 were carried out to give the title compound having the following physical properties.

TLC: Rf 0.21 (hexane:ethyl acetate=1:1),
$^1$HNMR: δ 1.19 (m, 2H), 1.53 (m, 2H), 1.98 (m, 1H), 2.08 (s, 3H), 2.43 (m, 2H), 2.56 (t, 2H), 2.76 (t, 2H), 3.80 (s, 6H), 3.94 (dd, 1H), 4.02 (dd, 1H), 4.40 (d, 1H), 5.95 (m, 1H), 6.40 (m, 1H), 6.46 (s, 2H), 6.51 (t, 1H), 7.14 (m, 5H).

EXAMPLE 46

(3S)-3-[(S)-{[tert-butyl(dimethyl)silyl]oxy}(3,5-dimethoxy-4-methylphenyl)methyl]-6-phenylhexanenitrile Using the compound produced in Example 17 instead of the compound produced in Example 30, procedures similar to Example 31 were carried out to give the title compound having the following physical properties.

TLC: Rf 0.50 (hexane:ethyl acetate=8:1);
$^1$HNMR: δ 7.30-7.09 (m, 5H), 6.41 (s, 2H), 4.55 (d, 1H), 3.80 (s, 6H), 2.63-2.52 (m, 3H), 2.37 (dd, 1H), 2.08 (s, 3H), 1.94-1.84 (m, 1H), 1.75-1.39 (m, 4H), 0.92 (s, 9H), 0.06 (s, 3H), −0.20 (s, 3H).

EXAMPLE 47

(3S)-3-[(S)-{[tert-butyl(dimethyl)silyl]oxy}(3,5-dimethoxy-4-methylphenyl)methyl]-6-phenylhexanal To a toluene (7 ml) solution of the compound (357 mg) produced in Example 46, a 1.01M diisobutyl aluminum hydride toluene solution (1.5 ml) was added under argon atmosphere at −78° C. The reaction mixture was stirred at −78° C. for 10 minutes and at 0° C. for 50 minutes. Under ice-cooling, 1N hydrochloric acid was added thereto, followed by stirring. Ethyl acetate was added to the reaction mixture, the mixture was washed with water and brine successively, dried over with anhydrous magnesium sulfate, and concentrated to give the title compound (370 mg) having the following physical properties.

TLC: Rf 0.49 (hexane:ethyl acetate=8:1).

EXAMPLE 48

(3S)-3-[(S)-{[tert-butyl(dimethyl)silyl]oxy}(3,5-dimethoxy-4-methylphenyl)methyl]-6-phenylhexanoic acid To a mixed solution of tert-butyl alcohol (8 ml) with water (2 ml) of the compound (370 mg) produced in Example 47, 2-methyl-2-butene (0.37 ml), sodium dihydrogen phosphate (138 mg) and sodium chlorite (260 mg) were added, and the mixture was stirred at room temperature for 70 minutes. To the reaction mixture, 1N hydrochloric acid was added, and the mixture was diluted with ethyl acetate. The organic layer was washed with water and brine successively, dried over anhydrous magnesium sulfate, and concentrated to give the title compound (320 mg) having the following physical properties.

TLC: Rf 0.13 (hexane:ethyl acetate=2:1).

EXAMPLE 49 methyl4-({(3S)-3-[(S)-{[tert-butyl(dimethyl)silyl]oxy}(3,5-dimethoxy-4-methylphenyl)methyl]-6-phenylhexanoyl}amino)-3-hydroxybutanoate To a dichloromethane (10 ml) solution of the compound (320 mg) produced in Example 48, methyl4-amino-3-hydroxybutanoate hydrochloride (218 mg), triethylamine (0.23 ml), 1-hydroxybenzotriazole (148 mg) and 1-ethyl-3-[3-(dimethylamino)propyl]carbodiimide hydrochloride (247 mg) were added. The mixture was stirred at room temperature overnight. The reaction mixture was diluted with dichloromethane, and washed with a saturated aqueous sodium hydrogen carbonate solution, 1N hydrochloric acid, water and brine successively, dried over anhydrous magnesium sulfate, and concentrated. The residue was purified with silica gel column chromatography (hexane:ethyl acetate=2:1) to give the title compound (330 mg) having the following physical properties.

TLC: Rf 0.36 (hexane:ethyl acetate=1:1);
$^1$HNMR: δ 7.31-7.12 (m, 5H), 6.43 (s, 2H), 5.86-5.77 (m, 1H), 4.70 (d, 1H), 4.07-3.96 (m, 1H), 3.79 (s, 6H), 3.70 (s, 3H), 3.63 (t, 1H), 3.47-3.35 (m, 1H), 3.17-3.04 (m, 1H), 2.62-2.53 (m, 2H), 2.47-2.41 (m, 2H), 2.35 (d, 1H), 2.11-2.02 (m, 4H), 1.75-1.22 (m, 4H), 0.92 (s, 9H), 0.02 (s, 3H), −0.16 (s, 3H).

EXAMPLE 50 methyl4-({(3S)-3-[(S)-{[tert-butyl(dimethyl)silyl]oxy}(3,5-dimethoxy-4-methylphenyl)methyl]-6-phenylhexanoyl}amino)-3-oxobutanoate To a dichloromethane (5 ml) solution of the compound produced in Example 49 (99 mg), 1,1,1-tris(acetoxy)-1,1-dihydro-1,2-benziodoxol-3(1H)-one (Dess-Martin reagent, 105 mg) was added, and the mixture was stirred at room temperature for 1.5 hours. The reaction mixture was diluted with dichloromethane, washed with a saturated aqueous sodium hydrogen carbonate solution, water and brine successively, dried over anhydrous magnesium sulfate, and concentrated. The residue was purified with silica gel column chromatography (hexane:ethyl acetate=2:1) to give the title compound (61 mg) having the following physical properties.

TLC: Rf 0.54 (hexane:ethyl acetate=1:1);
$^1$HNMR: δ 7.29-7.12 (m, 5H), 6.44 (s, 2H), 6.08 (t, 1H), 4.68 (d, 1H), 4.17-4.12 (m, 2H), 3.79 (s, 6H), 3.74 (s, 3H), 3.47 (s, 2H), 2.60-2.53 (m, 2H), 2.43-2.34 (m, 1H), 2.15-2.03 (m, 5H), 1.74-1.22 (m, 4H), 0.92 (s, 9H), 0.02 (s, 3H), −0.17 (s, 3H).

EXAMPLE 51 methyl(2-{(2S)-2-[(S)-{[tert-butyl(dimethyl)silyl]oxy}(3,5-dimethoxy-4-methylphenyl)methyl]-5-phenylpentyl}-1,3-thiazol-5-yl)acetate To a toluene (3 ml) solution of the compound (30 mg) produced in Example 50, 2,4-bis(4-methoxyphenyl)-1,3-dithia-2,4-diphosphetane-2,4-disulfide (Lawesson's reagent, 23 mg) was added. The mixture was refluxed for 30 minutes, and the reaction mixture was concentrated. The residue was purified with silica gel column chromatography (hexane:ethyl acetate=8:1) to give the title compound (28 mg) having the following physical properties.

TLC: Rf 0.28 (hexane:ethyl acetate=4:1);
$^1$HNMR: δ 7.40 (t, 1H), 7.28-7.08 (m, 5H), 6.48 (s, 2H), 4.71 (d, 1H), 3.80 (s, 6H), 3.78 (d, 2H), 3.73 (s, 3H), 3.09 (dd, 1H), 2.88 (dd, 1H), 2.54-2.46 (m, 2H), 2.16-2.03 (m, 4H), 1.71-1.23 (m, 4H), 0.92 (s, 9H), 0.02 (s, 3H), −0.18 (s, 3H).

EXAMPLE 52

(2-{(2S)-2-[(S)-(3,5-dimethoxy-4-methylphenyl)(hydroxy)methyl]-5-phenylpentyl}-1,3-thiazol-5-yl)acetic acid Using the compound produced in Example 51, procedures similar to Example 20→Example 19 were carried out to give the title compound having the following physical properties.

TLC: Rf 0.33 (dichloromethane:methanol=9:1);
$^1$HNMR (CD$_3$OD): δ 7.42 (s, 1H), 7.19-6.99 (m, 5H), 6.58 (s, 2H), 4.59 (d, 1H), 3.81 (s, 2H), 3.79 (s, 6H), 3.14 (dd, 1H), 2.94 (dd, 1H), 2.44 (t, 2H), 2.26-2.13 (m, 1H), 2.01 (s, 3H), 1.61-1.15 (m, 4H).

EXAMPLE 53 methyl(2-{(2S)-2-[(S)-{[tert-butyl(dimethyl)silyl]oxy}(3,5-dimethoxy-4-methylphenyl)methyl]-5-phenylpentyl}-1,3-oxazol-5-yl)acetate To a dichloroethane (5 ml) solution of triphenylphosphine (137 mg) and iodine (132 mg), a dichloromethane (5 ml)

solution of the compound (104 mg) produced in Example 50 and triethylamine (0.15 ml) was added, and the mixture was stirred at 35° C. for 3.5 hours. The reaction mixture was concentrated. The residue was purified with silica gel column chromatography (hexane:ethyl acetate=6:1) to give the title compound (29 mg) having the following physical properties.

TLC: Rf 0.25 (hexane:ethyl acetate=4:1);

$^1$HNMR: δ 7.28-7.09 (m, 5H), 6.80 (s, 1H), 6.46 (s, 2H), 4.68 (d, 1H), 3.79 (s, 6H), 3.71 (s, 3H), 3.62 (s, 2H), 2.86 (dd, 1H), 2.72 (dd, 1H), 2.56-2.47 (m, 2H), 2.20-2.10 (m, 1H), 2.05 (s, 3H), 1.71-1.19 (m, 4H), 0.91 (s, 9H), 0.01 (s, 3H), −0.19 (s, 3H).

EXAMPLE 54

(2-{(2S)-2-[(S)-(3,5-dimethoxy-4-methylphenyl)(hydroxy)methyl]-5-phenylpentyl}-1,3-oxazol-5-yl)acetic acid Using the compound produced in Example 53 instead of the compound in produced in Example 19, procedures similar to Example 20→Example 19 were carried out to give the title compound having the following physical properties.

TLC: Rf 0.32 (dichloromethane:methanol=9:1);

$^1$HNMR (CD$_3$OD): δ 7.21-7.01 (m, 5H), 6.82 (s, 1H), 6.55 (s, 2H), 4.57 (d, 1H), 3.78 (s, 6H), 3.67 (s, 2H), 2.92 (dd, 1H), 2.74 (dd, 1H), 2.47 (t, 2H), 2.30-2.16 (m, 1H), 2.00 (s, 3H), 1.59-1.12 (m, 4H).

EXAMPLE 55

(2R)-2-[(S)-{[tert-butyl(dimethyl)silyl]oxy}(3,5-dimethoxy-4-methylphenyl)methyl]-5-phenylpentanoic acid To a mixed solution of tetrahydrofuran (75 ml) with water (25 ml), the compound (4.97 g) produced in Example 13, a 30% hydrogen peroxide solution (10 ml) suspension of lithium hydroxide (2.43 g) was added at 0° C., and the mixture was stirred at 0° C. for 3 hours. To the reaction mixture, an aqueous solution (100 ml) of sodium sulfite (14.5 g) and 5N hydrochloric acid (14 ml) were added. The reaction solution was concentrated and extracted with ethyl acetate. The extract was washed with water and brine successively, dried over anhydrous magnesium sulfate, and concentrated. The residue was purified with silica gel column chromatography (hexane:ethyl acetate=1:1) to obtain a compound (2.05 g). Procedures similar to Example 14 were carried out by using the thus obtained compound instead of the compound produced in Example 13, and hydrolysis was carried out by using 1N hydrochloric acid to give the title compound having the following physical properties.

TLC: Rf 0.26 (hexane:ethyl acetate=4:1);

$^1$HNMR: δ −0.21 (s, 3H), 0.01 (s, 3H), 0.83 (s, 9H), 1.21 (m, 1H), 1.59 (m, 3H), 2.08 (s, 3H), 2.50 (m, 2H), 2.71 (m, 1H), 3.80 (s, 6H), 4.65 (d, 1H), 6.46 (s, 2H), 7.04 (m, 2H), 7.17 (m, 3H).

EXAMPLE 56 methyl4-({(2R)-2-[(S)-{[tert-butyl(dimethyl)silyl]oxy}(3,5-dimethoxy-4-methylphenyl)methyl]-5-phenylpentanoyl}amino)benzoate To a dichloromethane (1 ml) solution of the compound (100 mg) produced in Example 55, oxalyl chloride (37 >1) and a catalytic amount of dimethylformamide were added at 0° C., followed by stirring at room temperature for 30 minutes. The reaction mixture was concentrated to obtain acid chloride. To a dichloromethane (1 ml) solution of methyl4-aminobenzoate (384 mg), triethylamine (44 >1) and a dichloromethane (1 ml) solution of the obtained acid chloride were added at 0° C. The reaction mixture was stirred at room temperature for 20 minutes. Water was added to the reaction mixture, followed by extraction with ethyl acetate. The extract was washed with 1N hydrochloric acid and brine, dried over anhydrous sodium sulfate, and concentrated. The residue was purified with silica gel column chromatography (hexane:ethyl acetate=8:1→4:1) to give the title compound (42 mg) having the following physical properties.

TLC: Rf 0.54 (hexane:ethyl acetate=2:1);

$^1$HNMR: δ 8.20 (s, 1H), 8.00 (d, 2H), 7.60 (d, 2H), 7.28-7.08 (m, 5H), 6.42 (s, 2H), 4.73 (d, 1H), 3.90 (s, 3H), 3.69 (s, 6H), 2.58 (t, 2H), 2.49 (m, 1H), 2.04 (s, 3H), 1.90-1.30 (m, 4H), 0.86 (s, 9H), −0.01 (s, 3H), -0.15 (s, 3H).

EXAMPLE 57

4-({(2R)-2-[(S)-(3,5-dimethoxy-4-methylphenyl)(hydroxy)methyl]-5-phenylpentanoyl}amino)benzoic acid Using the compound produced in Example 56 instead of the compound produced in Example 19, procedures similar to Example 20→Example 19 were carried out to give the title compound having the following physical properties.

TLC: Rf 0.30 (dichloromethane:methanol=9:1);

$^1$HNMR: δ 8.04 (d, 2H), 7.67 (s, 1H), 7.58 (d, 2H), 7.30-7.08 (m, 5H), 6.49 (s, 2H), 4.83 (d, 1H), 3.75 (s, 6H), 2.65-2.50 (m, 3H), 2.06 (s, 3H), 2.02-1.20 (m, 4H).

EXAMPLE 57(1) TO EXAMPLE 57(3)

Using a corresponding aniline derivative instead of methyl4-aminobenzoate, procedures similar to Example 56 Example 57 were carried out to give each of the compound of the present invention.

EXAMPLE 57(1)

3-({(2R)-2-[(S)-(3,5-dimethoxy-4-methylphenyl)(hydroxy)methyl]-5-phenylpentanoyl}amino)benzoic acid TLC: Rf 0.17 (dichloromethane:methanol=9:1);

$^1$HNMR: δ 7.98 (m, 1H), 7.92 (d, 1H), 7.81 (d, 1H), 7.70 (s, 1H), 7.40 (dd, 1H), 7.29-7.09 (m, 5H), 6.50 (s, 2H), 4.83 (d, 1H), 3.75 (s, 6H), 2.65-2.52 (m, 3H), 2.06 (s, 3H), 2.05-1.40 (m, 4H).

EXAMPLE 57(2)

[4-({(2R)-2-[(S)-(3,5-dimethoxy-4-methylphenyl)(hydroxy)methyl]-5-phenylpentanoyl}amino)phenyl]acetic acid TLC: Rf 0.10 (dichloromethane:methanol=9:1);

$^1$HNMR: δ 7.43-7.36 (m, 2H), 7.30-7.10 (m, 8H), 6.49 (s, 2H), 4.80 (d, 1H), 3.75 (s, 6H), 3.62 (s, 2H), 2.65-2.42 (m, 3H), 2.06 (s, 3H), 2.00-1.30 (m, 4H).

EXAMPLE 57(3)

[3-({(2R)-2-[(S)-(3,5-dimethoxy-4-methylphenyl)(hydroxy)methyl]-5-phenylpentanoyl}amino)phenyl]acetic acid TLC: Rf 0.14 (dichloromethane:methanol=9:1);
$^1$HNMR: δ 7.47 (s, 1H), 7.40-7.35 (m, 2H), 7.29-7.08 (m, 6H), 7.02 (d, 1H), 6.47 (s, 2H), 4.79 (d, 1H), 3.74 (s, 6H), 3.61 (s, 2H), 2.58 (m, 2H), 2.50 (m, 1H), 2.06 (s, 3H), 2.00-1.42 (m, 4H).

EXAMPLE 58

(2S,3S)-3-{[tert-butyl(dimethyl)silyl]oxy}-2-(2,3-dihydro-1H-inden-2-ylmethyl)-3-(3,5-dimethoxy-4-methylphenyl)propyl methanesulfonate Using 3-(2,3-dihydro-1H-inden-2-yl)propanoyl chloride instead of 5-phenylpentanoyl chloride, procedures similar to Example 12→Example 13 Example 14→Example 15→Example 16 were carried out to give the title compound having the following physical properties.
TLC: Rf 0.86 (toluene:ethyl acetate=4:1);
$^1$HNMR: δ 7.18-7.02 (m, 4H), 6.46 (s, 2H), 4.65 (d, 1H), 4.41 (dd, 1H), 4.31 (dd, 1H), 3.80 (s, 6H), 3.10-2.92 (m, 2H), 2.95 (s, 3H), 2.60-2.38 (m, 4H), 2.06 (s, 3H), 1.58-1.22 (m, 2H), 0.90 (s, 9H), 0.06 (s, 3H), −0.19 (s, 3H).

EXAMPLE 59

{1-[(2S,3S)-2-(2,3-dihydro-1H-inden-2-ylmethyl)-3-(3,5-dimethoxy-4-methylphenyl)-3-hydroxypropyl]-1H-pyrrol-3-yl}acetic acid

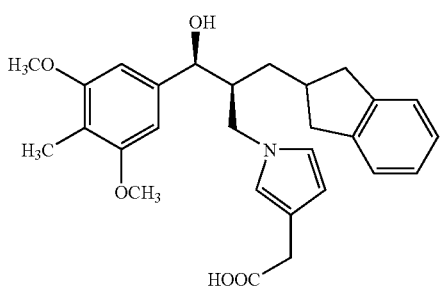

Using the compound produced in Example 58 instead of the compound produced in Example 16, procedures similar to Example 26→Example 27→Example 19 were carried out to give the title compound having the following physical properties.
Property: amorphous;
TLC: Rf 0.39 (dichloromethane:methanol=9:1);
$^1$HNMR: δ 7.15-7.02 (m, 4H), 6.64 (m, 2H), 6.49 (s, 2H), 6.08 (dd, 1H), 4.46 (d, 1H), 4.15 (dd, 1H), 4.01 (dd, 1H), 3.81 (s, 6H), 3.53 (s, 2H), 3.02-2.88 (m, 2H), 2.50-2.28 (m, 3H), 2.15 (m, 1H), 2.06(s, 3H), 1.42-1.35(m, 2H).

EXAMPLE 59(1) TO EXAMPLE 59(5)

Using a corresponding acid chloride compound instead of 3-(2,3-dihydro-1H-inden-2-yl)propanoyl chloride, or a corresponding aldehyde compound instead of 3,5-dimethoxy-4-methylbenzaldehyde, procedures similar to Example 58→Example 59 were carried out to give each of the following compounds.

EXAMPLE 59(1)

(1-{(2S)-2-[(S)-(3,5-dimethoxy-4-methylphenyl)(hydroxy)methyl]-5-thien-3-ylpentyl}-1H-pyrrol-3-yl)acetic acid Property: amorphous;
TLC: Rf 0.52 (dichloromethane:methanol=9:1);
$^1$HNMR: δ 7.20 (dd, 1H), 6.83-6.77 (m, 2H), 6.58-6.54 (m, 2H), 6.47 (s, 2H), 6.08-6.05 (m, 1H), 4.43 (d, 1H), 4.09-3.93 (m, 2H), 3.81 (s, 6H), 3.52 (s, 2H), 2.58-2.40 (m, 2H), 2.08 (s, 3H), 2.08-1.95 (m, 1H), 1.62-1.48 (m, 2H), 1.31-1.11 (m, 2H).

EXAMPLE 59(2)

{1-[(2S,3S)-2-(1,3-benzodioxol-2-ylmethyl)-3-(3,5-dimethoxy-4-methylphenyl)-3-hydroxypropyl]-1H-pyrrol-3-yl}acetic acid Property: amorphous;
TLC: Rf 0.51 (dichloromethane:methanol=9:1);
$^1$HNMR: δ 1.77-2.00 (m, 2H), 2.06 (s, 3H), 2.42-2.60 (m, 1H), 3.51 (s, 2H), 3.80 (s, 6H), 3.98-4.09 (m, 1H), 4.09-4.22 (m, 1H), 4.62 (d, 1H), 5.81-5.89 (m, 1H), 6.08 (t, 1H), 6.48 (s, 2H), 6.65 (d, 2H), 6.70-6.84 (m, 4H).

EXAMPLE 59(3)

{1-[(2S,3S)-2-(2,3-dihydro-1H-inden-2-ylmethyl)-3-hydroxy-3-(3,4,5-trimethoxyphenyl)propyl]-1H-pyrrol-3-yl}acetic acid Property: amorphous;
TLC: Rf 0.17 (hexane:ethyl acetate=1:2);
$^1$HNMR: δ 7.20-7.05 (m, 4H), 6.65-6.60 (m, 2H), 6.52 (s, 2H), 6.08 (m, 1H), 4.44 (d, 1H), 4.20-3.90 (m, 2H), 3.84 (s, 6H), 3.83 (s, 3H), 3.52 (s, 2H), 3.00-2.90 (m, 2H), 2.50-2.30 (m, 3H), 2.20-2.10 (m, 1H), 1.40-1.30 (m, 2H).

EXAMPLE 59(4)

{1-[(2S,3S)-3-(4-acetyl-3,5-dimethoxyphenyl)-2-(2,3-dihydro-1H-inden-2-ylmethyl)-3-hydroxypropyl]-1H-pyrrol-3-yl}acetic acid Property: amorphous;
TLC: Rf 0.20 (dichloromethane:methanol=9:1);
$^1$HNMR: δ 7.20-7.08 (m, 4H), 6.61 (dd, 1H), 6.56 (m, 1H), 6.49 (s, 2H), 6.06 (m, 1H), 4.54 (d, 1H), 4.10 (dd, 1H), 3.97 (dd, 1H), 3.79 (s, 6H), 3.50 (s, 2H), 3.06-2.94 (m, 2H), 2.60-2.38 (m, 3H), 2.46 (s, 3H), 2.18 (m, 1H), 1.42 (m, 2H).

EXAMPLE 59(5)

{1-[(2S,3S)-2-(2,3-dihydro-1H-inden-2-ylmethyl)-3-(4-ethyl-3,5-dimethoxyphenyl)-3-hydroxypropyl]-1H-pyrrol-3-yl}acetic acid Property: amorphous;
TLC: Rf 0.56 (hexane:ethyl acetate=1:2);
$^1$HNMR: δ 7.20-7.05 (m, 4H), 6.65-6.60 (m, 2H), 6.49 (s, 2H), 6.08 (t, 1H), 4.46 (d, 1H), 4.20-3.90 (m, 2H), 3.80 (s, 6H), 3.52 (s, 2H), 3.00-2.90 (m, 2H), 2.62 (q, 2H), 2.50-2.30 (m, 3H), 2.20-2.10 (m, 1H), 1.40-1.30 (m, 2H), 1.05 (t, 3H).

EXAMPLE 60

1-[(2S,3S)-3-{[tert-butyl(dimethyl)silyl]oxy}-2-(2,3-dihydro-1H-inden-2-ylmethyl)-3-(3,5-dimethoxy-4-methylphenyl)propyl]-1H-pyrrole-3-carbaldehyde Using 1H-pyrrole-3-carbaldehyde instead of 1H-pyrrol-3-ylacetonitrile and the compound produced in Example 58 instead of the compound produced in Example 16, procedures similar to Example 26 were carried out to give the title compound having the following physical properties.

TLC: Rf 0.53 (hexane:ethyl acetate=2:1);
$^1$HNMR: δ 9.67 (s, 1H), 7.20-7.05 (m, 5H), 6.55 (m, 1H), 6.51 (m, 1H), 6.46 (s, 2H), 4.76 (d, 1H), 4.07 (dd, 1H), 3.82 (s, 6H), 3.76, (m, 1H), 3.02-2.88 (m, 2H), 2.58-2.35 (m, 2H), 2.29 (dd, 1H), 2.08 (s, 3H), 2.04 (m ,1H), 1.75 (m, 1H), 1.24 (m, 1H), 0.98 (s, 9H), 0.08 (s, 3H), −0.15 (s, 3H).

EXAMPLE 61

(2E)-3-{1-[(2S,3S)-2-(2,3-dihydro-1H-inden-2-ylmethyl)-3-(3,5-dimethoxy-4-methylphenyl)-3-hydroxypropyl]-1H-pyrrol-3-yl}acrylic acid Using the compound produced in Example 60 instead of the compound produced in Example 33, procedures similar to Example 34→Example 35 were carried out to give the title compound having the following physical properties.

Property: amorphous;
TLC: Rf 0.42 (dichloromethane:methanol=9:1);
$^1$HNMR: δ 7.69 (d, 1H), 7.18-7.08 (m, 4H), 6.96 (m, 1H), 6.69 (dd, 1H), 6.49 (s, 2H), 6.40 (m, 1H), 6.07 (d, 1H), 4.43 (d, 1H), 4.23 (dd, 1H), 4.04 (dd, 1H), 3.81 (s, 6H), 3.04-2.90 (m, 2H), 2.55-2.28 (m, 3H), 2.16 (m, 1H), 2.06 (s, 3H), 1.37 (m, 2H).

EXAMPLE 62

3-{1-[(2S,3S)-2-(2,3-dihydro-1H-inden-2-ylmethyl)-3-(3,5-dimethoxy-4-methylphenyl)-3-hydroxypropyl]-1H-pyrrol-3-yl}propanoic acid Using the compound produced in Example 61 instead of the compound produced in Example 34, procedures similar to Example 36 were carried out to give the title compound having the following physical properties.

Property: amorphous;
TLC: Rf 0.58 (dichloromethane:methanol=9:1);
$^1$HNMR: δ 7.18-7.05 (m, 4H), 6.58 (dd, 1H), 6.51 (m, 1H), 6.49 (s, 2H), 5.97 (dd, 1H), 4.44 (d, 1H), 4.12 (dd, 1H), 3.98 (dd, 1H), 3.81 (s, 6H), 3.01-2.85 (m, 2H), 2.78 (t, 2H), 2.57 (t, 2H), 2.44-2.28 (m, 3H), 2.15 (m, 1H), 2.06 (s, 3H), 1.41-1.32 (m, 2H).

EXAMPLE 62(1)

3-{1-[(2S,3S)-2-(2,3-dihydro-1H-inden-2-ylmethyl)-3-hydroxy-3-(3,4,5-trimethoxyphenyl)propyl]-1H-pyrrol-3-yl}propanoic acid Using 3,4,5-trimethoxybenzaldehyde instead of 3,5-dimethoxy-4-methylbenzaldehyde, procedures similar to Example 58→Example 60→Example 61→Example 62 were carried out to give the title compound having the following physical properties.

Property: amorphous;
TLC: Rf 0.44 (dichloromethane:methanol=9:1);
$^1$HNMR: δ 7.16-7.08 (m, 4H), 6.59-6.55 (m, 1H), 6.54-6.50 (m, 3H), 5.98-5.95 (m, 1H), 4.40 (d, 1H), 4.17-4.08 (m, 1H), 4.00-3.92 (m, 1H), 3.85 (s, 6H), 3.82 (s, 3H), 3.00-2.89 (m, 2H), 2.81-2.74 (m, 2H), 2.60-2.53 (m, 2H), 2.46-2.30 (m, 3H), 2.12-2.03 (m, 1H), 1.40-1.32 (m, 2H).

EXAMPLE 63(1) TO EXAMPLE 63(10)

Using (4S)-4-benzyl-1,3-oxazolidin-2-one or (4R)-4-benzyl-1,3-oxazolidin-2-one, using a corresponding acid chloride compound instead of 5-phenylpentanoyl chloride, using 3,5-dimethoxy-4-methylbenzaldehyde or a corresponding aldehyde compound instead of it, or using 1H-pyrrol-3-ylacetonitrile or a corresponding cyano compound instead of ethyl1H-pyrrole-2-carboxylate, procedures similar to methods shown in Example 12→Example 13→Example 14→Example 15→Example 16→Example 26 Example 27→Example 19 were carried out to give each of the following title compounds.

EXAMPLE 63(1)

{1-[(2S,3S)-2-(1-benzofuran-2-ylmethyl)-3-(3,5-dimethoxy-4-methylphenyl)-3-hydroxypropyl]-1H-pyrrol-3-yl}acetic acid

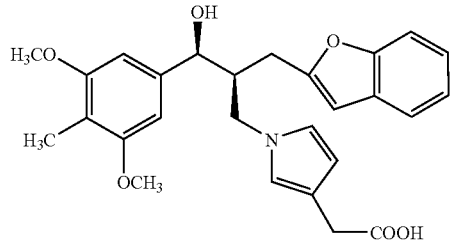

TLC: Rf 0.25 (hexane:ethyl acetate=1:2);
$^1$HNMR: δ 7.50-7.46 (m, 1H), 7.43-7.39 (m, 1H), 7.29-7.15 (m, 2H), 6.69-6.66 (m, 2H), 6.52 (s, 2H), 6.38 (s, 1H), 6.10 (t, 1H), 4.54 (d, 1H), 4.18 (dd, 1H), 4.00 (dd, 1H), 3.81 (s, 6H), 3.53 (s, 2H), 2.73-2.50 (m, 3H), 2.06 (s, 3H).

EXAMPLE 63(2)

{1-[(2R,3R)-2-(2,3-dihydro-1H-inden-2-ylmethyl)-3-(3,5-dimethoxy-4-methylphenyl)-3-hydroxypropyl]-1H-pyrrol-3-yl}acetic acid TLC: Rf 0.44 (dichloromethane:methanol=9:1);
$^1$HNMR: δ 1.37 (t, 2H), 2.06 (s, 3H), 2.08-2.20 (m, 1H), 2.28-2.54 (m, 3H), 2.87-3.05 (m, 2H), 3.52 (s, 2H), 3.81 (s, 6H), 4.00 (dd, 1H), 4.15 (dd, 1H), 4.45 (d, 1H), 6.06-6.09 (m, 1H), 6.48 (s, 2H), 6.59-6.68 (m, 2H), 7.00-7.17 (m, 4H).

EXAMPLE 63(3)

{1-[(2S,3S)-2-(2,3-dihydro-1H-inden-2-ylmethyl)-3-(3,5-dimethoxy-4-methylphenyl)-3-hydroxypropyl]-1H-pyrazol-4-yl}acetic acid TLC: Rf 0.40 (chloroform:methanol=9:1);
$^1$HNMR: δ 1.31-1.57 (m, 2H), 2.06 (s, 3H), 2.16-2.62 (m, 4H), 2.85-3.13 (m, 2H), 3.54 (s, 2H), 3.77 (s, 6H), 4.10 (dd, 1H), 4.40 (dd, 1H), 4.49 (d, 1H), 6.55 (s, 2H), 7.00-7.19 (m, 4H), 7.37 (s, 1H), 7.48 (s, 1H).

EXAMPLE 63(4)

{1-[(2S,3S)-2-(2,3-dihydro-1H-inden-2-ylmethyl)-3-(3,5-dimethoxyphenyl)-3-hydroxypropyl]-1H-pyrrol-3-yl}acetic acid TLC: Rf 0.23 (hexane:ethyl acetate=1:1);
$^1$HNMR: δ 7.20-7.05 (m, 4H), 6.60-6.55 (m, 2H), 6.50-6.45 (m, 2H), 6.40-6.35 (m, 1H), 6.05 (m, 1H), 4.50 (d, 1H), 4.10-3.90 (m, 2H), 3.78 (s, 6H), 3.50 (s, 2H), 3.00-2.90 (m, 2H), 2.50-2.30 (m, 3H), 2.20-2.10 (m, 1H), 1.50-1.30 (m, 2H).

EXAMPLE 63(5)

{1-[(2S,3S)-2-(2,3-dihydro-1H-inden-2-ylmethyl)-3-(4-ethoxy-3,5-dimethoxyphenyl)-3-hydroxypropyl]-1H-pyrrol-3-yl}acetic acid TLC: Rf 0.20 (hexane:ethyl acetate=1:2);
$^1$HNMR: δ 7.20-7.05 (m, 4H), 6.65-6.60 (m, 2H), 6.52 (s, 2H), 6.07 (t, 1H), 4.44 (d, 1H), 4.20-3.90 (m, 2H), 4.02 (q, 2H), 3.83 (s, 6H), 3.52 (s, 2H), 3.00-2.90 (m, 2H), 2.50-2.30 (m, 3H), 2.20-2.10 (m, 1H), 1.40-1.30 (m, 2H), 1.33 (t, 3H).

EXAMPLE 63(6)

(1-{(2S,3S)-2-(2,3-dihydro-1H-inden-2-ylmethyl)-3-hydroxy-3-[4-(1-hydroxy-1-methylethyl)-3,5-dimethoxyphenyl]propyl}-1H-pyrrol-3-yl)acetic acid TLC: Rf 0.37 (dichloromethane:methanol=9:1);
$^1$HNMR: δ 7.20-7.05 (m, 4H), 6.57 (dd, 1H), 6.54 (s, 2H), 6.37 (m, 1H), 6.02 (dd, 1H), 4.58 (d, 1H), 4.01 (m, 2H), 3.83 (s, 6H), 3.45 (s, 2H), 3.10-2.90 (m, 2H), 2.60-2.35 (m, 3H), 2.15 (m, 1H), 1.65 (s, 3H), 1.63 (s, 3H), 1.51 (m, 2H).

EXAMPLE 63(7)

{1-[(2S,3S)-3-(4-chloro-3,5-dimethoxyphenyl)-2-(2,3-dihydro-1H-inden-2-ylmethyl)-3-hydroxypropyl]-1H-pyrrol-3-yl}acetic acid TLC: Rf 0.45 (dichloromethane:methanol=9:1);
$^1$HNMR: δ 7.14-7.08 (m, 4H), 6.66-6.59 (m, 2H), 6.52 (s, 2H), 6.09-6.05 (m, 1H), 4.44 (d, 1H), 4.16 (dd, 1H), 3.95 (dd, 1H), 3.88 (s, 6H), 3.53 (s, 2H), 3.01-2.88 (m, 2H), 2.50-2.29 (m, 3H), 2.17-2.08 (m, 1H), 1.41-1.33 (m, 2H).

EXAMPLE 63(8)

(1-{(2S,3S)-3-(3,5-dimethoxy-4-methylphenyl)-3-hydroxy-2-[(2-methyl-2,3-dihydro-1H-inden-2-yl)methyl]propyl}-1H-pyrrol-3-yl)acetic acid TLC: Rf 0.57 (hexane:ethyl acetate=1:2);
$^1$HNMR: δ 7.10-6.95 (m, 4H), 6.55 (m, 2H), 6.40 (s, 2H), 6.05 (t, 1H), 4.49 (d, 1H), 4.13 (dd, 1H), 3.82 (dd, 1H), 3.75 (s, 6H), 3.51 (s, 2H), 2.61 (s, 2H), 2.60-2.40 (m, 2H), 2.15-2.05 (m, 1H), 2.06 (s, 3H), 1.55 (dd, 1H), 1.40 (dd, 1H), 1.03 (s, 3H).

EXAMPLE 63(9)

(1-{(2S,3S)-3-(3,5-dimethoxy-4-methylphenyl)-3-hydroxy-2-[(4-methoxy-2,3-dihydro-1H-inden-2-yl)methyl]propyl}-1H-pyrrol-3-yl)acetic acid TLC: Rf 0.35 (dichloromethane:methanol=9:1);
$^1$HNMR: δ 7.08 (m, 1H), 6.74 (m, 1H), 6.68-6.59 (m, 3H), 6.49 (s, 2H), 6.07 (m, 1H), 4.50-4.40 (m, 1H), 4.17 (m, 1H), 4.00 (m, 1H), 3.81 (s, 6H), 3.80 (s, 3/2H), 3.79 (s, 3/2H), 3.53 (s, 2/2H), 3.52 (s, 2/2H), 3.10-2.90 (m, 2H), 2.55-2.00 (m, 4H), 2.06 (s, 3/2H), 2.05 (s, 3/2H), 1.40 (m, 2H).

EXAMPLE 63(10)

4-(carboxymethyl)-1-[(2S,3S)-2-(2,3-dihydro-1H-inden-2-ylmethyl)-3-(3,5-dimethoxy-4-methylphenyl)-3-hydroxypropyl]-1H-pyrrole-3-carboxylic acid TLC: Rf 0.24 (dichloromethane:methanol=9:1);
$^1$HNMR (CD$_3$OD): δ 7.29 (d, 1H), 7.08-6.96 (m, 4H), 6.62 (s, 1H), 6.57 (s, 2H), 4.46 (d, 1H), 4.11-3.98 (m, 2H), 3.79 (s, 6H), 3.61 (s, 2H), 3.00-2.81 (m, 2H), 2.37-2.10 (m, 4H), 1.99 (s, 3H), 1.51-1.25 (m, 2H).

EXAMPLE 64(1) TO EXAMPLE 64(3)

Using the compound produced in Example 60 or a corresponding an aldehyde compound instead of the compound produced in Example 33, procedures similar to Example 34→Example 19 Example 20 were carried out to give each of the title compounds having the following physical properties.

EXAMPLE 64(1)

(2E)-3-{1-[(2S,3S)-2-(2,3-dihydro-1H-inden-2-ylmethyl)-3-(4-ethyl-3,5-dimethoxyphenyl)-3-hydroxypropyl]-1H-pyrrol-3-yl}acrylic acid TLC: Rf 0.50 (hexane:ethyl acetate=1:2);
$^1$HNMR: δ 7.69 (d, 1H), 7.15-7.05 (m, 4H), 6.96 (m, 1H), 6.68 (m, 1H), 6.48 (s, 2H), 6.40 (m, 1H), 6.06 (d, 1H), 4.42 (d, 1H), 4.30-4.00 (m, 2H), 3.81 (s, 6H), 3.00-2.90 (m, 2H), 2.62 (q, 2H), 2.50-2.30 (m, 3H), 2.20-2.10 (m, 1H), 1.40-1.30 (m, 2H), 1.05 (t, 3H).

EXAMPLE 64(2)

(2E)-3-{1-[(2S,3S)-2-(2,3-dihydro-1H-inden-2-ylmethyl)-3-hydroxy-3-(3,4,5-trimethoxyphenyl)propyl]-1H-pyrrol-3-yl}acrylic acid TLC: Rf 0.47 (dichloromethane: methanol=5:1);
$^1$HNMR: δ 1.29-1.40 (m, 2H), 2.06-2.17 (m, 1H), 2.31-2.46 (m, 3H), 2.90-3.03 (m, 2H), 3.83 (s, 3H), 3.85 (s, 6 H), 4.03 (dd, 1H), 4.15-4.27 (m, 1H), 4.40 (d, 1H), 6.06 (d, 1H), 6.37-6.42 (m, 1H), 6.52 (s, 2H), 6.63-6.69 (m, 1H), 6.93-6.97 (m, 1H), 7.04-7.15 (m, 4 H), 7.68 (d, 1H).

EXAMPLE 64(3)

(2E)-3-{1-[(2S,3S)-2-(2,3-dihydro-1H-inden-2-ylmethyl)-3-(3,5-dimethoxy-4-methylphenyl)-3-hydroxypropyl]-1H-pyrrol-3-yl}-2-methylacrylic acid Property: amorphous;
TLC: Rf 0.16 (n-hexane:ethyl acetate=1:1);

¹HNMR: δ 7.71 (s, 1H), 7.10 (m, 4H), 6.99 (s, 1H), 6.73 (m, 1H), 6.49 (s, 2H), 6.43 (s, 1H), 4.43 (d, 1H), 4.25 (dd, 1H), 4.08 (dd, 1H), 3.82 (s, 6H), 3.00-2.90 (m, 2H), 2.60-2.30 (m, 4H), 2.11 (s, 3H), 2.06 (s, 3H), 1.38 (t, 2H).

EXAMPLE 65(1) TO EXAMPLE 65(8)

Using corresponding acid chloride instead of phenylpentanoyl chloride, using 3,5-dimethoxy-4-methylbenzaldehyde or corresponding aldehyde instead of it, or using 1H-pyrrole-3-carbaldehyde or a corresponding aldehyde compound instead of 1H-pyrrol-3-ylacetonitrile, procedures similar to Example 12 Example 13→Example 14→Example 15→Example 16→Example 24→Example 29→Example 33→Example 34→Example 19→Example 36→Example 20 were carried out, and deprotection reaction of a protecting group was carried out, if necessary, to obtain each of the title compounds having the following physical properties.

EXAMPLE 65(1)

3-{1-[(2S,3S)-2-(2,3-dihydro-1H-inden-2-ylmethyl)-3-(3,5-dimethoxy-4-methylphenyl)-3-hydroxypropyl]-1H-pyrazol-4-yl}propanoic acid

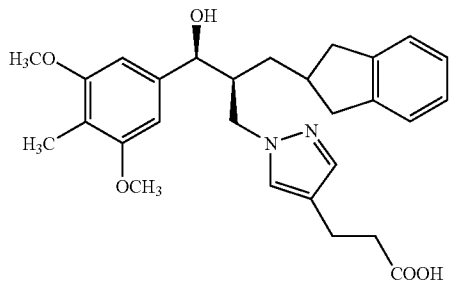

TLC: Rf 0.45 (chloroform:methanol=9:1);
¹HNMR: δ 1.29-1.52 (m, 2H), 2.05 (s, 3H), 2.20-2.51 (m, 4H), 2.58 (t, 2H), 2.78 (t, 2H), 2.88-3.12 (m, 2H), 3.81 (s, 6H), 4.10 (dd, 1H), 4.37 (dd, 1H), 4.46 (d, 1H), 6.55 (s, 2H), 7.01-7.18 (m, 4H), 7.20 (s, 1H), 7.39 (s, 1H).

EXAMPLE 65(2)

3-{1-[(2S,3S)-3-(4-chloro-3,5-dimethoxyphenyl)-2-(2,3-dihydro-1H-inden-2-ylmethyl)-3-hydroxypropyl]-1H-pyrrol-3-yl}propanoic acid TLC: Rf 0.55 (dichloromethane:methanol=9:1);
¹HNMR: δ 7.18-7.08 (m, 4H), 6.60-6.53 (m, 3H), 6.52-6.46 (m, 1H), 5.98-5.96 (m, 1H), 4.45 (d, 1H), 4.12 (dd, 1H), 3.95 (dd, 1H), 3.89 (s, 6H), 3.03-2.89 (m, 2H), 2.81-2.72 (m, 2H), 2.60-2.53 (m, 2H), 2.50-2.28 (m, 3H), 2.13-2.06 (m, 1H), 1.44-1.30 (m, 2H).

EXAMPLE 65(3)

3-{1-[(2S,3S)-2-(2,3-dihydro-1H-inden-2-ylmethyl)-3-(4-ethyl-3,5-dimethoxyphenyl)-3-hydroxypropyl]-1H-pyrrol-3-yl}propanoic acid TLC: Rf 0.52 (hexane:ethyl acetate=1:2);
¹HNMR: δ 7.15-7.05 (m, 4H), 6.58 (m, 1H), 6.51 (m, 1H), 6.49 (s, 2H), 5.97 (d, 1H), 4.43 (d, 1H), 4.20-3.95 (m, 2H), 3.80 (s, 6H), 3.00-2.90 (m, 2H), 2.78 (q, 2H), 2.70-2.50 (m, 4H), 2.50-2.30 (m, 3H), 2.20-2.10 (m, 1H), 1.40-1.30 (m, 2H), 1.05 (t, 3H).

EXAMPLE 65(4)

3-{1-[(2S,3S)-2-(1,3-benzodioxol-2-ylmethyl)-3-(3,5-dimethoxy-4-methylphenyl)-3-hydroxypropyl]-1H-pyrrol-3-yl}propanoic acid TLC: Rf 0.42 (dichloromethane:methanol=19:1);
¹HNMR: δ 1.76-1.98 (m, 2H), 2.06 (s, 3H), 2.42-2.52 (m, 1H), 2.52-2.59 (m, 2H), 2.76 (t, 2H), 3.80 (s, 6H), 3.97-4.05 (m, 1H), 4.06-4.15 (m, 1H), 4.60 (d, 1H), 5.80 (t, 1H), 5.96-5.99 (m, 1H), 6.48 (s, 2H), 6.51 (t, 1H), 6.60 (t, 1H), 6.71-6.82 (m, 4H).

EXAMPLE 65(5)

3-(1-{(2S,3S)-2-(2,3-dihydro-1H-inden-2-ylmethyl)-3-hydroxy-3-[4-(1-hydroxy-1-methylethyl)-3,5-dimethoxyphenyl]propyl}-1H-pyrrol-3-yl)propanoic acid TLC: Rf 0.29 (dichloromethane:methanol=9:1);
¹HNMR: δ 7.20-7.03 (m, 4H), 6.56 (s, 2H), 6.53 (m, 1H), 6.25 (m, 1H), 5.93 (m, 1H), 4.57 (d, 1H), 3.97 (m, 2H), 3.84 (s, 6H), 3.10-2.90 (m, 2H), 2.75 (m, 2H), 2.62-2.30 (m, 5H), 2.10 (m, 1H), 1.65 (s, 3H), 1.63 (s, 3H), 1.60-1.40 (m, 2H).

EXAMPLE 65(6)

3-(1-{(2S,3S)-3-(3,5-dimethoxy-4-methylphenyl)-2-[(4-fluoro-2,3-dihydro-1H-inden-2-yl)methyl]-3-hydroxypropyl}-1H-pyrrol-3-yl)propanoic acid TLC: Rf 0.47 (dichloromethane:methanol=9:1);
¹HNMR: δ 7.05 (m, 1H), 6.88 (m, 1H), 6.77 (m, 1H), 6.58 (dd, 1H), 6.51 (m, 1H), 6.49 (s, 2H), 5.98 (dd, 1H), 4.44 (m, 1H), 4.11 (m, 1H), 4.00 (m, 1H), 3.81 (s, 6H), 3.12-2.90 (m, 2H), 2.78 (t, 2H), 2.57 (t, 2H), 2.50-2.25 (m, 3H), 2.15 (m, 1H), 2.06 (s, 3H), 1.45-1.30 (m, 2H).

EXAMPLE 65(7)

3-(1-{(2S,3S)-3-(3,5-dimethoxy-4-methylphenyl)-2-[(5-fluoro-2,3-dihydro-1H-inden-2-yl)methyl]-3-hydroxypropyl}-1H-pyrrol-3-yl)propanoic acid TLC: Rf 0.37 (dichloromethane:methanol=9:1);
¹HNMR: δ 7.01 (m, 1H), 6.85-6.72 (m, 2H), 6.58 (dd, 1H), 6.50 (m, 1H), 6.48 (s, 2H), 5.98 (m, 1H), 4.43 (d, 1H), 4.11 (m, 1H), 3.99 (dd, 1H), 3.81 (s, 6H), 2.98-2.82 (m, 2H), 2.78 (t, 2H), 2.57 (t, 2H), 2.48-2.20 (m, 3H), 2.10 (m, 1H), 2.06 (s, 3H), 1.40-1.32 (m, 2H).

EXAMPLE 65(8)

3-(1-{(2S)-4-cyclopentyl-2-[(S)-(3,5-dimethoxy-4-methylphenyl)(hydroxy)methyl]butyl}-1H-pyrrol-3-yl)propanoic acid TLC: Rf 0.37 (hexane:ethyl acetate=1:1);
¹HNMR: δ 0.85-1.33 (m, 6H), 1.35-1.75 (m, 7H), 1.90-2.05 (m, 1H), 2.07 (s, 3H), 2.54-2.63 (m, 2H), 2.78 (t, 2H), 3.81 (s, 6H), 3.91-4.00 (m, 1H), 4.01-4.11 (m, 1H), 4.40 (d, 1H), 5.96-6.00 (m, 1H), 6.44-6.53 (m, 3H), 6.57 (t, 1H).

EXAMPLE 66(1) TO EXAMPLE 66(2)

Using the compound produced in Example 58 or (2S,3S)-3-{[tert-butyl(dimethyl)silyl]oxy}-2-(1,3-benzodioxol-2-ylmethyl)-3-(4-ethyl-3,5-dimethoxyphenyl)propyl methanesulfonate instead of the compound produced in Example 16, or using methyl1H-pyrrole-3-carboxylate or ethyl4-methyl-1H-pyrrole-3-carboxylate instead of ethyl1H-pyrrole-2-carboxylate, procedures similar to Example 24→Example 19→Example 20 were carried out to give each of the following title compounds.

EXAMPLE 66(1)

1-[(2S,3S)-2-(1,3-benzodioxol-2-ylmethyl)-3-(4-ethyl-3,5-dimethoxyphenyl)-3-hydroxypropyl]-1H-pyrazole-3-carboxylic acid TLC: Rf 0.39 (dichloromethane:methanol=9:1);
$^1$HNMR: δ 7.45 (t, 1H), 6.83-6.73 (m, 4H), 6.70-6.66 (m, 1H), 6.64-6.59 (m, 1H), 6.47 (s, 2H), 5.96 (t, 1H), 4.58 (d, 1H), 4.28 (dd, 1H), 4.12 (dd, 1H), 3.80 (s, 6H), 2.63 (q, 2H), 2.59-2.48 (m, 1H), 2.00-1.77 (m, 2H), 1.06 (t, 3H).

EXAMPLE 66(2)

1-[(2S,3S)-2-(2,3-dihydro-1H-inden-2-ylmethyl)-3-(3,5-dimethoxy-4-methylphenyl)-3-hydroxypropyl]-4-methyl-1H-pyrrole-3-carboxylic acid TLC: Rf 0.37 (hexane:ethyl acetate=1:1);
$^1$HNMR: δ 7.36 (d, 1H), 7.20-7.10 (m, 4H), 6.49 (s, 2H), 6.43 (s, 1H), 4.45 (s, 1H), 4.16 (dd, 1H), 3.98 (dd, 1H), 3.82 (s, 6H), 3.10-2.90 (m, 2H), 2.50-2.30 (m, 3H), 2.27 (s, 3H), 2.20-2.10 (m, 1H), 2.07 (s, 3H), 1.45-1.35 (m, 2H).

EXAMPLE 67(1) TO EXAMPLE 67(6)

Using the compound produced in Example 58 instead of the compound produced in Example 16, or a corresponding compound instead of ethyl pyrrole-2-carboxylate, procedures similar to Example 24→Example 19→Example 20 were carried out to give each of the following title compounds.

EXAMPLE 67(1)

4-{1-[(2S,3S)-2-(2,3-dihydro-1H-inden-2-ylmethyl)-3-(3,5-dimethoxy-4-methylphenyl)-3-hydroxypropyl]-1H-pyrrol-3-yl}butanoic acid TLC: Rf 0.39 (dichloromethane:methanol=9:1);
$^1$HNMR: δ 7.18-7.00 (m, 4H), 6.59 (dd, 1H), 6.49 (s, 2H), 6.48 (m, 1H), 5.96 (dd, 1H), 4.11 (m, 1H), 4.46 (d, 1H), 3.98 (dd, 1H), 3.81 (s, 6H), 3.02-2.90 (m, 2H), 2.60-2.35 (m, 3H), 2.51 (t, 2H), 2.36 (t, 2H), 2.15 (m, 1H), 2.06 (s, 3H), 1.95-1.82(m, 2H), 1.37 (m, 2H).

EXAMPLE 67(2)

3-{1-[(2S,3S)-2-(2,3-dihydro-1H-inden-2-ylmethyl)-3-(3,5-dimethoxy-4-methylphenyl)-3-hydroxypropyl]-1H-pyrrol-3-yl}-2-methylpropanoic acid TLC: Rf 0.56 (hexane:ethyl acetate=1:1);
$^1$HNMR: δ 7.20-7.05 (m, 4H), 6.60-6.40 (m, 4H), 5.95(m, 1H), 4.45-4.40 (m, 1H), 4.10-3.90 (m, 2H), 3.81 (s, 6H), 3.00-2.10 (m, 9H), 2.06 (s, 3H), 1.40-1.30 (m, 2H), 1.20-1.10 (m, 3H).

EXAMPLE 67(3)

3-{1-[(2S,3S)-2-(2,3-dihydro-1H-inden-2-ylmethyl)-3-(3,5-dimethoxy-4-methylphenyl)-3-hydroxypropyl]-1H-pyrrol-3-yl}-2-(hydroxymethyl)propanoic acid TLC: Rf 0.68 (ethyl acetate);
$^1$HNMR (CDCl$_3$+CD$_3$OD): δ 7.16-7.05 (m, 4H), 6.59-6.54 (m, 2H), 6.51 (s, 2H), 5.98-5.95 (m, 1H), 4.42-4.36 (m, 1H), 4.17-4.07 (m, 1H), 4.00-3.92 (m, 1H), 3.82 (s, 6H), 3.74-3.69 (m, 2H), 3.02-2.65 (m, 5H), 2.48-2.30 (m, 3H), 2.18-2.03 (m, 4H), 1.40-1.31 (m, 2H).

EXAMPLE 67(4)

2-{1-[(2S,3S)-2-(2,3-dihydro-1H-inden-2-ylmethyl)-3-(3,5-dimethoxy-4-methylphenyl)-3-hydroxypropyl]-1H-pyrrol-3-yl}-2-methylpropanoic acid TLC: Rf 0.41 (hexane:ethyl acetate=1:1);
$^1$HNMR: δ 7.16-7.06 (m, 4H), 6.64-6.56 (m, 2H), 6.49 (s, 2H), 6.12 (dd, 1H), 4.48 (d, 1H), 4.08-4.02 (m, 2H), 3.81 (s, 6H), 3.02-2.82 (m, 2H), 2.42-2.28 (m, 3H), 2.15 (m, 1H), 2.06 (s, 3H), 1.52 (s, 6H), 1.40 (m, 2H).

EXAMPLE 67(5)

3-{1-[(2S,3S)-2-(2,3-dihydro-1H-inden-2-ylmethyl)-3-(3,5-dimethoxy-4-methylphenyl)-3-hydroxypropyl]-1H-pyrrol-3-yl}-2,2-dimethylpropanoic acid TLC: Rf 0.55 (hexane:ethyl acetate=1:1);
$^1$HNMR: δ 7.20-7.00 (m, 4H), 6.55 (m, 1H), 6.49 (s, 2H), 6.47 (m, 1H), 5.94 (m, 1H), 4.41 (d, 1H), 4.10 (dd, 1H), 3.99 (dd, 1H), 3.81 (s, 6H), 3.00-2.90 (m, 2H), 2.74-2.60 (m, 2H), 2.40-2.30 (m, 3H), 2.20-2.00 (m, 1H), 2.06 (s, 3H), 1.40-1.30 (m, 2H), 1.17 (s, 3H), 1.15 (s, 3H).

EXAMPLE 67(6)

2-{1-[(2S,3S)-2-(2,3-dihydro-1H-inden-2-ylmethyl)-3-(4-ethyl-3,5-dimethoxyphenyl)-3-hydroxypropyl]-1H-pyrrol-3-yl}-2-methylpropanoic acid TLC: Rf 0.32 (hexane:ethyl acetate=1:1);
$^1$HNMR: δ 7.16-7.05 (m, 4H), 6.62-6.56 (m, 2H), 6.49 (s, 2H), 6.11 (dd, 1H), 4.47 (d, 1H), 4.08-3.96 (m, 2H), 3.80 (s, 6H), 3.00-2.94 (m, 2H), 2.62 (q, 2H), 2.45-2.30 (m, 3H), 2.15 (m, 1H), 1.51 (s, 6H), 1.38 (m, 2H), 1.05 (t, 3H).

EXAMPLE 68

2-{1-[(2S,3S)-2(2,3-dihydro-1H-inden-2-ylmethyl)-3(3,5-dimethoxy-4-methylphenyl)-3-hydroxypropyl]-1H-pyrrol-3-yl}-N-(methylsulfonyl)acetamide

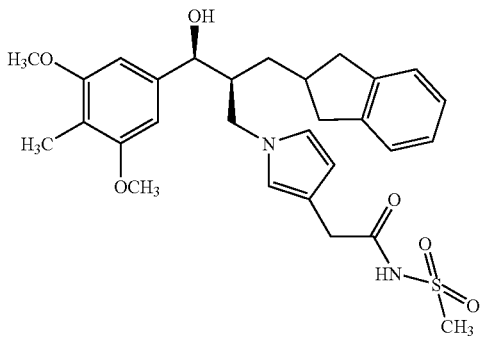

To a dichloromethane (10 ml) solution of {1-[(2S,3S)-3-{[tert-butyl(dimethyl)silyl]oxy}-2-(2,3-dihydro-1H-inden-2-ylmethyl)-3-(3,5-dimethoxy-4-methylphenyl)propyl]-1H-pyrrol-3-yl}acetic acid (obtained by carrying out procedures similar to Example 26→Example 27 using the compound produced in Example 58 instead of the compound produced in Example 16) (305 mg) and methanesulfonamide (76 mg), 1-ethyl-3-(3-dimethylaminopropyl)carbodiimide hydrochloride (153 mg) and 4-dimethylaminopyridine (65 mg) were added at room temperature under stirring, and the mixture was stirred at room temperature overnight. To the reaction mixture, 1N hydrochloric acid was added, followed by extraction with ethyl acetate. The organic layer was washed with brine, dried over anhydrous magnesium sulfate, and concentrated. The residue was purified with silica gel column chromatography (hexane:ethyl acetate=20:1→1:1) to obtain 2-{1-[(2S,3S)-3-{[tert-butyl(dimethyl)silyl]oxy}-2-(2,3-dihydro-1H-inden-2-ylmethyl)-3-(3,5-dimethoxy-4-methylphenyl)propyl]-1H-pyrrol-3-yl}-N-(methylsulfonyl)acetamide (265 mg). Successively, using this compound instead of the compound produced in Example 18, procedures similar to the method shown in Example 19 were carried out to give the title compound (220 mg) having the following physical properties.

TLC: Rf 0.60 (dichloromethane:methanol=9:1);
$^1$HNMR: δ 8.08-8.00 (m, 1H), 7.15-7.08 (m, 4H), 6.73-6.65 (m, 2H), 6.50 (s, 2H), 6.04-5.98 (m, 1H), 4.42 (dd, 1H), 4.21 (dd, 1H), 4.03 (dd, 1H), 3.82 (s, 6H), 3.56 (s, 2H), 3.24 (s, 3H), 3.03-2.90 (m, 2H), 2.51-2.31 (m, 3H), 2.18-2.07 (m, 1H), 2.06 (s, 3H), 1.94 (d, 1H), 1.42-1.33 (m, 2H).

EXAMPLE 68(1) TO EXAMPLE 68(63)

Using {1-[(2S,3S)-3-{[tert-butyl(dimethyl)silyl]oxy}-2-(2,3-dihydro-1H-inden-2-ylmethyl)-3-(3,5-dimethoxy-4-methylphenyl)propyl]-1H-pyrrol-3-yl}acetic acid or a corresponding carboxylic acid, or methanesulfonamide or a corresponding amine compound, procedures similar to Example 68 were carried out to give each of the following title compounds.

EXAMPLE 68(1)

methyl1-[(2S,3S)-2-(2,3-dihydro-1H-inden-2-ylmethyl)-3-(3,5-dimethoxy-4-methylphenyl)-3-hydroxypropyl]-4-{2-[(methylsulfonyl)amino]-2-oxoethyl}-1H-pyrrole-3-carboxylate TLC: Rf 0.52 (hexane:ethyl acetate=1:2);
$^1$HNMR: δ 10.4 (s, 1H, NH), 7.28 (d, 1H), 7.15-7.08 (m, 4H), 6.68 (d, 1H), 6.48 (s, 2H), 4.42 (d, 1), 4.18 (dd, 1H), 4.02 (dd, 1H), 3.85 (s, 3H), 3.82 (s, 6H), 3.65 (s, 2H), 3.17 (s, 3H), 3.05-2.88 (m, 2H), 2.49-2.30 (m, 3H), 2.20-2.08 (m, 1H), 2.06 (s, 3H), 2.00-1.98 (m, 1H, OH), 1.48-1.32 (m, 2H).

EXAMPLE 68(2)

N-(3-{1-[(2S,3S)-2-(2,3-dihydro-1H-inden-2-ylmethyl)-3-(3,5-dimethoxy-4-methylphenyl)-3-hydroxypropyl]-1H-pyrrol-3-yl}propanoyl)ethanesulfonamide TLC: Rf 0.40 (dichloromethane:methanol=9:1);
$^1$HNMR: δ 7.77-7.71 (m, 1H), 7.15-7.06 (m, 4H), 6.68-6.65 (m, 1H), 6.65-6.53 (m, 1H), 6.52 (s, 2H), 6.02-5.97 (m, 1H), 4.42 (d, 1H), 4.19 (dd, 1H), 3.99 (dd, 1H), 3.81 (s, 6H), 3.38 (q, 2H), 3.02-2.84 (m, 2H), 2.83-2.75 (m, 2H), 2.60-2.52 (m, 2H), 2.47-2.29 (m, 3H), 2.20-2.06 (m, 1H), 2.06 (s, 3H), 1.41-1.31 (m, 2H), 1.29 (t, 3H).

EXAMPLE 68(3)

N-(3-{1-[(2S,3S)-2-(2,3-dihydro-1H-inden-2-ylmethyl)-3-(3,5-dimethoxy-4-methylphenyl)-3-hydroxypropyl]-1H-pyrrol-3-yl}propanoyl)methanesulfonamide TLC: Rf 0.43 (dichloromethane:methanol=9:1);
$^1$HNMR: δ 7.88-7.84 (m, 1H), 7.15-7.06 (m, 4H), 6.68-6.65 (m, 1H), 6.63-6.53 (m, 1H), 6.52 (s, 2H), 6.01-5.97 (m, 1H), 4.42 (d, 1H), 4.19 (dd, 1H), 3.99 (dd, 1H), 3.82 (s, 6H), 3.20 (s, 3H), 3.00-2.90 (m, 2H), 2.87-2.78 (m, 2H), 2.60-2.52 (m, 2H), 2.47-2.29 (m, 3H), 2.20-2.06 (m, 1H), 2.06 (s, 3H), 1.41-1.33 (m, 2H).

EXAMPLE 68(4)

N-(3-{1-[(2S,3S)-2-(2,3-dihydro-1H-inden-2-ylmethyl)-3-(3,5-dimethoxy-4-methylphenyl)-3-hydroxypropyl]-1H-pyrrol-3-yl}propanoyl)-1,1,1-trifluoromethanesulfonamide TLC: Rf 0.08 (hexane:ethyl acetate=1:2);
$^1$HNMR: δ 8.39-8.05 (m, 1H), 7.16-7.06 (m, 4H), 6.71-6.67 (m, 1H), 6.58-6.51 (m, 1H), 6.51 (s, 2H), 6.02-5.97 (m, 1H), 5.60-5.26 (m, 1H), 4.42 (d, 1H), 4.19 (dd, 1H), 4.02 (dd, 1H), 3.81 (s, 6H), 3.02-2.84 (m, 2H), 2.83-2.78 (m, 2H), 2.72-2.65 (m, 2H), 2.47-2.29 (m, 3H), 2.20-2.06 (m, 1H), 2.06 (s, 3H), 1.41-1.31 (m, 2H).

EXAMPLE 68(5)

N-(3-{1-[(2S,3S)-2-(2,3-dihydro-1H-inden-2-ylmethyl)-3-(3,5-dimethoxy-4-methylphenyl)-3-hydroxypropyl]-1H-pyrrol-3-yl}propanoyl)benzenesulfonamide TLC: Rf 0.50 (dichloromethane:methanol=9:1);
$^1$HNMR: δ 8.39-8.05 (m, 1H), 8.00-7.94 (m, 2H), 7.64-7.57 (m, 1H), 7.50-7.44 (m, 2H), 7.16-7.06 (m, 4H), 6.63-6.59 (m, 1H), 6.53 (s, 2H), 6.52-6.46 (m, 1H), 5.90-5.86 (m, 1H), 4.43 (d, 1H), 4.18 (dd, 1H), 3.97 (dd, 1H), 3.79 (s, 6H), 3.02-2.89 (m, 2H), 2.75-2.68 (m, 2H), 2.49-2.29 (m, 5H), 2.22-2.06 (m, 1H), 2.06 (s, 3H), 1.41-1.31 (m, 2H).

EXAMPLE 68(6)

N-(2-{1-[(2S,3S)-2-(2,3-dihydro-1H-inden-2-ylmethyl)-3-(3,5-dimethoxy-4-methylphenyl)-3-hydroxypropyl]-1H-pyrrol-3-yl}acetyl)ethanesulfonamide TLC: Rf 0.33 (hexane:ethyl acetate=1:1);
$^1$HNMR: δ 1.27-1.40 (m, 5H), 2.06 (s, 3H), 2.09-2.19 (m, 1H), 2.34-2.48 (m, 3H), 2.91-3.03 (m, 2H), 3.42 (q, 2H), 3.55 (s, 2H), 3.82 (s, 6H), 4.03 (dd, 1H), 4.22 (dd, 1H), 4.41 (d, 1H), 5.99-6.05 (m, 1H), 6.50 (s, 2H), 6.64-6.72 (m, 2H), 7.06-7.15 (m, 4H), 7.94 (s, 1H).

EXAMPLE 68(7)

N-({1-[(2S,3S)-2-(2,3-dihydro-1H-inden-2-ylmethyl)-3-(3,5-dimethoxy-4-methylphenyl)-3-hydroxypropyl]-1H-pyrrol-3-yl}acetyl)-1,1,1-trifluoromethanesulfonamide TLC: Rf 0.05 (hexane:ethyl acetate=1':2);
$^1$HNMR: δ 1.29-1.40 (m, 2H), 2.06 (s, 3H), 2.09-2.20 (m, 1H), 2.31-2.46 (m, 3H), 2.89-3.03 (m, 2H), 3.64 (s, 2H), 3.81 (s, 6H), 4.04 (dd, 1H), 4.24 (dd, 1H), 4.38 (d, 1H), 6.01-6.06 (m, 1H), 6.48 (s, 2H), 6.66-6.75 (m, 2H), 7.05-7.15 (m, 4H).

EXAMPLE 68(8)

N-(2-{1-[(2S,3S)-2-(2,3-dihydro-1H-inden-2-ylmethyl)-3-(3,5-dimethoxy-4-methylphenyl)-3-hydroxypropyl]-1H-pyrrol-3-yl}acetyl)benzenesulfonamide TLC: Rf 0.40 (hexane:ethyl acetate=1:1);
$^1$HNMR: δ 1.32-1.43 (m, 2H), 2.07 (s, 3H), 2.09-2.19 (m, 1H), 2.32-2.49 (m, 3H), 2.90-3.04 (m, 2H), 3.43 (s, 2H), 3.82 (s, 6H), 4.02 (dd, 1H), 4.22 (dd, 1H), 4.42 (d, 1H), 5.91-5.97 (m, 1H), 6.51 (s, 2H), 6.59-6.64 (m, 1H), 6.64-6.71 (m, 1H), 7.05-7.15 (m, 4H), 7.45-7.55 (m, 2H), 7.57-7.65 (m, 1H), 7.95-8.02 (m, 2H), 8.23-8.31 (m, 1H).

EXAMPLE 68(9)

N-(3-{1-[(2S,3S)-2-(2,3-dihydro-1H-inden-2-ylmethyl)-3-(3,5-dimethoxy-4-methylphenyl)-3-hydroxypropyl]-1H-pyrrol-3-yl}propanoyl)-4-fluorobenzenesulfonamide TLC: Rf 0.47 (hexane:ethyl acetate=1:1);
$^1$HNMR: δ 8.01 (dd, 2H), 7.97 (s, 1H), 7.20-7.06 (m, 6H), 6.63 (m, 1H), 6.54 (s, 2H), 6.51 (m, 1H), 5.89 (m, 1H), 4.45 (d, 1H), 4.18 (dd, 1H), 4.00 (dd, 1H), 3.81 (s, 6H), 3.03-2.90 (m, 2H), 2.74 (t, 2H), 2.52-2.30 (m, 5H), 2.15 (m, 1H), 2.06 (s, 3H), 1.40 (m, 2H).

EXAMPLE 68(10)

4-t-butyl-N-(3-{1-[(2S,3S)-2-(2,3-dihydro-1H-inden-2-ylmethyl)-3-(3,5-dimethoxy-4-methylphenyl)-3-hydroxypropyl]-1H-pyrrol-3-yl}propanoyl)benzenesulfonamide TLC: Rf 0.55 (hexane:ethyl acetate=1:1);
$^1$HNMR: δ 7.96 (s, 1H), 7.90 (d, 2H), 7.50 (d, 2H), 7.18-7.04 (m, 4H), 6.64 (m, 1H), 6.55 (m, 3H), 5.90 (m, 1H), 4.44 (d, 1H), 4.21 (dd, 1H), 4.00 (dd, 1H), 3.80 (s, 6H), 3.02-2.90 (m, 2H), 2.74 (t, 2H), 2.52-2.30 (m, 5H), 2.15 (m, 1H), 2.06 (s, 3H), 1.38 (m, 2H), 1.33 (s, 9H).

EXAMPLE 68(11)

N-(3-{1-[(2S,3S)-2-(2,3-dihydro-1H-inden-2-ylmethyl)-3-(3,5-dimethoxy-4-methylphenyl)-3-hydroxypropyl]-1H-pyrrol-3-yl}propanoyl)-4-methoxybenzenesulfonamide TLC: Rf 0.38 (hexane:ethyl acetate=1:1);
$^1$HNMR: δ 7.93 (s, 1H), 7.92 (d, 2H), 7.19-7.05 (m, 4H), 6.95 (d, 2H), 6.64 (m, 1H), 6.55 (s, 2H), 6.53 (m, 1H), 5.91 (m, 1H), 4.44 (d, 1H), 4.20 (dd, 1H), 4.00 (dd, 1H), 3.86 (s, 3H), 3.81(s, 6H), 3.02-2.90 (m, 2H), 2.73 (t, 2H), 2.52-2.30 (m, 5H), 2.15 (m, 1H), 2.06 (s, 3H), 1.39 (m, 2H).

EXAMPLE 68(12)

N-(3-{1-[(2S,3S)-2-(2,3-dihydro-1H-inden-2-ylmethyl)-3-(3,5-dimethoxy-4-methylphenyl)-3-hydroxypropyl]-1H-pyrrol-3-yl}propanoyl)-4-methylbenzenesulfonamide TLC: Rf 0.52 (hexane:ethyl acetate=1:1);
$^1$HNMR: δ 1.31-1.45 (m, 2H), 2.06 (s, 3H), 2.08-2.17 (m, 1H), 2.34-2.48 (m, 8H), 2.68-2.77 (m, 2H), 2.90-3.02 (m, 2H), 3.80 (s, 6H), 3.99 (dd, 1H), 4.20 (dd, 1H), 4.44 (dd, 1H), 5.88-5.93 (m, 1H), 6.50-6.58 (m, 3H), 6.61-6.67 (m, 1H), 7.06-7.16 (m, 4H), 7.27-7.33 (m, 2H), 7.83-7.91 (m, 2H), 7.98 (s, 1H).

EXAMPLE 68(13)

N-(3-{1-[(2S,3S)-2-(2,3-dihydro-1H-inden-2-ylmethyl)-3-(3,5-dimethoxy-4-methylphenyl)-3-hydroxypropyl]-1H-pyrrol-3-yl}propanoyl)-4-(trifluoromethyl)benzenesulfonamide TLC: Rf 0.43 (hexane:ethyl acetate=1:1);
$^1$HNMR: δ 1.33-1.44 (m, 2H), 2.06 (s, 3H), 2.08-2.19 (m, 1H), 2.34-2.50 (m, 5H), 2.69-2.78 (m, 2H), 2.89-3.03 (m, 2H), 3.81 (s, 6H), 4.00 (dd, 1H), 4.18 (dd, 1H), 4.45 (d, 1H), 5.86-5.91 (m, 1H), 6.50-6.57 (m, 3H), 6.61-6.67 (m, 1H), 7.07-7.15 (m, 4H), 7.74-7.80 (m, 2H), 8.02-8.16 (m, 3H).

EXAMPLE 68(14)

4-chloro-N-(3-{1-[(2S,3S)-2-(2,3-dihydro-1H-inden-2-ylmethyl)-3-(3,5-dimethoxy-4-methylphenyl)-3-hydroxypropyl]-1H-pyrrol-3-yl}propanoyl)benzenesulfonamide TLC: Rf 0.52 (hexane:ethyl acetate=1:1);
$^1$HNMR: δ 1.30-1.44 (m, 2H), 2.06 (s, 3H), 2.09-2.18 (m, 1H), 2.34-2.49 (m, 5H), 2.69-2.78 (m, 2H), 2.90-3.02 (m, 2H), 3.81 (s, 6H), 3.99 (dd, 1H), 4.18 (dd, 1H), 4.44 (d, 1H), 5.87-5.91 (m, 1H), 6.47-6.52 (m, 1H), 6.54 (s, 2H), 6.61-6.67 (m, 1H), 7.07-7.16 (m, 4H), 7.43-7.50 (m, 2H), 7.88-7.95 (m, 2H), 8.05 (s, 1H).

EXAMPLE 68(15)

N-(3-{1-[(2S,3S)-2-(2,3-dihydro-1H-inden-2-ylmethyl)-3-(3,5-dimethoxy-4-methylphenyl)-3-hydroxypropyl]-1H-pyrrol-3-yl}-2-methylpropanoyl)methanesulfonamide TLC: Rf 0.16 (hexane:ethyl acetate=2:1);
$^1$HNMR: δ 7.80-7.60 (m, 1H), 7.20-7.05 (m, 4H), 6.70-6.50 (m, 4H), 6.00-5.95 (m, 1H), 4.41 (d, 1H), 4.25-4.15 (m, 1H), 4.00-3.95 (m, 1H), 3.81 (s, 6H), 3.16 (m, 3H), 3.00-2.90 (m, 2H), 2.75-2.65 (m, 2H), 2.60-2.30 (m, 4H), 2.20-2.10 (m, 1H), 2.06 (s, 3H), 1.40-1.20 (m, 5H).

EXAMPLE 68(16)

N-(3-{1-[(2S,3S)-2-(2,3-dihydro-1H-inden-2-ylmethyl)-3-(3,5-dimethoxy-4-methylphenyl)-3-hydroxypropyl]-1H-pyrrol-3-yl}-2-methylpropanoyl)benzenesulfonamide TLC: Rf 0.33 (hexane:ethyl acetate=2:1);
$^1$HNMR: δ 8.00-7.95 (m, 2H), 7.90-7.75 (m, 1H), 7.60-7.40 (m, 3H), 7.20-7.05 (m, 4H), 6.65 (s, 1H), 6.60-6.40 (m, 3H), 5.86 (s, 1H), 4.50-4.40 (m, 1H), 4.30-3.90 (m, 2H), 3.80 (s, 6H), 3.05-2.90 (m, 2H), 2.70-2.10 (m, 7H), 2.06 (s, 3H), 1.40-1.30 (m, 2H), 1.20-1.10 (m, 3H).

EXAMPLE 68(17)

N-(3-{1-[(2S,3S)-2-(2,3-dihydro-1H-inden-2-ylmethyl)-3-(3,5-dimethoxy-4-methylphenyl)-3-hydroxypropyl]-1H-pyrrol-3-yl}propanoyl)-2-fluorobenzenesulfonamide TLC: Rf 0.46 (hexane:ethyl acetate=1:1);
$^1$HNMR: δ 1.31-1.46 (m, 2H), 2.05 (s, 3H), 2.09-2.17 (m, 1H), 2.31-2.46 (m, 3H), 2.46-2.54 (m, 2H), 2.74 (t, 2H), 2.90-3.01 (m, 2H), 3.78 (s, 6H), 3.96-4.03 (m, 1H), 4.21 (dd, 1H), 4.43 (d, 1H), 5.93-5.96 (m, 1H), 6.52-6.57 (m, 3H), 6.63-6.67 (m, 1H), 7.07-7.19 (m, 5H), 7.25-7.32 (m, 1H), 7.56-7.64 (m, 1H), 8.00-8.06 (m, 1H), 8.34 (s, 1H).

EXAMPLE 68(18)

N-(3-{1-[(2S,3S)-2-(2,3-dihydro-1H-inden-2-ylmethyl)-3-(3,5-dimethoxy-4-methylphenyl)-3-hydroxypropyl]-1H-pyrrol-3-yl}propanoyl)-2-(trifluoromethyl)benzenesulfonamide TLC: Rf 0.53 (hexane:ethyl acetate=1:1);
$^1$HNMR: δ 1.30-1.45 (m, 2H), 2.05 (s, 3H), 2.07-2.17 (m, 1H), 2.37-2.52 (m, 5H), 2.69-2.77 (m, 2H), 2.90-3.02 (m, 2H), 3.79 (s, 6H), 3.98 (dd, 1H), 4.22 (dd, 1H), 4.42 (d, 1H), 5.89-5.94 (m, 1H), 6.51-6.58 (m, 3H), 6.61-6.67 (m, 1H), 7.05-7.15 (m, 4H), 7.69-7.77 (m, 2H), 7.80-7.87 (m, 1H), 8.30 (s, 1H), 8.43-8.49 (m, 1H).

EXAMPLE 68(19)

2,6-dichloro-N-(3-{1-[(2S,3S)-2-(2,3-dihydro-1H-inden-2-ylmethyl)-3-(3,5-dimethoxy-4-methylphenyl)-3-hydroxypropyl]-1H-pyrrol-3-yl}propanoyl)benzenesulfonamide TLC: Rf 0.39 (hexane:ethyl acetate=1:1);
$^1$HNMR: δ 1.30-1.45 (m, 2H), 2.04 (s, 3H), 2.07-2.17 (m, 1H), 2.33-2.46 (m, 3H), 2.53-2.60 (m, 2H), 2.73-2.81 (m, 2H), 2.90-3.02 (m, 2H), 3.79 (s, 6H), 3.99 (dd, 1H), 4.21 (dd, 1H), 4.43 (d, 1H), 5.44 (s, 1H), 5.94-5.98 (m, 1H), 6.53 (s, 2H), 6.55-6.61 (m, 1H), 6.63-6.67 (m, 1H), 7.04-7.14 (m, 4H), 7.31-7.38 (m, 1H), 7.41-7.49 (m, 2H), 8.55 (s, 1H).

EXAMPLE 68(20)

N-(3-{1-[(2S,3S)-2-(2,3-dihydro-1H-inden-2-ylmethyl)-3-(3,5-dimethoxy-4-methylphenyl)-3-hydroxypropyl]-1H-pyrrol-3-yl}propanoyl)-2-methylbenzenesulfonamide Property: amorphous;
TLC: Rf 0.68 (hexane:ethyl acetate=1:2);
$^1$HNMR: δ 8.14 (s, 1H), 8.10 (dd, 1H), 7.48 (ddd, 1H), 7.34 (dd, 1H), 7.26 (m, 1H), 7.18-7.05 (m, 4H), 6.65 (m, 1H), 6.58-6.52 (m, 3H), 5.93 (dd, 1H), 4.45 (d, 1H), 4.21 (dd, 1H), 3.99 (dd, 1H), 3.80 (s, 6H), 3.04-2.90 (m, 2H), 2.75 (t, 2H), 2.58-2.30 (m, 5H), 2.53 (s, 3H), 2.18 (m, 1H), 2.06 (s, 3H), 1.40 (m, 2H).

EXAMPLE 68(21)

N-(3-{1-[(2S,3S)-2-(2,3-dihydro-1H-inden-2-ylmethyl)-3-(3,5-dimethoxy-4-methylphenyl)-3-hydroxypropyl]-1H-pyrrol-3-yl}propanoyl)-2,6-difluorobenzenesulfonamide TLC: Rf 0.58 (hexane:ethyl acetate=1:2);
$^1$HNMR: δ 8.46 (s, 1H), 7.55 (m, 1H), 7.16-7.06 (m, 4H), 7.01 (dd, 2H), 6.67 (m, 1H), 6.57 (m, 1H), 6.54 (s, 2H), 5.96 (m, 1H), 4.44 (d, 1H), 4.21 (dd, 1H), 4.01 (dd, 1H), 3.81 (s, 6H), 3.04-2.92 (m, 2H), 2.77 (t, 2H), 2.55 (m, 2H), 2.50-2.30 (m, 3H), 2.15 (m, 1H), 2.06 (s, 3H), 1.40 (m, 2H).

EXAMPLE 68(22)

4-chloro-N-(3-{1-[(2S,3S)-2-(2,3-dihydro-1H-inden-2-ylmethyl)-3-(3,5-dimethoxy-4-methylphenyl)-3-hydroxypropyl]-1H-pyrrol-3-yl}propanoyl)-3-pyridinesulfonamide TLC: Rf 0.28 (hexane:ethyl acetate=1:2);
$^1$HNMR: δ 9.30 (s, 1H), 8.70 (d, 1H), 8.48 (s, 1H), 7.42 (d, 1H), 7.18-7.05 (m, 4H), 6.67 (m, 1H), 6.59 (m, 1H), 6.54 (s, 2H), 5.97 (m, 1H), 4.44 (d, 1H), 4.23 (dd, 1H), 4.02 (dd, 1H), 3.80 (s, 6H), 3.02-2.90 (m, 2H), 2.78 (t, 2H), 2.55 (m, 2H), 2.50-2.30 (m, 3H), 2.14 (m, 1H), 2.06 (s, 3H), 1.40 (m, 2H).

EXAMPLE 68(23)

N-(3-{1-[(2S,3S)-2-(2,3-dihydro-1H-inden-2-ylmethyl)-3-(4-ethyl-3,5-dimethoxyphenyl)-3-hydroxypropyl]-1H-pyrrol-3-yl}propanoyl)methanesulfonamide TLC: Rf 0.28 (hexane:ethyl acetate=1:1);
$^1$HNMR: δ 1.05 (t, 3H), 1.33-1.42 (m, 2H), 2.08-2.18 (m, 1H), 2.32-2.47 (m, 3H), 2.53-2.66 (m, 4H), 2.78-2.87 (m, 2H), 2.90-3.02 (m, 2H), 3.20 (s, 3H), 3.81 (s, 6H), 3.96-4.05 (m, 1H), 4.13-4.22 (m, 1H), 4.42 (d, 1H), 5.97-6.01 (m, 1H), 6.52 (s, 2H), 6.55-6.60 (m, 1H), 6.63-6.68 (m, 1H), 7.06-7.15 (m, 4H), 7.84 (s, 1H).

EXAMPLE 68(24)

N-(3-{1-[(2S,3S)-2-(2,3-dihydro-1H-inden-2-ylmethyl)-3-(4-ethyl-3,5-dimethoxyphenyl)-3-hydroxypropyl]-1H-pyrrol-3-yl}propanoyl)benzenesulfonamide TLC: Rf 0.49 (hexane:ethyl acetate=1:1);
¹HNMR: δ 1.05 (t, 3H), 1.33-1.44 (m, 2H), 2.08-2.18 (m, 1H), 2.35-2.49 (m, 5H), 2.62 (q, 2H), 2.69-2.77 (m, 2H), 2.89-3.02 (m, 2H), 3.80 (s, 6H), 3.95-4.04 (m, 1H), 4.13-4.22 (m, 1H), 4.45 (d, 1H), 5.86-5.91 (m, 1H), 6.47-6.56 (m, 3H), 6.60-6.66 (m, 1H), 7.06-7.16 (m, 4H), 7.46-7.53 (m, 2H), 7.58-7.64 (m, 1H), 7.94-8.03 (m, 3H).

EXAMPLE 68(25)

N-(2-{1-[(2S,3S)-2-(2,3-dihydro-1H-inden-2-ylmethyl)-3-(4-ethyl-3,5-dimethoxyphenyl)-3-hydroxypropyl]-1H-pyrrol-3-yl}acetyl)methanesulfonamide TLC: Rf 0.24 (hexane:ethyl acetate=1:1);
¹HNMR: δ 1.05 (t, 3H), 1.32-1.45 (m, 2H), 2.09-2.19 (m, 1H), 2.32-2.48 (m, 3H), 2.62 (q, 2H), 2.91-3.04 (m, 2H), 3.24 (s, 3H), 3.56 (s, 2H), 3.81 (s, 6H), 4.00-4.11 (m, 1H), 4.13-4.25 (m, 1H), 4.43 (d, 1H), 5.99-6.04 (m, 1H), 6.50 (s, 2H), 6.64-6.71 (m, 2H), 7.06-7.16 (m, 4H), 8.06 (s, 1H).

EXAMPLE 68(26)

N-(2-{1-[(2S,3S)-2-(2,3-dihydro-1H-inden-2-ylmethyl)-3-(4-ethyl-3,5-dimethoxyphenyl)-3-hydroxypropyl]-1H-pyrrol-3-yl}acetyl)benzenesulfonamide TLC: Rf 0.46 (hexane:ethyl acetate=1:1);
¹HNMR: δ 1.06 (t, 3H), 1.34-1.45 (m, 2H), 2.10-2.18 (m, 1H), 2.33-2.49 (m, 3H), 2.63 (q, 2H), 2.91-3.03 (m, 2H), 3.44 (s, 2H), 3.81 (s, 6H), 3.99-4.08 (m, 1H), 4.11-4.25 (m, 1H), 4.43 (d, 1H), 5.93-5.96 (m, 1H), 6.51 (s, 2H), 6.59-6.63 (m, 1H), 6.67-6.70 (m, 1H), 7.07-7.16 (m, 4H), 7.47-7.54 (m, 2H), 7.59-7.66 (m, 1H), 7.97-8.02 (m, 2H), 8.21 (s, 1H).

EXAMPLE 68(27)

N-(2-{1-[(2S,3S)-2-(2,3-dihydro-1H-inden-2-ylmethyl)-3-(3,5-dimethoxy-4-methylphenyl)-3-hydroxypropyl]-1H-pyrrol-3-yl}-2-methylpropanoyl)benzenesulfonamide TLC: Rf 0.58 (hexane:ethyl acetate=1:1);
¹HNMR: δ 8.14 (s, 1H), 7.94 (d, 2H), 7.60 (m, 1H), 7.49 (m, 2H), 7.18-7.05 (m, 4H), 6.69 (dd, 1H), 6.58 (dd, 1H), 6.53 (s, 2H), 5.94 (dd, 1H), 4.45 (d, 1H), 4.20 (dd, 1H), 4.04 (dd, 1H), 3.83 (s, 6H), 3.04-2.90 (m, 2H), 2.55-2.35 (m, 3H), 2.18 (m, 1H), 2.07 (s, 3H), 1.50-1.38 (m, 2H), 1.41(s, 3H), 1.40 (s, 3H).

EXAMPLE 68(28)

2-chloro-N-(3-{1-[(2S,3S)-2-(2,3-dihydro-1H-inden-2-ylmethyl)-3-(3,5-dimethoxy-4-methylphenyl)-3-hydroxypropyl]-1H-pyrrol-3-yl}propanoyl)benzenesulfonamide TLC: Rf 0.40 (hexane:ethyl acetate=1:1);
¹HNMR: δ 1.29-1.50 (m, 2H), 2.05 (s, 3H), 2.08-2.22 (m, 1H), 2.28-2.50 (m, 3H), 2.50-2.60 (m, 2H), 2.77 (t, 2H), 2.90-3.05 (m, 2H), 3.79 (s, 6H), 4.00 (dd, 1H), 4.23 (dd, 1H), 4.43 (dd, 1H), 5.93-6.01 (m, 1H), 6.54 (s, 2H), 6.59 (s, 1H), 6.66 (t, 1H), 7.00-7.20 (m, 4H), 7.38-7.60 (m, 3H), 8.17-8.27 (m, 1H), 8.37 (s, 1H).

EXAMPLE 68(29)

methyl2-{[(3-{1-[(2S,3S)-2-(2,3-dihydro-1H-inden-2-ylmethyl)-3-(3,5-dimethoxy-4-methylphenyl)-3-hydroxypropyl]-1H-pyrrol-3-yl}propanoyl)amino]sulfonyl}benzoate TLC: Rf 0.29 (hexane:ethyl acetate=1:1);
¹HNMR: δ 1.29-1.45 (m, 2H), 2.01-2.20 (m, 5H), 2.27-2.50 (m, 3H), 2.51-2.61 (m, 2H), 2.76 (t, 2H), 2.94 (dd, 2H), 3.80 (s, 6H), 3.90-4.00 (m, 4H), 4.12-4.24 (m, 1H), 4.41 (dd, 1H), 5.92 (t, 1H), 6.51 (s, 2H), 6.53 (s, 1H), 6.57 (t, 1H), 7.00-7.19 (m, 4H), 7.58-7.71 (m, 2H), 7.73-7.82 (m, 1H), 8.21-8.35 (m, 1H), 8.58 (s, 1H).

EXAMPLE 68(30)

3-chloro-N-(3-{1-[(2S,3S)-2-(2,3-dihydro-1H-inden-2-ylmethyl)-3-(3,5-dimethoxy-4-methylphenyl)-3-hydroxypropyl]-1H-pyrrol-3-yl}propanoyl)benzenesulfonamide TLC: Rf 0.34 (hexane:ethyl acetate=1:1);
¹HNMR: δ 1.29-1.49 (m, 2H), 2.02 (d, 1H), 2.06 (s, 3H), 2.08-2.24 (m, 1H), 2.28-2.58 (m, 5H), 2.74 (t, 2H), 2.85-3.08 (m, 2H), 3.80 (s, 6H), 3.94-4.07 (m, 1H), 4.13-4.25 (m, 1H), 4.45 (dd, 1H), 5.84-5.91 (m, 1H), 6.50-6.52 (m, 1H), 6.53 (s, 2H), 6.65 (t, 1H), 6.99-7.19 (m, 4H), 7.43 (t, 1H), 7.51-7.63 (m, 1H), 7.83-8.14 (m, 3H).

EXAMPLE 68(31)

N-(3-{1-[(2S,3S)-2-(2,3-dihydro-1H-inden-2-ylmethyl)-3-(3,5-dimethoxy-4-methylphenyl)-3-hydroxypropyl]-1H-pyrrol-3-yl}propanoyl)-2-thiophenesulfonamide TLC: Rf 0.30 (hexane:ethyl acetate=1:1);
¹HNMR: δ 1.29-1.48 (m, 2H), 2.02 (d, 1H), 2.06 (s, 3H), 2.08-2.21 (m, 1H), 2.28-2.62 (m, 5H), 2.75 (t, 2H), 2.87-3.05 (m, 2H), 3.81 (s, 6H), 3.98 (dd, 1H), 4.18 (dd, 1H), 4.44 (dd, 1H), 5.79-5.96 (m, 1H), 6.50 (s, 1H), 6.54 (s, 2H), 6.64 (t, 1H), 7.01-7.20 (m, 5H), 7.63 (dd, 1H), 7.82 (dd, 1H), 8.04 (s, 1H).

EXAMPLE 68(32)

N-(2-{1-[(2S,3S)-2-(2,3-dihydro-1H-inden-2-ylmethyl)-3-(3,5-dimethoxy-4-methylphenyl)-3-hydroxypropyl]-1H-pyrrol-3-yl}-2-methylpropanoyl)methanesulfonamide TLC: Rf 0.34 (hexane:ethyl acetate=1:1);
¹HNMR: δ 7.95 (s, 1H), 7.18-7.05 (m, 4H), 6.70 (dd, 1H), 6.63 (dd, 1H), 6.51 (s, 2H), 6.05 (dd, 1H), 4.43 (d, 1H), 4.19 (dd, 1H), 4.04 (dd, 1H), 3.82 (s, 6H), 3.19 (s, 3H), 3.08-2.90 (m, 2H), 2.52-2.28 (m, 3H), 2.14 (m, 1H), 2.06 (s, 3H), 1.53 (s, 6H), 1.40 (m, 2H).

EXAMPLE 68(33)

N-({1-[(2S,3S)-2-(2,3-dihydro-1H-inden-2-ylmethyl)-3-(3,5-dimethoxy-4-methylphenyl)-3-hydroxypropyl]-1H-pyrrol-3-yl}acetyl)-4-methylbenzenesulfonamide TLC: Rf 0.33 (hexane:ethyl acetate=1:1);
$^1$HNMR: δ 8.20 (s, 1H), 7.87 (d, 2H), 7.29 (d, 2H), 7.18-7.06 (m, 4H), 6.69 (m, 1H), 6.61 (m, 1H), 6.51 (s, 2H), 5.94 (m, 1H), 4.42 (d, 1H), 4.22 (dd, 1H), 4.03 (dd, 1H), 3.82 (s, 6H), 3.43 (s, 2H), 3.04-2.92 (m, 2H), 2.58-2.30 (m, 3H), 2.43 (s, 3H), 2.15 (m, 1H), 2.07 (s, 3H), 1.40 (m, 2H).

EXAMPLE 68(34)

4-chloro-N-({1-[(2S,3S)-2-(2,3-dihydro-1H-inden-2-ylmethyl)-3-(3,5-dimethoxy-4-methylphenyl)-3-hydroxypropyl]-1H-pyrrol-3-yl}acetyl)benzenesulfonamide TLC: Rf 0.33 (hexane:ethyl acetate=1:1);
$^1$HNMR: δ 8.21 (s, 1H), 7.92 (d, 2H), 7.47 (d, 2H), 7.17-7.05 (m, 4H), 6.69 (dd, 1H), 6.61 (m, 1H), 6.51 (s, 2H), 5.94 (dd, 1H), 4.43 (dd, 1H), 4.20 (dd, 1H), 4.03 (dd, 1H), 3.82 (s, 6H), 3.44 (s, 2H), 3.04-2.92 (m, 2H), 2.52-2.30 (m, 3H), 2.15 (m, 1H), 2.07 (s, 3H), 1.39 (m, 2H).

EXAMPLE 68(35)

N-({1-[(2S,3S)-2-(2,3-dihydro-1H-inden-2-ylmethyl)-3-(3,5-dimethoxy-4-methylphenyl)-3-hydroxypropyl]-1H-pyrrol-3-yl}acetyl)-4-fluorobenzenesulfonamide TLC: Rf 0.32 (hexane:ethyl acetate=1:1);
$^1$HNMR: δ 8.21 (s, 1H), 8.01 (dd, 2H), 7.17 (dd, 2H), 7.17-7.06 (m, 4H), 6.69 (dd, 1H), 6.61 (m, 1H), 6.51 (s, 2H), 5.94 (dd, 1H), 4.43 (dd, 1H), 4.20 (dd, 1H), 4.03 (dd, 1H), 3.82 (s, 6H), 3.44 (s, 2H), 3.04-2.90 (m, 2H), 2.55-2.30 (m, 3H), 2.15 (m, 1H), 2.07 (s, 3H), 1.40 (m, 2H).

EXAMPLE 68(36)

N-(3-{1-[(2S,3S)-2-(2,3-dihydro-1H-inden-2-ylmethyl)-3-(3,5-dimethoxy-4-methylphenyl)-3-hydroxypropyl]-1H-pyrrol-3-yl}propanoyl)-2-(trifluoromethoxy)benzenesulfonamide TLC: Rf 0.53 (hexane:ethyl acetate=1:1);
$^1$HNMR: δ 1.27-1.48 (m, 2H), 2.01-2.21 (m, 4H), 2.27-2.57 (m, 5H), 2.75 (t, 2H), 2.88-3.06 (m, 2H), 3.80 (s, 6H), 3.99 (dd, 1H), 4.21 (dd, 1H), 4.42 (d, 1H), 5.92-5.99 (m, 1H), 6.53 (s, 2H), 6.56 (s, 1H), 6.64 (t, 1H), 7.03-7.19 (m, 4H), 7.34-7.49 (m, 2H), 7.61-7.72 (m, 1H), 8.17 (dd, 1H).

EXAMPLE 68(37)

6-chloro-N-(3-{1-[(2S,3S)-2-(2,3-dihydro-1H-inden-2-ylmethyl)-3-(3,5-dimethoxy-4-methylphenyl)-3-hydroxypropyl]-1H-pyrrol-3-yl}propanoyl)-3-pyridinesulfonamide TLC: Rf 0.17 (hexane:ethyl acetate=1:1);
$^1$HNMR: δ 1.38 (t, 2H), 1.99-2.23 (m, 4H), 2.28-2.56 (m, 5H), 2.74 (t, 2H), 2.87-3.04 (m, 2H), 3.81 (s, 6H), 3.94-4.06 (m, 1H), 4.12-4.25 (m, 1H), 4.43 (d, 1H), 5.84-5.90 (m, 1H), 6.48-6.50 (m, 1H), 6.53 (s, 2H), 6.65 (t, 1H), 7.01-7.20 (m, 4H), 7.45 (d, 1H), 8.26 (dd, 1H), 8.85 (dd, 1H).

EXAMPLE 68(38)

N'-(3-{1-[(2S,3S)-2-(2,3-dihydro-1H-inden-2-ylmethyl)-3-(3,5-dimethoxy-4-methylphenyl)-3-hydroxypropyl]-1H-pyrrol-3-yl}propanoyl)-N,N-dimethylsulfamide TLC: Rf 0.44 (hexane:ethyl acetate=1:1);
$^1$HNMR: δ 1.30-1.47 (m, 2H), 2.01-2.20 (m, 4H), 2.27-2.48 (m, 3H), 2.48-2.57 (m, 2H), 2.81 (t, 2H), 2.88 (s, 6H), 2.90-3.04 (m, 2H), 3.81 (s, 6H), 3.93-4.04 (m, 1H), 4.15-4.26 (m, 1H), 4.42 (dd, 1H), 5.96-6.03 (m, 1H), 6.52 (s, 2H), 6.57 (s, 1H), 6.64 (t, 1H), 7.03-7.17 (m, 4H), 7.74 (s, 1H).

EXAMPLE 68(39)

N-(3-{1-[(2S,3S)-2-(2,3-dihydro-1H-inden-2-ylmethyl)-3-(3,5-dimethoxy-4-methylphenyl)-3-hydroxypropyl]-1H-pyrrol-3-yl}propanoyl)-1-methyl-1H-imidazole-4-sulfonamide TLC: Rf 0.27 (ethyl acetate);
$^1$HNMR: δ 1.23-1.47 (m, 2H), 2.04 (s, 3H), 2.06-2.21 (m, 1H), 2.26-2.62 (m, 5H), 2.74 (t, 2H), 2.84-3.05 (m, 2H), 3.67 (s, 3H), 3.78 (s, 6H), 3.95 (dd, 1H), 4.24 (dd, 1H), 4.38 (d, 1H), 5.91-5.96 (m, 1H), 6.49-6.55 (m, 2H), 6.56-6.65 (m, 2H), 7.03-7.17 (m, 4H), 7.37 (d, 1H), 7.61 (d, 1H).

EXAMPLE 68(40)

N-({1-[(2S,3S)-2-(2,3-dihydro-1H-inden-2-ylmethyl)-3-(3,5-dimethoxy-4-methylphenyl)-3-hydroxypropyl]-1H-pyrrol-3-yl}acetyl)-2-methylbenzenesulfonamide TLC: Rf 0.39 (hexane:ethyl acetate=1:1);
$^1$HNMR: δ 1.31-1.42 (m, 2H), 1.92-2.00 (m, 1H), 2.06 (s, 3H), 2.09-2.19 (m, 1H), 2.35-2.50 (m, 6H), 2.90-3.04 (m, 2H), 3.43 (s, 2H), 3.81 (s, 6H), 4.02 (dd, 1H), 4.24 (dd, 1H), 4.42 (d, 1H), 5.93-6.00 (m, 1H), 6.51 (s, 2H), 6.62-6.73 (m, 2H), 7.05-7.15 (m, 4H), 7.22-7.30 (m, 1H), 7.30-7.40 (m, 1H), 7.43-7.52 (m, 1H), 8.09-8.17 (m, 1H), 8.29 (s, 1H).

EXAMPLE 68(41)

N-({1-[(2S,3S)-2-(2,3-dihydro-1H-inden-2-ylmethyl)-3-(3,5-dimethoxy-4-methylphenyl)-3-hydroxypropyl]-1H-pyrrol-3-yl}acetyl)-2-(trifluoromethyl)benzenesulfonamide TLC: Rf 0.43 (hexane:ethyl acetate=1:1);
$^1$HNMR: δ 1.31-1.41 (m, 2H), 1.85-2.00 (m, 1H), 2.05 (s, 3H), 2.09-2.17 (m, 1H), 2.34-2.49 (m, 3H), 2.90-3.03 (m, 2H), 3.44 (s, 2H), 3.81 (s, 6H), 4.02 (dd, 1H), 4.29 (dd, 1H), 4.38 (d, 1H), 5.93-5.99 (m, 1H), 6.51 (s, 2H), 6.62-6.67 (m, 1H), 6.68-6.74 (m, 1H), 7.05-7.15 (m, 4H), 7.72-7.86 (m, 3H), 8.38-8.45 (m, 1H), 8.48-8.54 (m, 1H).

EXAMPLE 68(42)

N-({1-[(2S,3S)-2-(2,3-dihydro-1H-inden-2-ylmethyl)-3-(3,5-dimethoxy-4-methylphenyl)-3-hydroxypropyl]-1H-pyrrol-3-yl}acetyl)-2-fluorobenzenesulfonamide TLC: Rf 0.35 (hexane:ethyl acetate=1:1);
$^1$HNMR: δ 1.32-1.42 (m, 2H), 1.89-2.01 (m, 1H), 2.05 (s, 3H), 2.09-2.18 (m, 1H), 2.35-2.49 (m, 3H), 2.91-3.04 (m, 2H), 3.46 (s, 2H), 3.80 (s, 6H), 4.03 (dd, 1H), 4.27 (dd, 1H), 4.40 (d, 1H), 5.97-6.03 (m, 1H), 6.51 (s, 2H), 6.64-6.74 (m, 2H), 7.05-7.18 (m, 5H), 7.27-7.35 (m, 1H), 7.56-7.66 (m, 1H), 8.03-8.12 (m, 1H), 8.47 (s, 1H).

EXAMPLE 68(43)

2-chloro-N-({1-[(2S,3S)-2-(2,3-dihydro-1H-inden-2-ylmethyl)-3-(3,5-dimethoxy-4-methylphenyl)-3-hydroxypropyl]-1H-pyrrol-3-yl}acetyl)benzenesulfonamide TLC: Rf 0.39 (hexane:ethyl acetate=1:1);
$^1$HNMR: δ 1.32-1.42 (m, 2H), 1.89-1.99 (m, 1H), 2.05 (s, 3H), 2.09-2.19 (m, 1H), 2.35-2.49 (m, 3H), 2.91-3.04 (m, 2H), 3.46 (s, 2H), 3.81 (s, 6H), 3.99-4.08 (m, 1H), 4.27 (dd, 1H), 4.40 (d, 1H), 6.00-6.05 (m, 1H), 6.51 (s, 2H), 6.65-6.73 (m, 2H), 7.05-7.15 (m, 4H), 7.43-7.57 (m, 3H), 8.23-8.30 (m, 1H), 8.51 (s, 1H).

EXAMPLE 68(44)

N-({1-[(2S,3S)-2-(2,3-dihydro-1H-inden-2-ylmethyl)-3-(3,5-dimethoxy-4-methylphenyl)-3-hydroxypropyl]-1H-pyrrol-3-yl}acetyl)-2,6-difluorobenzenesulfonamide TLC: Rf 0.22 (hexane:ethyl acetate=1:1);
$^1$HNMR: δ 1.32-1.41 (m, 2H), 1.90-2.01 (m, 1H), 2.05 (s, 3H), 2.08-2.18 (m, 1H), 2.34-2.48 (m, 3H), 2.90-3.03 (m, 2H), 3.50 (s, 2H), 3.80 (s, 6H), 4.03 (dd, 1H), 4.25 (dd, 1H), 4.40 (d, 1H), 5.97-6.03 (m, 1H), 6.50 (s, 2H), 6.64-6.73 (m, 2H), 6.97-7.13 (m, 6H), 7.48-7.60 (m, 1H), 8.57 (s, 1H).

EXAMPLE 68(45)

2,6-dichloro-N-({1-[(2S,3S)-2-(2,3-dihydro-1H-inden-2-ylmethyl)-3-(3,5-dimethoxy-4-methylphenyl)-3-hydroxypropyl]-1H-pyrrol-3-yl}acetyl)benzenesulfonamide TLC: Rf 0.35 (hexane:ethyl acetate=1:1);
$^1$HNMR: δ 1.32-1.40 (m, 2H), 1.88-2.00 (m, 1H), 2.05 (s, 3H), 2.08-2.18 (m, 1H), 2.34-2.49 (m, 3H), 2.90-3.04 (m, 2H), 3.48 (s, 2H), 3.81 (s, 6H), 4.02 (dd, 1H), 4.25 (dd, 1H), 4.40 (d, 1H), 5.99-6.05 (m, 1H), 6.51 (s, 2H), 6.64-6.72 (m, 2H), 7.05-7.15 (m, 4H), 7.32-7.39 (m, 1H), 7.42-7.49 (m, 2H), 8.64 (s, 1H).

EXAMPLE 68(46)

N-({1-[(2S,3S)-2-(2,3-dihydro-1H-inden-2-ylmethyl)-3-(3,5-dimethoxy-4-methylphenyl)-3-hydroxypropyl]-1H-pyrrol-3-yl}acetyl)-3-fluorobenzenesulfonamide TLC: Rf 0.35 (hexane:ethyl acetate=1:1);
$^1$HNMR: δ 1.30-1.42 (m, 2H), 2.06 (s, 3H), 2.08-2.17 (m, 1H), 2.34-2.48 (m, 3H), 2.90-3.03 (m, 2H), 3.45 (s, 2H), 3.81 (s, 6H), 3.98-4.07 (m, 1H), 4.17-4.25 (m, 1H), 4.42 (d, 1H), 5.90-5.96 (m, 1H), 6.47-6.52 (m, 2H), 6.59-6.64 (m, 1H), 6.66-6.71 (m, 1H), 7.04-7.15 (m, 4H), 7.27-7.35 (m, 1H), 7.44-7.53 (m, 1H), 7.64-7.72 (m, 1H), 7.76-7.81 (m, 1H), 8.24 (s, 1H).

EXAMPLE 68(47)

3-chloro-N-({1-[(2S,3S)-2-(2,3-dihydro-1H-inden-2-ylmethyl)-3-(3,5-dimethoxy-4-methylphenyl)-3-hydroxypropyl]-1H-pyrrol-3-yl}acetyl)benzenesulfonamide TLC: Rf 0.37 (hexane:ethyl acetate=1:1);
$^1$HNMR: δ 1.31-1.42 (m, 2H), 2.06 (s, 3H), 2.10-2.18 (m, 1H), 2.34-2.48 (m, 3H), 2.90-3.04 (m, 2H), 3.45 (s, 2H), 3.81 (s, 6H), 3.97-4.07 (m, 1H), 4.21 (dd, 1H), 4.42 (d, 1H), 5.91-5.97 (m, 1H), 6.50 (s, 2H), 6.59-6.64 (m, 1H), 6.66-6.72 (m, 1H), 7.05-7.15 (m, 4H), 7.38-7.50 (m, 1H), 7.54-7.61 (m, 1H), 7.86-7.92 (m, 1H), 7.93-7.98 (m, 1H), 8.24 (s, 1H).

EXAMPLE 68(48)

N-(2-{1-[(2S,3S)-2-(2,3-dihydro-1H-inden-2-ylmethyl)-3-(3,5-dimethoxy-4-methylphenyl)-3-hydroxypropyl]-1H-pyrrol-3-yl}acetyl)-2-thiophenesulfonamide TLC: Rf 0.30 (hexane:ethyl acetate=1:1);
$^1$HNMR: δ 1.30-1.40 (m, 2H), 1.88-2.00 (m, 1H), 2.05 (s, 3H), 2.08-2.17 (m, 1H), 2.31-2.46 (m, 3H), 2.89-3.02 (m, 2H), 3.47 (s, 2H), 3.81 (s, 6H), 3.97-4.06 (m, 1H), 4.15-4.25 (m, 1H), 4.41 (d, 1H), 5.93-5.97 (m, 1H), 6.50 (s, 2H), 6.59-6.63 (m, 1H), 6.65-6.70 (m, 1H), 7.05-7.14 (m, 5H), 7.60-7.66 (m, 1H), 7.81-7.86 (m, 1H), 8.30 (s, 1H).

EXAMPLE 68(49)

N-({1-[(2S,3S)-2-(2,3-dihydro-1H-inden-2-ylmethyl)-3-(3,5-dimethoxy-4-methylphenyl)-3-hydroxypropyl]-1H-pyrrol-3-yl}acetyl)-3,5-dimethyl-4-isoxazolesulfonamide TLC: Rf 0.37 (hexane:ethyl acetate=1:1);
$^1$HNMR: δ 1.30-1.41 (m, 2H), 1.88-2.00 (m, 1H), 2.05 (s, 3H), 2.08-2.19 (m, 1H), 2.28 (s, 3H), 2.31-2.46 (m, 3H), 2.70 (s, 3H), 2.89-3.03 (m, 2H), 3.45 (s, 2H), 3.81 (s, 6H), 3.98-4.07 (m, 1H), 4.17-4.26 (m, 1H), 4.42 (d, 1H), 5.92-5.97 (m, 1H), 6.49 (s, 2H), 6.60-6.65 (m, 1H), 6.67-6.71 (m, 1H), 7.05-7.14 (m, 4H), 8.31 (s, 1H).

EXAMPLE 68(50)

N-(3-{1-[(2S,3S)-2-(2,3-dihydro-1H-inden-2-ylmethyl)-3-(3,5-dimethoxy-4-methylphenyl)-3-hydroxypropyl]-1H-pyrrol-3-yl}propanoyl)-2,4-difluorobenzenesulfonamide TLC: Rf 0.52 (hexane:ethyl acetate=1:1);
$^1$HNMR: δ 1.29-1.49 (m, 2H), 2.01-2.21 (m, 5H), 2.28-2.56 (m, 5H), 2.75 (t, 2H), 2.87-3.05 (m, 2H), 3.79 (s, 6H), 3.94-4.04 (m, 1H), 4.20 (dd, 1H), 4.43 (d, 1H), 5.91-5.96 (m, 1H), 6.52 (s, 2H), 6.53-6.57 (m, 1H), 6.65 (t, 1H), 6.84-6.93 (m, 1H), 6.96-7.05 (m, 1H), 7.05-7.15 (m, 4H), 7.98-8.12 (m, 1H).

EXAMPLE 68(51)

2-chloro-N-(3-{1-[(2S,3S)-2-(2,3-dihydro-1H-inden-2-ylmethyl)-3-(3,5-dimethoxy-4-methylphenyl)-3-hydroxypropyl]-1H-pyrrol-3-yl}propanoyl)-6-methylbenzenesulfonamide TLC: Rf 0.62 (hexane:ethyl acetate=1:1);
$^1$HNMR: δ 1.28-1.50 (m, 2H), 1.98-2.23 (m, 5H), 2.28-2.49 (m, 3H), 2.49-2.61 (m, 2H), 2.71-2.82 (m, 5H), 2.88-3.08 (m, 2H), 3.79 (s, 6H), 3.99 (dd, 1H), 4.21 (dd, 1H), 4.42 (dd, 1H), 5.92-5.99 (m, 1H), 6.53 (s, 2H), 6.57 (s, 1H), 6.65 (t, 1H), 7.05-7.15 (m, 4H), 7.18-7.23 (m, 1H), 7.29-7.35 (m, 2H), 8.49 (s, 1H).

EXAMPLE 68(52)

N-(3-{1-[(2S,3S)-2-(2,3-dihydro-1H-inden-2-ylmethyl)-3-(3,5-dimethoxy-4-methylphenyl)-3-hydroxypropyl]-1H-pyrrol-3-yl}propanoyl)-2-methoxy-4-methylbenzenesulfonamide TLC: Rf 0.29 (hexane:ethyl acetate=1:1);
$^1$HNMR: δ 1.28-1.47 (m, 2H), 2.05 (s, 3H), 2.09-2.18 (m, 2H), 2.28-2.48 (m, 6H), 2.48-2.57 (m, 2H), 2.72 (t, 2H), 2.86-3.04 (m, 2H), 3.78 (s, 6H), 3.90 (s, 3H), 3.93-4.02 (m, 1H), 4.14-4.24 (m, 1H), 4.40 (dd, 1H), 5.89-5.95 (m, 1H), 6.51 (s, 2H), 6.54 (s, 1H), 6.60 (t, 1H), 6.77 (s, 1H), 6.85 (dd, 1H), 7.02-7.17 (m, 4H), 7.86 (d, 1H), 8.27 (s, 1H).

EXAMPLE 68(53)

N-(3-{1-[(2S,3S)-2-(2,3-dihydro-1H-inden-2-ylmethyl)-3-(3,5-dimethoxy-4-methylphenyl)-3-hydroxypropyl]-1H-pyrrol-3-yl}propanoyl)-4-fluoro-2-methylbenzenesulfonamide TLC: Rf 0.51 (hexane:ethyl acetate=1:1);
$^1$HNMR: δ 1.25-1.48 (m, 2H), 2.01-2.18 (m, 5H), 2.27-2.57 (m, 8H), 2.75 (t, 2H), 2.89-3.05 (m, 2H), 3.80 (s, 6H), 3.99 (dd, 1H), 4.19 (dd, 1H), 4.38-4.49 (m, 1H), 5.88-5.95 (m, 1H), 6.50-6.57 (m, 3H), 6.64 (t, 1H), 6.90-7.05 (m, 2H), 7.06-7.15 (m, 4H), 8.11 (dd, 2H).

EXAMPLE 68(54)

N-(3-{1-[(2S,3S)-2-(2,3-dihydro-1H-inden-2-ylmethyl)-3-(3,5-dimethoxy-4-methylphenyl)-3-hydroxypropyl]-1H-pyrrol-3-yl}propanoyl)-5-methyl-2-furansulfonamide TLC: Rf 0.42 (hexane ethyl acetate=1:1);
$^1$HNMR: δ 1.28-1.50 (m, 2H), 1.99-2.08 (m, 4H), 2.09-2.22 (m, 1H), 2.28-2.49 (m, 6H), 2.49-2.65 (m, 2H), 2.77 (t, 2H), 2.86-3.07 (m, 2H), 3.80 (s, 6H), 4.00 (dd, 1H), 4.20 (dd, 1H), 4.44 (d, 1H), 5.93-5.97 (m, 1H), 6.13 (dd, 1H), 6.53 (s, 2H), 6.56 (t, 1H), 6.64 (t, 1 H), 7.07-7.15 (m, 4 H), 7.18 (d, 1H), 8.00 (s, 1H).

EXAMPLE 68(55)

N-(3-{1-[(2S,3S)-2-(2,3-dihydro-1H-inden-2-ylmethyl)-3-(3,5-dimethoxy-4-methylphenyl)-3-hydroxypropyl]-1H-pyrrol-3-yl}propanoyl)-1,3-thiazole-2-sulfonamide TLC: Rf 0.22 (hexane:ethyl acetate=1:4);
$^1$HNMR- δ 1.29-1.50 (m, 2H), 2.05 (s, 3H), 2.08-2.22 (m, 1H), 2.22-2.52 (m, 4H), 2.51-2.61 (m, 2H), 2.72-2.82 (m, 2H), 2.89-3.06 (m, 2H), 3.76-3.83 (m, 6H), 3.98 (dd, 1H), 4.20 (dd, 1H), 4.42 (d, 1H), 5.92-5.97 (m, 1H), 6.49-6.53 (m, 2H), 6.56 (s, 1H), 6.63 (t, 1H), 7.02-7.18 (m, 4H), 7.67 (d, 1H), 7.91 (d, 1H).

EXAMPLE 68(56)

N-({1-[(2S,3S)-2-(2,3-dihydro-1H-inden-2-ylmethyl)-3-(3,5-dimethoxy-4-methylphenyl)-3-hydroxypropyl]-1H-pyrrol-3-yl}acetyl)-4-(trifluoromethyl)benzenesulfonamide TLC: Rf 0.27 (hexane:ethyl acetate=1:1);
$^1$HNMR: δ 8.28 (s, 1H), 8.12 (d, 2H), 7.77 (d, 2H), 7.18-7.06 (m, 4H), 6.70 (m, 1H), 6.62 (m, 1H), 6.51 (s, 2H), 5.95 (m, 1H), 4.44 (d, 1H), 4.20 (dd, 1H), 4.04 (dd ,1H), 3.82 (s, 6H), 3.45 (s, 2H), 3.08-2.90 (m, 2H), 2.52-2.30 (m, 3H), 2.18 (m, 1H), 2.07 (s, 3H), 1.40 (m, 2H).

EXAMPLE 68(57)

N-({1-[(2S,3S)-2-(2,3-dihydro-1H-inden-2-ylmethyl)-3-(3,5-dimethoxy-4-methylphenyl)-3-hydroxypropyl]-1H-pyrrol-3-yl}acetyl)-4-methoxybenzenesulfonamide TLC: Rf 0.27 (hexane:ethyl acetate=1:1);
$^1$HNMR: δ 8.19 (s, 1H), 7.93 (d, 2H), 7.19-7.06 (m, 4H), 6.95 (d, 2H), 6.68 (dd, 1H), 6.61 (m, 1H), 6.51 (s, 2H), 5.94 (dd, 1H), 4.42 (d, 1H), 4.22 (dd, 1H), 4.03 (dd, 1H), 3.86 (s, 3H), 3.82 (s, 6H), 3.43 (s, 2H), 3.05-2.92 (m, 2H), 2.55-2.30 (m, 3H), 2.15 (m, 1H), 2.07 (s, 3H), 1.40 (m, 2H).

EXAMPLE 68(58)

N-({1-[(2S,3S)-2-(2,3-dihydro-1H-inden-2-ylmethyl)-3-(3,5-dimethoxy-4-methylphenyl)-3-hydroxypropyl]-1H-pyrrol-3-yl}acetyl)-2-methyl-2-propanesulfonamide TLC: Rf 0.27 (hexane:ethyl acetate=1:1);
$^1$HNMR: δ 7.66 (s, 1H), 7.18-7.04 (m, 4H), 6.73 (m, 2H), 6.51 (s, 2H), 6.03 (dd, 1H), 4.40 (d, 1H), 4.24 (dd, 1H), 4.03 (dd, 1H), 3.82 (s, 6H), 3.56 (s, 2H), 3.04-2.92 (m, 2H), 2.58-2.30 (m, 3H), 2.15 (m, 1H), 2.06 (s, 3H), 1.39 (s, 9H), 1.35 (m, 2H).

EXAMPLE 68(59)

N-(3-{1-[(2S,3S)-2-(2,3-dihydro-1H-inden-2-ylmethyl)-3-(3,5-dimethoxy-4-methylphenyl)-3-hydroxypropyl]-1H-pyrrol-3-yl}propanoyl)-4-morpholinesulfonamide TLC: Rf 0.30 (hexane:ethyl acetate=1:1);
$^1$HNMR: δ 7.77 (s, 1H), 7.09 (m, 4H), 6.64 (m, 1H), 6.58 (s, 1H), 6.52 (s, 2H), 5.99 (s, 1H), 4.41 (d, 1H), 4.18 (dd, 1H), 3.98 (dd, 1H), 3.81 (s, 6H), 3.70-3.60 (m, 4H), 3.30-3.20 (m, 4H), 3.00-2.90 (m, 2H), 2.80-2.90 (m, 2H), 2.60-2.30 (m, 5H), 2.20-2.10 (m, 1H), 2.04 (s, 3H), 1.40-1.35 (m, 2H).

EXAMPLE 68(60)

N-(2-{1-[(2S,3S)-2-(2,3-dihydro-1H-inden-2-ylmethyl)-3-(3,5-dimethoxy-4-methylphenyl)-3-hydroxypropyl]-1H-pyrrol-3-yl}acetyl)-4-morpholinesulfonamide TLC: Rf 0.33 (hexane:ethyl acetate=1:1);
$^1$HNMR: δ 7.97 (s, 1H), 7.09 (m, 4H), 6.69 (m, 1H), 6.65 (m, 1H), 6.50 (s, 2H), 6.02 (t, 1H), 4.42 (d, 1H), 4.22-4.00 (m, 2H), 3.82 (s, 6H), 3.71-3.65 (m, 4H), 3.51 (s, 2H), 3.35-3.30 (m, 4H), 3.00-2.90 (m, 2H), 2.50-2.30 (m, 3H), 2.20-1.80 (m, 2H), 2.06 (s, 3H), 1.40-1.30 (m, 2H).

EXAMPLE 68(61)

N-(3-{1-[(2S,3S)-2-(2,3-dihydro-1H-inden-2-ylmethyl)-3-(3,5-dimethoxy-4-methylphenyl)-3-hydroxypropyl]-1H-pyrrol-3-yl}propanoyl)-2-methyl-2-propanesulfonamide TLC: Rf 0.38 (hexane:ethyl acetate=1:1);
$^1$HNMR: δ 1.32-1.45 (m, 11H), 2.06 (s, 4H), 2.08-2.20 (m, 1H), 2.28-2.53 (m, 3H), 2.58-2.66 (m, 2H), 2.83 (t, 2H), 2.89-3.05 (m, 2H), 3.81 (s, 6H), 3.97 (dd, 1H), 4.12-4.24 (m, 1H), 4.44 (d, 1H), 5.96-6.03 (m, 1H), 6.52 (s, 2H), 6.57 (t, 1H), 6.63 (t, 1H), 7.04-7.17 (m, 4H), 7.42 (s, 1H).

EXAMPLE 68(62)

N-(3-{1-[(2S,3S)-2-(2,3-dihydro-1H-inden-2-ylmethyl)-3-(3,5-dimethoxy-4-methylphenyl)-3-hydroxypropyl]-1H-pyrrol-3-yl}propanoyl)-4-methyl-1,3-thiazole-2-sulfonamide TLC: Rf 0.30 (hexane:ethyl acetate=1:4);
$^1$HNMR: δ 1.28-1.47 (m, 2H), 2.04 (s, 3H), 2.07-2.21 (m, 1H), 2.24-2.52 (m, 7H), 2.51-2.61 (m, 2H), 2.76 (t, 2H), 2.85-3.04 (m, 2H), 3.78 (s, 6H), 3.97 (dd, 1H), 4.21 (dd, 1H), 4.41 (d, 1H), 5.92-5.96 (m, 1H), 6.51 (s, 2H), 6.57 (s, 1H), 6.62 (t, 1H), 7.06-7.13 (m, 4H), 7.23 (d, 1H).

EXAMPLE 68(63)

N-((2E)-3-{1-[(2S,3S)-2-(2,3-dihydro-1H-inden-2-ylmethyl)-3-(3,5-dimethoxy-4-methylphenyl)-3-hydroxypropyl]-1H-pyrrol-3-yl}-2-propenoyl)methanesulfonamide TLC: Rf 0.20 (hexane:ethyl acetate=1:1);
$^1$HNMR: δ 7.77 (s, 1H), 7.71 (d, 1H), 7.15-7.02 (m, 4H), 6.99 (m, 1H), 6.68 (m, 1H), 6.48 (s, 2H), 6.38 (m, 1H), 6.01 (d, 1H), 4.43 (d, 1H), 4.21 (dd, 1H), 4.06 (dd, 1H), 3.81 (s, 6H), 3.36 (s, 1H), 3.04-2.88 (m, 2H), 2.55-2.30 (m, 3H), 2.18 (m, 1H), 2.06 (s, 3H), 1.40 (m, 2H).

EXAMPLE 69 dimethyl((E)-2-{1-[(2S,3S)-3-{[tert-butyl(dimethyl)silyl]oxy}-2-(2,3-dihydro-1H-inden-2-ylmethyl)-3-(3,5-dimethoxy-4-methylphenyl)propyl]-1H-pyrrol-3-yl}vinyl)phosphonate To a tetrahydrofuran (10 ml) solution of tetramethyl methylenediphosphonate (262 mg), sodium hydride (60%; 45 mg) was added under ice-cooling, and the mixture was stirred at the same temperature for 10 minutes. Next, the compound (561 mg) produced in Example 60 was added thereto, followed by stirring at 50° C. overnight. To the reaction mixture, 1N hydrochloric acid was added, followed by extraction with ethyl acetate. The organic layer was washed with water and brine successively, dried over anhydrous magnesium sulfate, and concentrated. The residue was purified with silica gel column chromatography (hexane:ethyl acetate=1:1) to give the title compound (460 mg) having the following physical properties.
TLC: Rf 0.35 (hexane:ethyl acetate=1:1).

EXAMPLE 70 dimethyl2-{1-[(2S,3S)-2-(2,3-dihydro-1H-inden-2-ylmethyl)-3-(3,5-dimethoxy-4-methylphenyl)-3-hydroxypropyl]-1H-pyrrol-3-yl}ethylphosphonate Using the compound produced in Example 69 instead of ethyl(2E)-3-(1-{(2S)-2-[(S)-(3,5-dimethoxy-4-methylphenyl)(hydroxy)methyl]-5-phenylpentyl}-1H-pyrazol-4-yl) acrylate, procedures similar to Example 36 Example 19 were carried out to give the title compound having the following physical properties.
TLC: Rf 0.33 (ethyl acetate);
$^1$HNMR: δ 7.16-7.04 (m, 4H), 6.59 (t, 1H), 6.51-6.48 (m, 3H), 5.97 (t, 1H), 4.46 (dd, 1H), 4.12 (dd, 1H), 3.99 (dd, 1H), 3.81 (s, 6H), 3.73 (d, 3H), 3.72 (d, 3H), 3.03-2.88 (m, 2H), 2.83-2.70 (m, 2H), 2.49-2.30 (m, 3H), 2.19-1.95 (m, 6H), 1.37 (t, 2H).

EXAMPLE 71 methyl hydrogen 2-{1-[(2S,3S)-2-(2,3-dihydro-1H-inden-2-ylmethyl)-3-(3,5-dimethoxy-4-methylphenyl)-3-hydroxypropyl]-1H-pyrrol-3-yl}ethylphosphonate To a 2-pentanone (2 ml) solution of the compound (40 mg) produced in Example 70, lithium bromide (8 mg) was added, and the mixture was stirred at 105° C. for 4.5 hours. The reaction mixture was concentrated, and 1N hydrochloric acid was added to the residue, followed by extraction with ethyl acetate. The organic layer was washed with water and brine successively, dried over anhydrous magnesium sulfate, and concentrated. The residue was purified with silica gel column chromatography (dichloromethane:methanol=4:1) to give the title compound (34 mg) having the following physical properties.
TLC: Rf 0.46 (acetic acid:methano:dichloromethane=1:20:80);
$^1$HNMR (CD$_3$OD): δ 7.06-6.95 (m, 4H), 6.57 (s, 2H), 6.53 (t, 1H), 6.46-6.43 (m, 1H), 5.88-5.86 (m, 1H), 4.46 (d, 1H), 4.01 (dd, 1H), 3.88 (dd, 1H), 3.79 (s, 6H), 3.53 (d, 3H), 2.94-2.78 (m, 2H), 2.70-2.59 (m, 2H), 2.32-2.05 (m, 4H), 2.00 (s, 3H), 1.85-1.71 (m 2H), 1.47-1.23 (m, 2H).

EXAMPLE 72 methyl4-(2-methoxy-2-oxoethyl)-1H-pyrrole-3-carboxylate

To a lithium bis(trimethylsilyl)amide (1M; tetrahydrofuran solution) (21 ml), a tetrahydrofuran (100 ml) solution of p-toluenesulfonylmethylisocyanide (4.04 g) was added dropwise at −78° C., and the mixture was stirred for 30 minutes. Successively, a tetrahydrofuran (20 ml) solution of dimethyl glutaconate (3.78 g) was added dropwise thereto, followed by stirring while raising the temperature to room temperature for 2 hours. The reaction mixture was concentrated, and the residue was washed with water and 1N hydrochloric acid successively, followed by extraction with ethyl acetate. The organic layer was washed with 1N hydrochloric acid, a saturated aqueous sodium hydrogen carbonate solution, water and brine successively, dried over anhydrous magnesium sulfate, and concentrated. The residue was purified with silica gel column chromatography (hexane:ethyl acetate=3:2) to give the title compound (2.11 g) having the following physical properties.

TLC: Rf 0.49 (hexane:ethyl acetate=1:1).

EXAMPLE 73 methyl1-[(2S,3S)-3-{[tert-butyl(dimethyl)silyl]oxy}-2-(2,3-dihydro-1H-inden-2-ylmethyl)-3-(3,5-dimethoxy-4-methylphenyl)propyl]-4-(2-methoxy-2-oxoethyl)-1H-pyrrole-3-carboxylate To an N,N-dimethylformamide (10 ml) solution of the compound (523 mg) produced in Example 58, the compound (376 mg) produced in Example 72 and cesium carbonate (933 mg) were added, followed by stirring at 120° C. for 1 hour. The reaction mixture was dissolved in water, and extracted with t-butyl methyl ether. The organic layer was washed with water and brine successively, dried over anhydrous magnesium sulfate, and concentrated. The residue was purified with silica gel column chromatography (hexane:ethyl acetate=6:1) to give the title compound (364 mg) having the following physiological properties.

TLC: Rf 0.39 (hexane:ethyl acetate=4:1).

EXAMPLE 74

[1-[(2S,3S)-2-(2,3-dihydro-1H-inden-2-ylmethyl)-3-(3,5-dimethoxy-4-methylphenyl)-3-hydroxypropyl]-4-(methoxycarbonyl)-1H-pyrrol-3-yl]acetic acid To a methanol (4 ml)-tetrahydrofuran (4 ml) solution of the compound produced in Example 73 (364 mg), a 1N aqueous sodium hydroxide solution (2 ml) was added, and the mixture was stirred at 35° C. for 2.5 hours. The reaction mixture was concentrated, and the residue was diluted with 1N hydrochloric acid, followed by extraction with ethyl acetate. The organic layer was washed with 1N hydrochloric acid, water and brine successively, dried over anhydrous magnesium sulfate, and concentrated. The residue was purified with silica gel column chromatography (hexane:ethyl acetate=2:1) to obtain [1-[(2S,3S)-3-{[tert-butyl(dimethyl)silyl]oxy}-2-(2,3-dihydro-1H-inden-2-ylmethyl)-3-(3,5-dimethoxy-4-methylphenyl)propyl]-4-(2-methoxy-2-oxoethyl)-1H-pyrrol-3-yl]acetic acid (328 mg), and then procedures similar to Example 19 were carried out to give the title compound (235 mg) having the following physiological properties.

TLC: Rf 0.32 (ethyl acetate:hexane=2:1);
$^1$HNMR: δ 7.28 (d, 1H), 7.16-7.06 (m, 4H), 6.67 (d, 1H), 6.47 (s, 2H), 4.39 (d, 1H), 4.21 (dd, 1H), 4.01 (dd, 1H), 3.85 (s, 3H), 3.81 (s, 6H), 3.70 (s, 2H), 3.05-2.89 (m, 2H), 2.52-2.28 (m, 3H), 2.19-2.03 (m, 4H), 1.44-1.28 (m, 2H).

EXAMPLE 74(1)

[1-[(2S,3S)-2-(2,3-dihydro-1H-inden-2-ylmethyl)-3-(3,5-dimethoxy-4-methylphenyl)-3-hydroxypropyl]-4-(ethoxycarbonyl)-1H-pyrrol-3-yl]acetic acid Using ethyl4-(2-methoxy-2-oxoethyl)-1H-pyrrole-3-carboxylate instead of the compound produced in Example 72, procedures similar to the methods shown in Example 73→Example 74 were carried out to give the title compound having the following physical properties.

TLC: Rf 0.59 (dichloromethane:methanol=9:1);
$^1$HNMR (CDCl$_3$+CD$_3$OD): δ 7.30 (d, 1H), 7.15-7.07 (m, 4H), 6.64 (d, 1H), 6.50 (s, 2H), 4.40 (d, 1H), 4.27 (q, 2H), 4.18 (dd, 1H), 3.99 (dd, 1H), 3.82 (s, 6H), 3.70 (s, 2H), 3.02-2.92 (m, 2H), 2.52-2.32 (m, 3H), 2.19-2.08 (m, 1H), 2.06 (s, 3H), 1.48-1.29 (m, 5H).

EXAMPLE 75

(2S,3S)-3-(4-acetyl-3,5-dimethoxyphenyl)-3-{[tert-butyl(dimethyl)silyl]oxy}-2-(2,3-dihydro-1H-inden-2-ylmethyl)propylacetate A tetrahydrofuran (40 ml) solution of (2S,3S)-3-{[tert-butyl(dimethyl)silyl]oxy}-2-(2,3-dihydro-1H-inden-2-ylmethyl)-3-(3,5-dimethoxyphenyl)propanol (obtained by carrying out procedures similar to Example 12→Example 13→Example 14→Example 15 using 3-(2,3-dihydro-1H-inden-2-yl)propanoyl chloride instead of 5-phenylpentanoyl chloride and using 3,5-dimethoxybenzaldehyde instead of 3,5-dimethoxy-4-methylbenzaldehyde) (3.70 g) was cooled to 0° C. under argon atmosphere, and n-butyl lithium (1.58 M hexane solution; 15.4 ml) was added dropwise thereto, followed by stirring while raising the temperature to room temperature for 1 hour. Again, the mixture was cooled to 0° C., and copper bromide (I) (2.32 g) and acetyl chloride (2.31 ml) were added thereto, followed by stirring while raising the temperature to room temperature for 2 hours. A saturated aqueous ammonium chloride solution was added to the reaction mixture, followed by extraction with ethyl acetate. The extract was washed with brine, dried over anhydrous magnesium sulfate, and concentrated to give the title compound having the following physical properties.

TLC: Rf 0.55 (n-hexane:ethyl acetate=2:1);
$^1$HNMR: δ 7.20-7.05 (m, 4H), 6.49 (s, 2H), 4.68 (d, 1H), 4.25-4.08 (m, 2H), 3.79 (s, 6H), 3.12-2.90 (m, 2H), 2.60-2.38 (m, 4H), 2.48 (s, 3H), 2.02 (s, 3H), 1.50 (m, 2H), 0.90 (s, 9H), 0.04 (s, 3H), −0.15 (s, 3H).

EXAMPLE 76

1-{4-[(1S,2S)-1-{[tert-butyl(dimethyl)silyl]oxy}-3-(2,3-dihydro-1H-inden-2-yl)-2-(hydroxymethyl)propyl]-2,6-dimethoxyphenyl}ethanone To a methanol (50 ml) solution of the compound produced in Example 75, potassium carbonate (4.00 g) was added, and the mixture was stirred at 50° C. for 15 hours. Water was added to the reaction mixture, followed by extraction with ethyl acetate. The extract was washed with brine, dried over anhydrous magnesium sulfate, and concentrated. The residue was purified with silica gel column chromatography (hexane:ethyl acetate=6:1→4:1→2:1) to give the title compound (1.40 g) having the following physical properties.

TLC: Rf 0.32 (hexane:ethyl acetate=2:1);
$^1$HNMR: δ 7.20-7.05 (m, 4H), 6.52 (s, 2H), 4.77 (d, 1H), 3.84 (m, 1H), 3.80 (s, 6H), 3.58 (m, 1H3.15-2.95 (m, 2H), 2.83 (m, 1H), 2.68-2.42 (m, 3H), 2.49 (s, 3H), 1.78 (m, 2H), 0.94 (s, 9H), 0.10 (s, 3H), −0.13 (s, 3H).

EXAMPLE 77

3-{1-[(2S,3S)-3-(4-acetyl-3,5-dimethoxyphenyl)-2-(2,3-dihydro-1H-inden-2-ylmethyl)-3-hydroxypropyl]-1H-pyrrol-3-yl}propanoic acid Using the compound produced in Example 76 instead of the compound produced in Example 15, procedures similar to Example 16→Example 60→Example 34→Example 36→Example 20→Example 19 were carried out to give the title compound having the following physical properties.

TLC: Rf 0.45 (dichloromethane:methanol=9:1);
$^1$HNMR: δ 7.18-7.05 (m, 4H), 6.55 (dd, 1H), 6.50 (s, 2H), 6.47 (brs, 1H), 5.97 (dd, 1H), 4.49 (d, 1H), 4.08 (m, 1H), 3.94 (dd, 1H), 3.79 (s, 6H), 3.04-2.92 (m, 2H), 2.77 (t, 2H), 2.56 (t, 2H), 2.55-2.35 (m, 3H), 2.46 (s, 3H), 2.12 (m, 1H), 1.40 (m, 2H).

EXAMPLE 78

3-{1-[(2S,3S)-2-(2,3-dihydro-1H-inden-2-ylmethyl)-3-hydroxy-3-(4-isopropenyl-3,5-dimethoxyphenyl)propyl]-1H-pyrrol-3-yl}propanoic acid To a dichloromethane (3 ml) solution of the compound (350 mg) produced in Example 77, zinc bromide (937 mg) was added under argon atmosphere, and the mixture was stirred at room temperature for 1 hour. The mixture was cooled to 0° C., methyllithium (1M diethyl ether solution; 10.4 ml) was added thereto, followed by stirring while raising the temperature to room temperature for 3 hours. To the reaction mixture, 2N hydrochloric acid was added, followed by extraction with ethyl acetate. The extract was washed with brine, dried over anhydrous magnesium sulfate, and concentrated. The residue was purified with silica gel column chromatography (hexane:ethyl acetate=2:1 →1:1) to give the title compound (57 mg) having the following physiological properties.

TLC: Rf 0.42 (dichloromethane:methanol=9:1);
$^1$HNMR: δ 7.20-7.03 (m, 4H), 6.59 (m, 1H), 6.53 (s, 2H), 6.52 (m, 1H), 5.98 (m, 1H), 5.32 (brs, 1H), 4.85 (brs, 1H), 4.47 (d, 1H), 4.11 (m, 1H), 3.99 (dd, 1H), 3.80 (s, 6H), 3.10-2.90 (m, 2H), 2.79 (t, 2H), 2.58 (t, 2H), 2.50-2.32 (m, 3H), 2.18 (m, 1H), 1.99 (s, 3H), 1.42-1.38 (m, 2H).

BIOLOGICAL EXAMPLES

It was demonstrated by the following experiments and the like that the compound of the present invention has antagonistic activity against an LPA receptor (for example, EDG-2). The whole procedures were carried out by preparing gene highly-expressed cells based on the basic genetic engineering techniques and using the conventional methods. Also, in the measurement method of the present invention, measurement accuracy and/or measurement sensitivity were improved in order to evaluate the compound of the present invention. Detailed experimental methods are shown below.

Evaluation of EDG-2 Antagonistic Activity by Monitoring the Change of Intracellular Calcium Ion Concentration:

The EDG-2 antagonistic activity was evaluated by using Chinese hamster ovary (CHO) cells which overexpressed human EDG-2 gene. The EDG-2-expressing cells were cultured with Ham's F12 medium (manufactured by GIBCO BRL, No. 11765-047) containing 10% FBS (fetal bovine serum), penicillin/streptomycin and blasticidin (5 μg/ml). Firstly, in order to incorporate Fura2-AM (manufactured by Dojindo, No. 348-05831) into the cells, the cells were incubated in 5 μM Fura2-AM solution (10% FBS, 20 mM HEPES buffer (pH 7.4), 2.5 mM probenecid (manufactured by Sigma, No. P-8761)-containing Ham's F12 medium) at 37° C. for 60 minutes. Next, the cells were washed with 20 mM HEPES buffer (pH 7.4) and Hanks solution containing 2.5 mM probenecid once, and immersed into the Hanks solution until assaying. A plate was set in a fluorescence drug screening system (manufactured by Hamamatsu Photonics K.K., FDSS-2000, FDSS-6000) and intracellular calcium ion concentration was measured for 30 seconds without stimulation, and a solution of the compound of present invention was added. Five minutes thereafter, LPA (final concentration: 100 nM) was added, and the intracellular calcium ion concentration before and after the addition at the interval of 3 seconds (excitation wavelength: 340 nm and 380 nm, fluorescence wavelength: 500 nm). The compound of the present invention was dissolved in DMSO and added so as to give a final concentration of 1 nM to 10 μM. As LPA, 1-oleoyl(18:1)-LPA (manufactured by Sigma) or 1-linoleyl(18:3) -LPA was used. The 1-linoleyl(18:3)-LPA was synthesized and purified by either of the following 2 methods: (1) a method synthesizing it from 18:3-LPC (linoleyl(18:3)-lysophosphatidyl choline) (manufactured by Sedary)) with PLD (phospholipase D), or (2) a method for firstly synthesizing 18:3-LPC from 18:3-PC (linoleyl(18:3)-phosphatidyl choline) (manufactured by Avanti Polar Lipids) with $PLA_2$ and then synthesizing LPA with PLD. EDG-2 antagonistic activity was calculated as an inhibition rate (%) by the following equation, wherein the peak value of LPA (final concentration: 100 nM) in a well into which DMSO containing no the compound of the present invention was added was regarded as a control value (A), and in the cells treated with the compound the difference (B) between the value before addition of LPA and that after the addition was obtained and compared with the control value.

$$\text{Inhibtion ratio }(\%) \frac{(A-B)}{A} \times 100$$

The $IC_{50}$ value was calculated as a concentration of the compound to be tested which showed 50% inhibition.

As a result, the compound of the present invention showed the inhibition at a concentration of 10 μM or less. For example, the compound of Example 20(2) has an $IC_{50}$ value of 0.040 μM.

Effect on Urethral Pressure of Rats (in vivo):

Male CD(SD)IGS rats (Japan Charles River, 8 to 9-week-old at the use) were anesthetized by subcutaneous administration of urethane (1.2 g/kg). After dissection at the cervical midline, a jugular vein catheter for compound administration and an artery catheter for blood pressure measurement were inserted. Next, after dissection at the hypogastric midline, the urethra was ligated under the pubic bone. An urethra catheter for urethral pressure measurement was inserted into the urethra from the dissected the top of the bladder, and ligated and fixed at the bladder neck. Each of the urethra catheter and the artery catheter was connected with a pressure-transducer, and the urethral pressure and blood pressure were measured. Next, the urethral pressure was adjusted on about 20 mmHg and the animal was left at rest to keep this value. Then, the test compound was intravenously administered, and the urethral pressure and blood pressure were measured for 20 minutes. Then, in order to obtain the base line of the urethral pressure after the death, 1 ml of somnopentyl was intravenously added.

After the urethral pressure was completely decreased until it became stable, the value was regarded as the base line value after the death.

The test compound was administered at respective doses. Also, as vehicle, a solution of meylon:physiological saline =1:3 was used. In order to evaluate the in vivo effect of the test compound, the change of the urethral pressure after the administration of the compound was compared with that after the administration of the vehicle. For the evaluation of the effect of the test compound on the urethral pressure, the values subtracting the urethral pressure before the administration from the measured urethral pressures every 2 minutes after the administration were obtained and a graph of the change with time (decreased amount of the urethral pressure from the base line) was prepared.

As a result, there was little change in the urethral pressure after the administration in the vehicle administration group, whereas the significantly remarkable decrease of the urethral pressure was observed in the compound of the present invention administration group. For example, the significantly remarkable decrease of the urethral pressure was observed in the administration group of the compound of Example 20(2) at a dose of 0.1 mg/kg to 1 mg/kg, and the maximum decreased amount in this group was about 30 to 40% of the absolute value of the urethral pressure (the urethral pressure before the administration - the base line value after the death) so that the effect is potent.

Measurement of Bioavailability (BA):

After administering the compound of the present invention to an SD rat (about 8-week-old), blood was collected from the jugular vein with time, the concentration of the compound of the present invention in blood plasma was measured, and the bioavailability after the oral administration of the compound of the present invention was calculated based on the change. BA is represented by "AUC at the oral administration/AUC at the intravenous administration×100 (%)", and AUC represents "concentration in blood - area below time curve (ng·hr/ml)".

The utility of the compound of formula (I) of the present invention can be evaluated by the following various experiments, methods described in Biological Examples and method which can be carried out by modifying them. Also, kinetically excellent properties of the compound of formula (I) of the present invention, such as length of the half-life in blood, stability in the digestive organs, oral absorbability and bioavailability, can easily evaluated by known methods, such as methods described in *Drug Bioavailability (Science of Evaluation and Improvement)*, published by Gendai Iryo Sha, Jul. 6, 1998.

Formulation Example 1

(4-{(2S)-2-[(S)-Hydroxy(3,4,5-trimethoxyphenyl)methyl]-5-phenylpentyl}phenyl)acetic acid (compound in Example 20(2), 50.0 g), calcium carboxymethyl cellulose (2 g), magnesium stearate (1 g) and microcrystalline cellulose (47 g) were mixed in a conventional manner, and then punched out to give 1,000 tablets each containing 50 mg of the active ingredient.

Formulation Example 2

(4-{(2S)-2-[(S)-Hydroxy(3,4,5-trimethoxyphenyl)methyl]-5-phenylpentyl}phenyl)acetic acid (compound in Example 20(2), 20 g), mannitol (200 g), and distilled water (10 L) were mixed in a conventional manner, sterilized in a conventional technique, filled in ampoules 5 ml each and freeze-dried over in a conventional manner to give 1,000 ampoules each containing 20 mg of the active ingredient.

INDUSTRIAL APPLICABILITY

Since the compound of formula (I) of the present invention, a salt thereof or a prodrug thereof is antagonistic to an LPA receptor (particularly, EDG-2), it can prevent and/or treat various diseases and is useful as a pharmaceutical.

The invention claimed is:

1. A compound of formula (I)

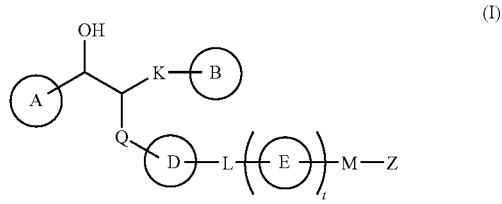

wherein ring A represents a benzene ring which may have a substituent(s), wherein the substituent(s) is 1 to 5 optional substituent(s) selected from the group of methyl, ethyl, a fluorine atom, a chlorine atom, methoxy, ethoxy, and acetyl;

ring B represents a benzene ring which may have a substituent(s), a thiophene ring which may have a substituent(s), an indan ring which may have a substituent(s), or a 1,3-benzodioxole ring which may have a substituent (s), wherein the substituent(s) is 1 to 5 optional substituent(s) selected from the group consisting of a fluorine atom, and a chlorine atom;

K represents C1-4 alkylene;

Q represents methylene, or ethylene;

M represents a bond, C1-4 alkylene which may have a substituent(s), or C2-4 alkenylene which may have a substituent(s), wherein the substituent(s) is 1 to 5 optional substituent(s) of methyl;

ring D represents a benzene ring which may have a substituent(s), a pyrrole ring which may have a substituent (s), a pyrazole ring which may have a substituent(s), or a thiazole ring which may have a substituent(s), wherein the substituent(s) is 1 to 5 optional substituent(s) selected from the group consisting of, methyl, and methoxycarbonyl;

ring E represents a benzene ring;

L represents a bond, or —O—;

Z represents COOH, CONHSO$_2$R$^1$, in which R$^1$ represents methyl, or, a benzene ring which may have a substituent (s), wherein the substituent(s) is 1 to 5 optional substituent(s) selected from the group consisting of methyl; and t represents 0 or 1, or a salt thereof.

2. The compound according to claim 1, wherein the compound of formula (I) is an optically active compound of formula (I-A):

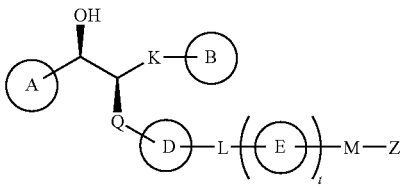

(I-A)

wherein ◢ represents β-configuration; and other symbols have the same meanings as described in claim 1.

3. The compound according to claim 1, wherein ring B is an indan ring which may have a substituent(s).

4. The compound according to claim 1, wherein ring D is a benzene ring which may have a substituent(s), a pyrazole ring which may have a substituent(s) or a pyrrole ring which may have a substituent(s).

5. The compound according to claim 1, wherein

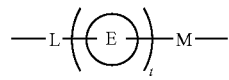

is methylene which may be substituted, ethylene which may be substituted, propylene which may be substituted, or ethenylene which may be substituted.

6. The compound according to claim 1,
wherein ring A is a benzene ring which may have a substituent(s);
ring B is an indan ring which may have a substituent(s);
ring D is a benzene ring which may have a substituent(s), a pyrazole ring which may have a substituent(s) or a pyrrole ring which may have a substituent(s);

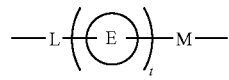

is methylene which may be substituted, ethylene which may be substituted, propylene which may be substituted, or ethenylene which may be substituted; and
Z is —COOH; —CONHSO$_2$R$^1$, in which R$^1$ is methyl, a benzene ring which may have a substituent(s).

7. The compound according to claim 1, which is selected from the group consisting of:
(1) {1-[(2S,3S)-2-(2,3-dihydro-1H-inden-2-ylmethyl)-3-(3,5-dimethoxy-4- methylphenyl)-3-hydroxylpropyl]-1H-pyrrol-3-yl}acetic acid,
(2) (1-{(2S)-2-[(S)-(3,5-dimethoxy-4-methylphenyl)(hydroxy)methyl]-5-thien-3- ylpentyl}-1H-pyrrol-3-yl) acetic acid,
(3) {1-[(2S,3S)-2-(1,3-benzodioxol1-2-ylmethyl)-3-(3,5-dimethoxy-4-methylphenyl)- 3-hydroxylpropyl]-1H-pyrrol-3-yl}acetic acid,
(4) {1-[(2S,3 S)-2-(2,3-dihydro- 1H-inden-2-ylmethyl)-3-hydroxy-3 trimethoxyphenyl)propyl]-1H-pyrrol-3-yl}acetic acid,
(5) {1-[(2S,3S)-3-(4-acetyl-3,5-dimethoxyphenyl)-2-(2, 3-dihydro-1H-inden-2- ylmethyl)-3-hydroxylpropyl]-1H-pyrrol-3-yl}acetic acid,
(6) {1-[(2S,3 S)-2-(2,3-dihydro-1H-inden-2-ylmethyl)-3-(4-ethyl-3,5- dimethoxyphenyl)-3-hydroxylpropyl]-1H-pyrrol-3-yl}acetic acid,
(7) 3-{1-[(2S,3S)-2-(2,3-dihydro-1H-inden-2-ylmethyl)-3-(3,5-dimethoxy-4- methylphenyl)-3-hydroxylpropyl]-1H-pyrrol-3-yl}propanoic acid,
(8) 3-{1-[(2S,3S)-2-(2,3-dihydro-1H-inden-2-ylmethyl)-3-hydroxy-3-(3,4,5- trimethoxyphenyl)propyl]-1H-pyrrol-3-yl}propanoic acid,
(9) 3-{1-[(2S,3S)-3-(4-acetyl-3,5-dimethoxyphenyl)-2-(2,3-dihydro-1H-inden-2- ylmethyl)-3-hydroxylpropyl]-1H-pyrrol-3-yl}propanoic acid,
(10) 3-{1-[(2S,3S)-2-(2,3-dihydro-1H-inden-2-ylmethyl)-3-(4-ethyl-3,5- dimethoxyphenyl)-3-hydroxylpropyl]-1H-pyrrol-3-yl}propanoic acid,
(11) 2-{1-[(2S,3 S)-2-(2,3-dihydro- 1H-inden-2-ylmethyl)-3-(3,5-dimethoxy-4- methylphenyl)-3-hydroxylpropyl]-1H-pyrrol-3-yl }-N-(methylsulfonyl)acetamide,
(12) [1-[(2S,3S)-2-(2,3-dihydro-1H-inden-2-ylmethyl)-3-(3,5-dimethoxy-4- methylphenyl)-3-hydroxylpropyl]-4-(methoxylcarbonyl)-1H-pyrrol-3-yl]acetic acid,
(13) N-(3- {1-[(2S,3 S)-2-(2,3-dihydro-1H-inden-2-ylmethyl)-3-(3,5-dimethoxy-4- methylphenyl)-3-hydroxylpropyl]-1H-pyrrol-3yl}propanoyl)-2-methylbenzenesulfonamide,
(14) (2E)-3- {1-[(2S,3 S)-2-(2,3-dihydro-1H-inden-2-ylmethyl)-3-(3,5-dimethoxy-4- methylphenyl)-3-hydroxylpropyl]-1H-pyrrol-3yl}acrylic acid,
(15) 2-{1-[(2S,3S)-2-(2,3-dihydro-1H-inden-2-ylmethyl)-3-(3,5-dimethoxy-4- methylphenyl)-3-hydroxylpropyl]-1H-pyrol-3-yl}-2-methylpropanoic acid, and
(16) (2E)-3-{1-[(2S,3S)-2-(2,3-dihydro-1H-inden-2-ylmethyl)-3-(3,5-dimethoxy-4- methylphenyl)-3-hydroxylpropyl]-1H-pyrrol-3-yl}-2-methylacrylic acid.

8. A pharmaceutical composition comprising the compound of formula (I) according to claim 1, or a salt thereof.

9. The pharmaceutical composition according to claim 8, which is an LPA receptor antagonist, wherein the LPA receptor is EDG-2.

10. The pharmaceutical composition according to claim 8, which is an agent for prevention and/or treatment for urinary system disease.

11. A method for treatment of urinary system disease selected from the group of prostatic hypertrophy, neurogenic bladder dysfunction disease, dysuria, pollakiuria, night urination and urodynia, which comprises administering to a mammal an effective amount of the compound of formula (I) according to claim 1, or a salt thereof.

12. A pharmaceutical composition comprising a combination of the compound of formula (I) according to claim 1, or a salt thereof with at least one agent selected from an LPA receptor antagonist, an α1 blocking agent, an anticholinergic agent, a 5α-reductase inhibitor and an anti-androgenic agent.

* * * * *